(12) United States Patent
Bakry et al.

(10) Patent No.: US 8,399,055 B2
(45) Date of Patent: Mar. 19, 2013

(54) OPEN CHANNEL SOLID PHASE EXTRACTION SYSTEMS AND METHODS

(76) Inventors: Rania Bakry, Innsbruck (AT); Gunther Bonn, Zirl (AT); Douglas T. Gjerde, Saratoga, CA (US); Christian W. Huck, Innsbruck (AT); Gunther Stecher, Götzens (AT)

(*) Notice: Subject to any disclaimer, the term of this patent is extended or adjusted under 35 U.S.C. 154(b) by 1060 days.

(21) Appl. No.: 11/488,558

(22) Filed: Jul. 18, 2006

(65) Prior Publication Data
US 2007/0036685 A1 Feb. 15, 2007

Related U.S. Application Data

(60) Provisional application No. 60/701,659, filed on Jul. 21, 2005.

(51) Int. Cl.
*B05D 7/22* (2006.01)

(52) U.S. Cl. ..... 427/230; 427/333; 427/387; 427/248.1; 204/479; 204/485; 422/400; 436/527

(58) Field of Classification Search ............. 424/78.1; 422/99, 103, 400; 204/451; 427/230
See application file for complete search history.

(56) References Cited

U.S. PATENT DOCUMENTS

| | | | | |
|---|---|---|---|---|
| 5,595,653 A * | 1/1997 | Good et al. | | 210/289 |
| 5,620,850 A * | 4/1997 | Bamdad et al. | | 530/300 |
| 7,122,640 B2 * | 10/2006 | Gjerde et al. | | 530/412 |
| 2005/0236272 A1* | 10/2005 | Patel | | 204/600 |
| 2007/0196833 A1* | 8/2007 | Gjerde | | 435/6 |

OTHER PUBLICATIONS

Chiari et al. Rapid capillary coating by epoxy-poly-(dimethylacrylamide): Performance in capillary zone electrophoresis of protein and polystyrene carboxylate. Electrophoresis. vol. 22, Issue 4. Feb. 2001. pp. 656-659.*
G. Gross et al, J. Chromatogr. A, 2004, pp. 185-192, vol. 1029.
G. Gross et al, Anal. Chem., 2003, pp. 4558-4564, vol. 75, No. 17.
L. Yang et al, Anal. Chem., 2005, pp. 1840-1846, vol. 77.
F. Liu et al, Analytica Chimica Acta, 2005, pp. 249-254, vol. 258.
F. Liu et al, J. Chromatogr. A, 2005, pp. 205-214, vol. 1083.
C. Jiang et al, J. Virol., 2004, pp. 8994-9006, vol. 78, No. 17.
Z. Guo et al, Electrophoresis, 2003, pp. 3633-3639, vol. 24.
L. Wells et al, Molecular & Cellular Proteomics 1.10, 2002, pp. 791-804, MCP Papers in Press.
W. Zhou et al, J. Am. Soc. Mass. Spectrom., 2000, pp. 273-282, vol. 11.
H. Liu et al, Anal. Chem., 2004, pp. 4223-4232, vol. 76, No. 14.
J. Gobom et al, Journal of Mass Spectrometry, 1999, pp. 105-116, vol. 34.
A. Frenzel et al, J. Chromatogr. B, 2003, pp. 325-329, vol. 793.
A. Stensballe et al, Proteomics, 2001, pp. 207-222, vol. 1.
J. Rappsilber et al, Anal. Chem., 2003, pp. 663-670, vol. 75, No. 3.
N. Aprilita et al, Journal of Proteome Research, 2005, pp. 2312-2319, vol. 4.
Q. Luo et al, J. Chromatogr. A, 2001, pp. 255-264, vol. 926.
N. Na et al, Analytica Chimica Acta, 2004, pp. 139-147, vol. 527.
J. Hsu et al, Electrophoresis, 2004, pp. 3840-3847, vol. 25.
Z. Yang and W. Hancock, J. Chromatogr. A, 2004, pp. 79-88, vol. 1053.
V. Ratnala et al, Eur. J. Biochem., 2004, pp. 2636-2646, vol. 271.
M. Hennion, J. Chromatogr. A., 1999, pp. 3-54, vol. 856.

* cited by examiner

*Primary Examiner* — Sally Merkling
(74) *Attorney, Agent, or Firm* — Sue S. Kalman

(57) ABSTRACT

The invention provides, inter alia, capillary extraction devices, and methods of making and using the same.

6 Claims, 19 Drawing Sheets

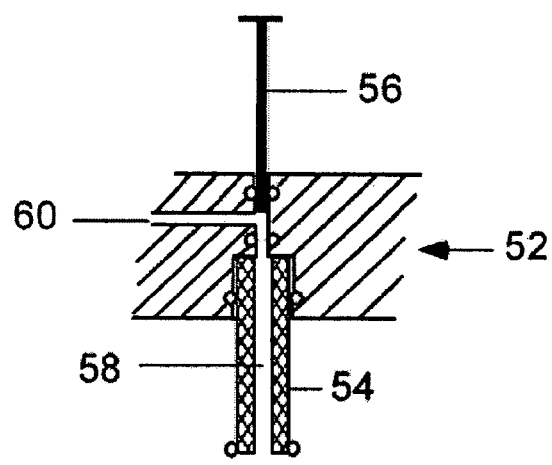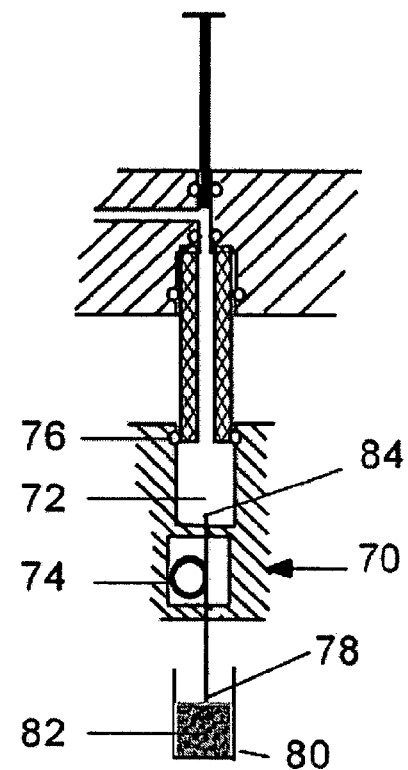
*FIG.-7A*  *FIG.-7B*

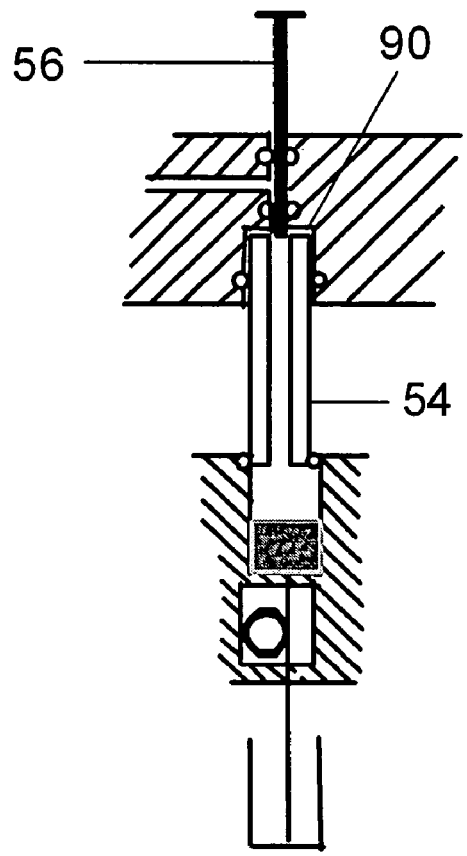
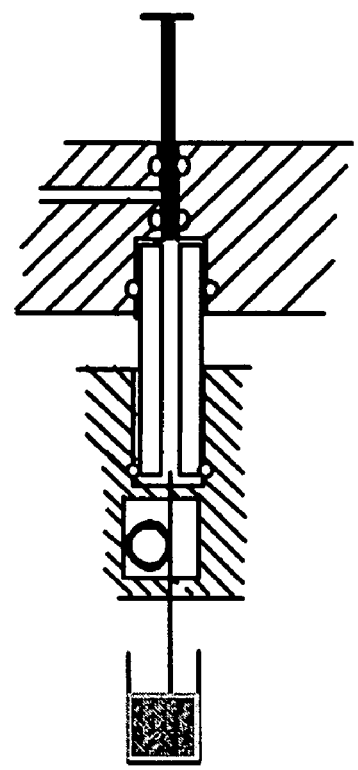
*FIG-7C*  *FIG-7D*

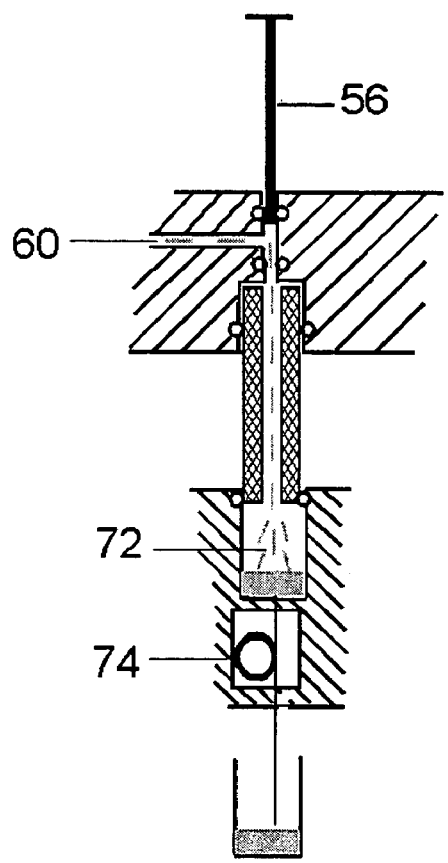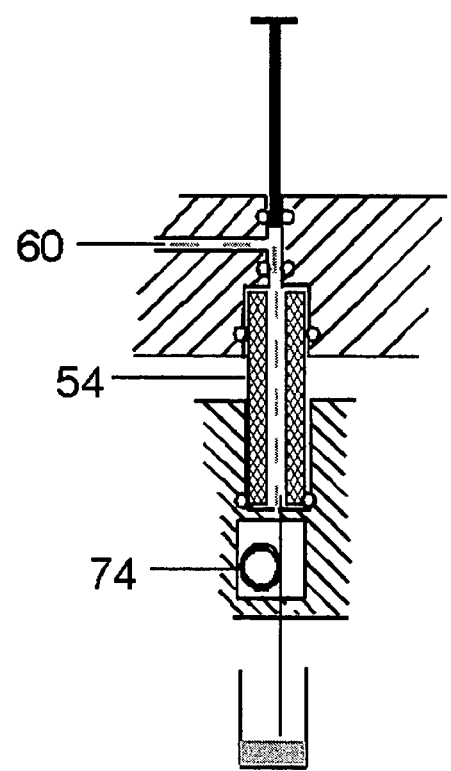
FIG-7E  FIG-7F

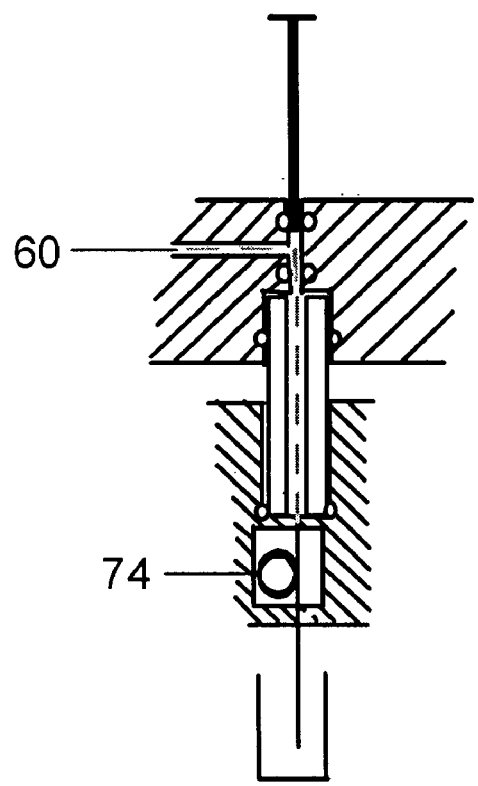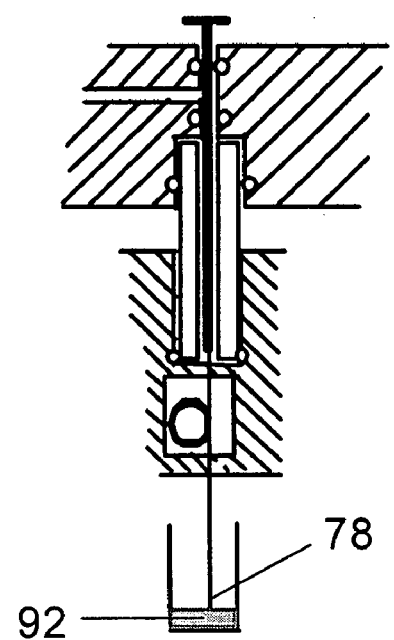
*FIG.-7G*  *FIG. 7H*

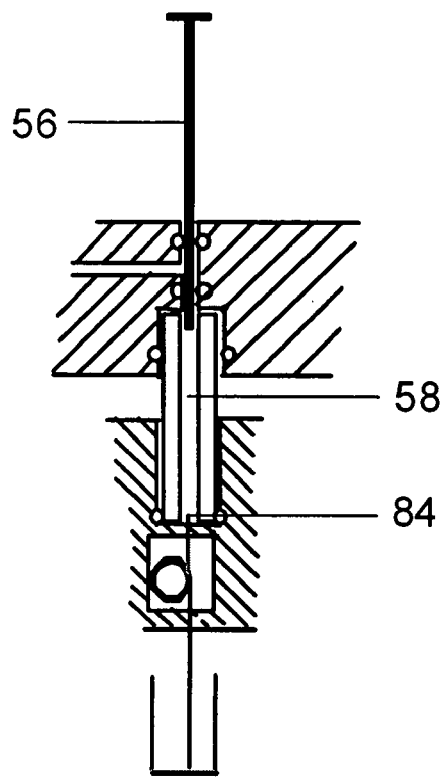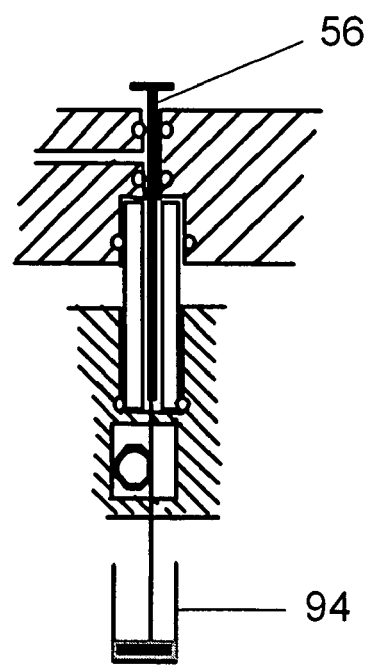
*FIG-7I*   *FIG-7J*

A
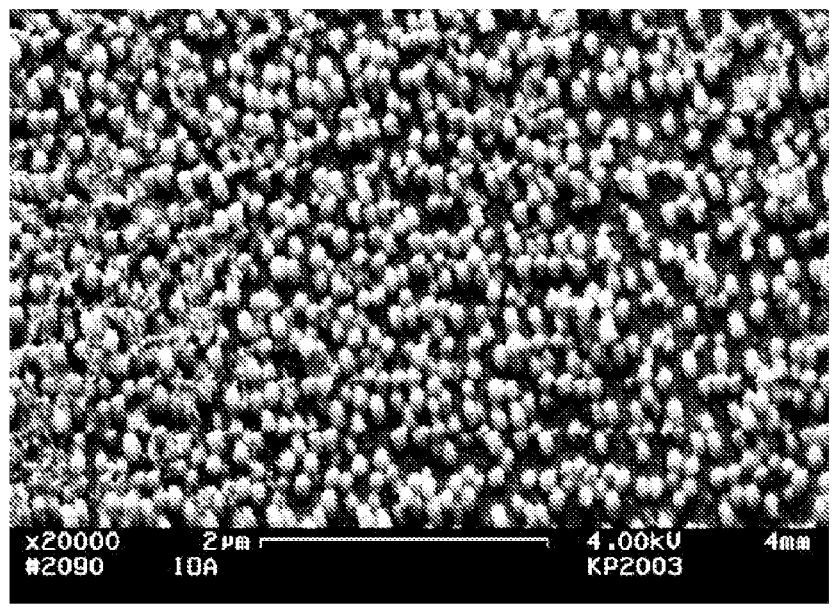
B
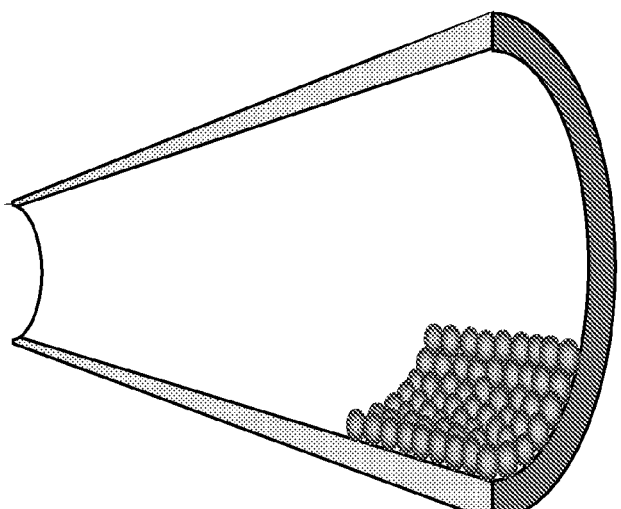
Fig. 9

OPEN CHANNEL SOLID PHASE EXTRACTION SYSTEMS AND METHODS

CROSS-REFERENCE TO RELATED APPLICATIONS

This application claims priority to and benefit of U.S. Provisional Application Ser. No. 60/701,659 filed Jul. 21, 2005; U.S. patent application Ser. No. 10/434,713 filed May 8, 2003; U.S. patent application Ser. No. 10/733,685 filed Dec. 10, 2003; U.S. patent application Ser. No. 10/733,664 filed Dec. 10, 2003; U.S. patent application Ser. No. 10/754,775 filed Jan. 8, 2004; U.S. patent application Ser. No. 10/866,283 filed Jun. 9, 2004; U.S. patent application Ser. No. 11/361,128 filed Feb. 24, 2006, and U.S. patent application Ser. No. 11/408,657 filed Apr. 20, 2006, the disclosures of which are incorporated herein by reference in their entirety for all purposes.

FIELD OF THE INVENTION

This invention relates to devices and methods for performing solid phase extractions in an open channel device, e.g., an extraction capillary. In some embodiments the invention is used for purifying, separating and/or concentrating an analyte. The analytes can be biomolecules or biomolecule complexes, including biological macromolecules such as polypeptides, polynucleotides, and/or polysaccharides.

BACKGROUND OF THE INVENTION

Solid phase extraction is a powerful sample preparation tool to perform extraction, fractionation, pre-concentration as well as clean up of undesired compounds from analytical samples. For example, the technique has found success in monitoring drinking water by extraction of organics from the water followed by high pressure liquid chromatography separation and mass spectrometry (MS) detection to determine the identity and concentration of pollutants. Proteins and nucleic acid materials are frequently isolated from biological samples by passing them through a packed column and cartridge containing a solid phase where the molecules of interest are adsorbed. After the sample has passed through the column and the sample molecules have been adsorbed, a solvent is used to desorb the molecules of interest and form a concentrated solution. It is particularly important to be able to purify and concentrate non-polynucleotide biomolecules such as polypeptides and polysaccharides, since these molecules are not amenable to the types of amplification techniques routinely used with nucleic acids.

Proteomics has recently been recognized as the comprehensive identification and the analysis of proteins within cells. The identification and analysis of proteins could potentially lead to technologies that could artificially control mechanisms of cell proliferation differentiation, growth and aging. Information obtained from the analysis of proteins is particularly advantageous compared to the analysis of deoxyribonucleotic acid (DNA) because it is possible to gain information regarding post-translational modifications (PTMs).

A major challenge for proteomics is the study of low-abundance proteins. Many proteins and peptides are only expressed at extremely low levels, and in the presence of a vast excess of contaminating proteins and other cellular constituents. In some eukaryotic cells, the amounts of the most abundant proteins can be $10^6$-fold greater than those of the low-abundant proteins. Many important classes of proteins (that may be important drug targets) such as transcription factors, protein kinases, and regulatory proteins are low-copy proteins. These low-copy proteins will not be observed in the analysis of crude cell lysates without some prior purification. Therefore, new methods must be devised for the sub-proteome isolation.

Functional proteome characterization involves the challenging task of identifying species of interest from among many thousands of proteins, each potentially altered by hundreds of possible post-translational modifications. Additionally, the living organisms often exhibit large dynamic range of protein expression levels, ranging from estimated values of $10^4$ in yeast to $10^9$-$10^{12}$ in plasma. As a result of this extreme complexity, proteomics studies often use various fractionation methodologies to focus on only a subset of the overall protein complement. For example, numerous fractionation schemes based on the presence of a particular chemical moiety such as native amino acid side-chain functionality or biologically important PTMs have been described. Often, these affinity methods are specific for a particular functionality, such as immobilized metal affinity chromatography for the enrichment of phosphorylated peptides or various lectins for the enrichment of specific glycosylated species. Any viable proteomics fractionation and pre-concentration methodology must enable both the efficient isolation of a desired subset from the remainder of the sample, as well as the subsequent efficient recovery and analysis of that subset. In addition the method has to be capable of maintaining the protein functionality i.e. the enzyme activity. The developed methods must be easily integrated into the miniaturized systems.

It is often necessary to purify and concentrate a protein sample of interest prior to performing analytical techniques such mass spectrometry, surface plasmon resonance (SPR), nuclear magnetic resonance (NMR), X-ray crystallography and the like. These techniques typically only require a small volume of sample, but it must be presented at a sufficiently high concentration and interfering contaminants should be removed. Hence, there is a need for sample preparation methods that permit the manipulation and processing of small sample volumes with minimal sample loss.

Methods and reagents for performing solid phase extractions in open channels, such as open capillaries, are described in co-pending U.S. patent application Ser. No. 10/434,713. The instant disclosure follows up on that application, providing in some instances more specific and detailed teaching for performing open channel solid phase extractions. These methods, and the related devices and reagents, will be of particular interest to the life scientist, since they provide a powerful technology for purifying, concentrating and analyzing biomolecules and other analytes of interest. However, the methods, devices and reagents are not limited to use in the biological sciences, and can find wide application in a variety of preparative and analytical contexts.

BRIEF DESCRIPTION OF THE FIGURES

FIGS. 7A-J depict a section of a multiplexed capillary extraction apparatus in various stages of the extraction process.

FIG. 9A is a scanning electron micrograph and FIG. 9B is a schematic diagram of the capillary coating synthesized in Example 20.

FIG. 12A shows a. MALDI-TOF of a myoglobin tryptic digest spiked with two synthetic phosphopeptides.

DESCRIPTION OF SPECIFIC EMBODIMENTS OF THE INVENTION

Figure 1:
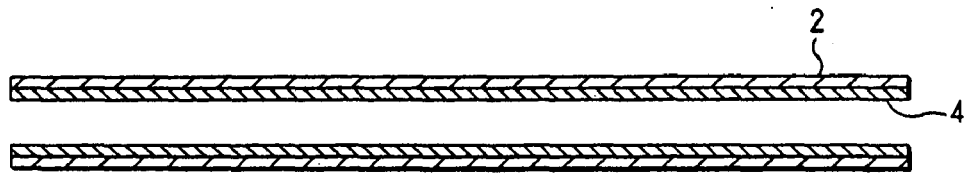
FIGS. 1-4 are schematic drawings exemplifying the operation of an extraction channel.

In accordance with the present invention there may be employed conventional chemistry, biological and analytical techniques within the skill of the art. Such techniques are explained fully in the literature. See, e.g., Antibody Purification Handbook, Amersham Biosciences, Edition AB, 18-1037-46 (2002); Protein Purification Handbook, Amersham Biosciences, Edition AC, 18-1132-29 (2001); Affinity Chromatography Principles and Methods, Amersham Pharmacia Biotech, Edition AC, 18-1022-29 (2001); The Recombinant Protein Handbook, Amersham Pharmacia Biotech, Edition AB, 18-1142-75 (2002); and Protein Purification: Principles, High Resolution Methods, and Applications, Jan-Christen Janson (Editor), Lars G. Ryden (Editor), Wiley, John & Sons, Incorporated (1989); Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 394 (1991); F. Dorwald ORGANIC SYNTHESIS ON SOLID PHASE, Wiley VCH Verlag Gmbh, Weinheim 2002.

The present invention expands upon and extends technology described in U.S. patent application Ser. Nos. 10/434,713 and 10/866,283, both of which are incorporated by reference herein in their entirety.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a molecule" includes a plurality of such molecules and reference to "the detection method" includes reference to one or more detection methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The subject invention pertains to solid phase extraction channels, and methods of using the same for extracting an analyte from solution. In some embodiments these extraction channels are open, that is, they are not packed with resin or other forms of chromatographic beads used in conventional chromatography. Rather, the channel is open and the extraction phase consists of an extraction surface bound either directly or non-directly to the channel surface. The extraction process involves flowing solvent, such as sample solvent, desorption solvent, and optionally a wash solvent, through the open channel, or some portion of the channel. In some embodiments, the open channel is a capillary, i.e., an extraction capillary.

In certain embodiments, the extraction surface covers the entire inner periphery of the extraction channel, as opposed to on just one face of the channel. Thus, even if only some section of the entire length of the capillary is coated with the extraction surface, in that section substantially the entire periphery is covered with the extraction surface. This is to be distinguished from, e.g., a channel in a microfluidic chip or device that has an extraction surface only on one face of the channel.

Methods of the invention typically involve adsorbing an analyte of interest from a sample solution onto the extraction surface of a solid-phase extraction channel, substantially evacuating the sample solution while leaving the adsorbed analyte bound to the extraction surface, and eluting the analyte from the channel in a desorption solution. The desorbed analyte can be collected, and is typically analyzed by any of a number of techniques, some of which are described in more detail below. In some embodiments the extraction surface is washed prior to elution. The extraction process generally results in the enrichment, concentration, and/or purification of an analyte or analytes of interest.

In conventional packed columns there are typically regions (i.e., volumes) that are not swept by solvent passing through the column, which results in sample loss. One advantage of the use of open channels as opposed to conventional packed columns is that unswept volumes can be substantially minimized or eliminated, thus dramatically minimizing or eliminating sample losses associated with such unswept volumes. Minimal unswept volumes allow the introduction, control and collection of defined volumes of liquid that can contain the analyte of interest. The tube or capillary channel must have the property of allowing movement and removal of liquid. In this respect, the tube could contain secondary structures, including roughness and protrusions or even beads or monolith structure as long as the channels that are formed in the secondary structure do not result in unswept volumes that substantially impact performance. A reference (Ronald Majors, 2002 Pittsburgh Conference, Part I, LC/GC Europe, April 2002, pp 2-15) gives details on encapsulated and monolith structures.

Certain embodiments of the invention are particularly suited to the processing of biological samples, where the analyte of interest is a biomolecule. Of particular relevance are biological macromolecules such as polypeptides, polynucleotides, and polysaccharides, or large complexes containing one or more of these moieties.

Because of the nature of the flow path in an open channel of the invention, it is possible to capture, purify and concentrate molecules or groups of molecules that have a relatively large structure compared even to a protein. An extraction channel with the appropriate binding functionality on the surface can bind and extract these structure without problems such as shearing or (frit or backed bed) filtration, that can occur with conventional extraction columns. Care does have to be taken when introducing the solution to the capillary channel or when flowing solutions through the capillary channel so that the structure is not sheared. Slower flow rates may be necessary. Examples of large structures that can be extracted are protein complexes, viruses and even whole cells that can be captured by a specific surface group.

Extraction Methods

In various embodiments, the subject invention provides methods for using solid-phase extraction channels (such as capillaries) to extract, purify, process and/or concentrate an analyte or analtyes of interest. Non-limiting examples of analytes are proteins, carbohydrates, lipids, nucleic acids, nucleic acid-protein complexes, peptides, polypeptides, metabolites, pathway intermediates and products, and small molecules. The invention is particularly suited for the preparation of biomolecule analytes, especially biological macromolecules, including biomolecule complexes. Because of the nature of the capillaries, which are not as susceptible to clogging, unswept dead volumes or sample loss as conventional packed chromatography columns, they can be used for processing very large biological complexes, including large multiprotein complexes such as ribosomes, transcription complexes, proteasomes, etc., as well a organelles, membranes, viruses and whole cells.

In general, the methods involve introducing a sample solution containing the analyte of interest into the extraction channel in a manner that permits the analyte to interact with and adsorb to the extraction surface. The sample solution enters the channel through one end, and passes through the channel or some portion of the entire length of the channel, eventually exiting the channel through either the same end of the channel or out the other end. Introduction of the sample solution into the channel can be accomplished by any of a number of techniques for driving or drawing liquid through a channel. Examples would include use of a pump (e.g., a syringe, pressurized container, centrifugal pump, electrokinetic pump, or an induction based fluidics pump), gravity, centrifugal force, capillary action, or gas pressure to move fluid through the capillary. The sample solution is preferably moved through the channel at a flow rate that allows for adequate contact time between the sample and extraction surface. The sample solution can be passed through the capillary more than one time, either by circulating the solution through the channel in the same direction two or more times, or by passing the sample back and forth through the channel two or more times (e.g., by oscillating a plug or series of plugs of desorption solution in the channel). In some embodiments it is important that the pump be able to pump air, thus allowing for liquid to be blown out of the channel. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation in the channel will vary depending on the step in the extraction procedure, the enrichment of the biomolecule desired, and the dimensions of the capillary. For example, for a capillary with dimensions of 200 µm id and 1 m in length, the internal volume is approximately 33 µL. A liquid slug of 10% of the capillary volume represents a 3.3 µL volume and a 10 cm length. Movement of the slug to within 2% of each end of the capillary means the slug should be within 4 cm of each end. Accuracy of dispensing the slug depends on the volume to be dispensed. Expelling the entire slug requires less accuracy than expelling only part of the slug. If 10% of the slug is expelled then, the slug must be moved to the end of the capillary (within a few mm) and then 1 cm of the slug is expelled or deposited to the target.

Thus, for example, in one embodiment an end of an extraction channel is attached to a syringe pump and the other end is positioned in a sample solution. The syringe plunger is pulled up to draw the sample solution into and through the channel. The sample can be drawn through the entire length of the channel, and optionally into the chamber of the syringe. The ability to draw liquid into the syringe is particularly relevant when the sample volume exceeds the volume of the channel. Once the entire volume of sample to be processed has been drawn into the channel and/or syringe chamber, and optionally after some incubation period where the sample is allowed to set in the syringe and/or channel, the syringe plunger is pushed down, driving the sample solution back through the channel and out through the same end from which it entered. At this point, the sample has passed through the capillary twice, once in each direction. If desired, for example to increase interaction of analyte with extraction surface and to increase the amount of adsorbed analyte, the drawing in and driving out of the sample solution can be repeated e.g., four times, which would result in a total of 8 passes of the solution through the channel. The drawing in and driving out of the sample solution can also be accomplished by other means, e.g., through a vacuum or pressure chamber.

In some cases it is desirable to hydrate, solvate and/or otherwise condition the extraction channel prior to use. The particular protocol will depend upon the nature of the extraction chemistry. Capillary conditioning is exemplified in the Examples appended hereto.

In some embodiments of the invention, after the sample solution has been exposed to the extraction surface and analyte adsorbed, the sample solution is substantially eliminated from the channel. For example, after the sample solution has been drawn through the channel one or more times it is substantially drawn or driven out of the capillary and replaced by either gas or liquid. For example, continuing with the illustrative embodiment described above, the syringe pump can be used to pump the sample solution out through the end through which it had entered. While it is not always necessary to remove the sample solution from the capillary prior to elution, it is usually desirable because it reduces the presence of unwanted contaminating species from the sample solution that end up with the eluted protein, and also facilitates control of the desorption solution in the channel. In some embodiments of the invention, residual sample solution can be more thoroughly removed from the channel by blowing air or gas through the channel. However, this is usually not necessary since typically a wash step is performed between the sample loading and elution steps in the purification.

The sample solution can be any solution containing an analyte or analytes of interest. Because sample passes through an open channel, the extraction capillaries of the invention are relatively tolerant of particulate matter in the sample solution compared to packed bed extraction columns. Still, it is often useful to clarify a crude sample prior to introduction into the channel, e.g., by centrifugation or filtration. Examples of sample solutions would include cell lysates, serum-free hybridism growth medium, tissue or organ extracts, biological fluids, cell-free translation or transcription reactions, or organic synthesis reaction mixtures. In some cases the sample solution is the analyte in a solvent used to dissolve or extract the analyte from a biological or chemical sample. The solvent should be sufficiently weak to ensure sufficient adsorption of the analyte to the channel's extraction surface. Ideally, the adsorption is quantitative, near quantitative, or at least involves a substantial amount of the analyte. Nevertheless, the process can still be very useful where only some smaller fraction of the total analyte is adsorbed, depending upon the nature of the analyte, the amount of starting material, and the purpose for which the analyte is being processed.

In some embodiments of the invention, the channel is washed after the sample loading and prior to analyte elution. Although this step is optional, it is often desirable since it can remove contaminants from the extraction surface and thus improve the purity of the eluted product. In one embodiment, the wash solution is drawn through the capillary using the same or a different syringe pump as was used to draw sample solution through the capillary. A wash solution (i.e., a rinse solution) should be employed that will wash contaminants (e.g., proteins that are not specifically bound to an affinity group) from the extraction surface while, to the extent possible, allowing the adsorbed analyte to remain adsorbed to the extraction surface. The wash solution should also be one that does not damage the analyte molecule or extraction surface. In some cases, such as where the analyte is a protein or protein complex, a wash solution is used that does not denature or degrade the analyte, facilitating recovery of functional native protein.

The exact nature and composition of the wash solution can vary, and will to some extent be determined by the nature of the analyte, the extraction surface, and the nature of the adsorption. Ideally, a wash solution will be able to solubilize and/or wash contaminants from the capillary and extraction surface while leaving the adsorbed analyte bound. In practice, there might need to be some trade-off between the ability to remove all contaminants versus the ability to retain all analyte, which translates into a trade-off between sample purity and sample recovery. That is, a very stringent wash solution capable of effectively removing all contaminants will often also remove some analyte, whereas a wash solution that does not remove any analyte will often not be as effective in removing unwanted contaminants. To some extent, selection of the wash solution will depend upon the relative importance of sample purity vs. sample recovery.

Prior to elution of the adsorbed analyte from an extraction capillary, it is often desirable to purge any residual solution from the capillary, i.e., to displace residual solution from the capillary. This can be accomplished by passing a gas such as air or nitrogen through the capillary. More effective purging can in some cases be achieved by blowing gas through the capillary for some amount of time sufficient to achieve the desired extent of purging. This residual solution will typically be the wash solution if such is used or the sample solution if there is no wash step. In some embodiments a purge step can be performed both before the wash step (e.g., to remove residual sample solution) and after the wash step, but purging is normally not necessary prior to the wash step. In certain embodiments, multiple wash steps are employed. For example, in some embodiments an extra $D_2O$ wash is employed prior to elution in a deuterated solvent. Purging can be effected after such extra steps if desired.

While it is often not possible, or even desirable, to remove all trace solution from the capillary and its surface, the objective is to remove enough of the solution so that it is not possible for short segments of solution to form in the capillary during the elution process. Thus, in one embodiment the objective is to substantially remove all bulk liquid from the capillary, without dehydrating or desolvating the extraction surface. The extraction surface and any bound analyte, e.g., a bound protein, remain hydrated and in their native state, while any bulk solution that could detract from the ultimate purity and concentration of the eluted analyte are removed. This can be accomplished by blowing a gas through the capillary for a suitable period of time. The amount of time will vary depending upon the nature of the extraction surface, the nature of the solution in the capillary, etc. An example of a typical purge protocol would involve application of 50-60 psi gas (e.g., nitrogen or helium) to the capillary for several seconds to several minutes. The extraction surface of the capillary will not be dried by the purging, but rather will remain hydrated or solvated, so long as the drying does not go on for too long, or, for example, at too high of a temperature. In other embodiments, the purging is more complete, resulting in partial or even substantial dehydration or desolvation of the extraction surface and/or analyte. Depending upon the nature of the analyte, the extraction surface, and the intended analytical technique, substantial drying is in some cases not a problem, e.g., in some cases where the analyte is a nucleic acid.

The extent of displacement of fluid from the capillary can vary depending upon the requirements of the particular extraction protocol and system used. For example, in various embodiments of the invention, as a result of the purge step the extraction channel is at least 20% free of bulk liquid, or at least 30% free of bulk liquid, or at least 40% free of bulk liquid, or at least 50% free of bulk liquid, or at least 60% free of bulk liquid, or at least 70% free of bulk liquid, or at least 80% free of bulk liquid, or at least 90% free of bulk liquid, or at least 95% free of bulk liquid, or at least 98% free of bulk liquid, or at least 95% free of bulk liquid, or substantially free of bulk liquid.

Thus, in one embodiment the invention provides an extraction channel (e.g., a capillary) containing a bound analyte that is substantially free of bulk liquid. In particular, the bound analyte can be a biomolecule, such as a biological macromolecule (e.g., a polypeptide, a polynucleotide, or a polysaccharide). The biomolecule can be part of a larger structure, such as a biomolecule complex, an organelle, a virus, a cell or a membrane. In certain embodiments the analyte is a protein or protein-containing complex. While substantially free of bulk solution, the analyte and/or extraction surface can be fully hydrated. In the case of a biomolecule such as a protein, this hydration can stabilize the binding interaction and the structural and functional integrity of the molecule. An extraction capillary containing a bound, hydrated biomolecule but otherwise substantially free of bulk water can be prepared by purging the capillary for a suitable amount of time. It can be important not to over-dry the capillary, since this could cause the denaturation of a bound biomolecule, and could prevent or hinder recovery of the functional molecule. Under the proper conditions, the capillary and bound analyte will be stable for a substantial period of time, particularly if the proper hydration is maintained. The capillary is useful for providing a pure, concentrated sample of the adsorbed analyte, which can be recovered by using the appropriate elution protocol as described herein. In some embodiments the extraction surface is 3-dimensional.

In another embodiment, the invention provides an extraction channel that is substantially free of liquid and contains a bound biomolecule analyte, and wherein the extraction surface and/or analyte are partially or substantially dehydrated or desolvated. In some embodiments the extraction surface is 3-dimensional and/or the biomolecule is a nucleic acid, or some other molecule that is relatively stable to dehydration.

Finally, after any optional wash and/or purge steps have been performed, the adsorbed analyte is eluted from the capillary via desorption into a desorption solution. The desorption solution can be drawn or driven in and out of the capillary by the same or different mechanism as used for the sample solution and/or wash solution. Thus, in one embodiment a syringe attached to one end of the capillary is used to pull desorption solution through the other end of the capillary and to eject it from the same. The amount of desorption solution used will determine the ultimate concentration of the eluted analyte. While a sufficient amount of desorption solution must be used to achieve satisfactory recovery, it is generally advisable to use as small amount as practical in order to achieve a higher analyte concentration.

The term "liquid segment" is defined herein as a block of liquid in a channel, bounded at each end by a block of liquid or gas. When the liquid segment is substantially immiscible with the liquid or gas on either side of it, it is sometimes referred to as a slug, e.g., a slug of desorption solution. Substantially immiscible implies that constituents of the slug will not mix with any liquid or gas by which it is bound. Where a slug of desorption solution is bounded by gas, for example, the volume and analyte concentration of the slug is well-defined. This is in contrast to the case in many conventional chromatographic approaches, where eluted analyte can diffuse in the elution solvent, leading to, for example, broadening of chromatographic peaks in a chromatogram. Thus, in some embodiments the invention allows for the preparation of a small eluted sample of defined volume and substantially uniform concentration, as determined by the volume of the liquid segment used.

In some embodiments, the amount of desorption solution is greater than the volume of the channel. However, in others, an amount of desorption solution is used that is equal to or less than the volume of the extraction capillary. In the context of open channel solid phase extraction, the term "tube enrichment factor," or "TEF," is defined as the ratio of the volume of an extraction channel to the volume of a liquid segment of desorption solvent used to desorb an analyte from the extraction surface. Desorption of an extracted analyte into a volume of desorption solvent that is less than the volume of the channel, e.g., less than the volume of an extraction capillary, will result in a TEF of greater than one. For example, if analyte is extracted from a sample onto the extraction surface of an extraction capillary having a total volume of 1 µL, and subsequently desorbed into a 0.1 µL slug of desorption solution, the TEF of the extraction is 1 µL/0.1 µL, or 10. In some embodiments of the invention the ability to blow out liquid from an extraction capillary with gas and use a small slug of desorption solvent results in a positive TEF, which can contribute to concentration and enrichment of the analyte. In some embodiments the instant invention provides methods and systems for performing extractions with TEFs greater than one, e.g., TEFs of up to 2, 5, 10, 20, 50, 100, 500, 1000 or greater can be achieved. The resulting sample concentration and/or enrichment can be particularly important with low abundance samples and/or for use with analytical techniques requiring small volumes of sample.

TEF is a component of the total enrichment of the sample. The total enrichment factor of the sample can be increased even further by processing a volume of sample solution that exceeds the volume of the channel. In the context of open channel solid phase extraction, the term "enrichment factor" (or "total enrichment factor") is defined as the ratio of the volume of a sample containing an analyte that is passed through (i.e., loaded onto or processed by) an extraction channel to the volume of liquid segment of desorption solvent used to desorb an analyte from the extraction surface. For example, if a 100 µL sample containing an analyte is passed through a 1 µL extraction capillary, and the extracted analyte is then eluted with 0.1 µL of desorption solvent, the enrichment factor for the extraction is 100 µL/0.1 µL, or 1000. Thus, the enrichment factor represents a theoretical upper limit for the degree of concentration of the analyte that would be achieved assuming 100% efficiency of analyte adsorption from sample to the extraction surface and of the subsequent desorption into the desorption solvent. The enrichment factor of an extraction can be increased by passing more sample solution through an extraction channel and/or by increasing TEF. The high enrichment factors that can be obtained in many embodiments of this invention are particularly useful when attempting to purify and concentrate a low abundance biomolecule from a relatively large volume of sample solution. In a sense, the ability to concentrate a low abundance protein is analogous to the ability of PCR to amplify a low abundance polynucleotide, and can allow for detection and analysis of proteins than might not otherwise be detectable. Depending upon the volume of sample solution processed and the TEF employed, in certain embodiments of the invention enrichment factors of 10, $10^2$, $10^3$, $10^4$, $10^5$ or higher can be achieved.

In some embodiments of the invention, very small volumes of desorption solvent are employed. For example, some embodiments of the invention are characterized by the use of volumes of desorption solvent that fall within a range having a lower limit of about 10 pL, 100 pL, 1 nL, 10 nL, 100 nL, 1 µL or 10 µL; and an upper limit of about 1 µL, 5 µL, 10 µL, 20 µL, 30 µL, 40 µL, 60 µL, 80 µL, 100 µL or 500 µL. Examples would include ranges of 10 pL to 500 µL, 100 pL to 500 µL, 1 nL to 500 µL, 10 nL to 500 µL, 100 nL to 500 µL, 1 µL to 500 µL, 10 µL to 500 µL, 20 µL to 500 µL, 10 pL to 100 µL, 100 pL to 100 µL, 1 nL to 100 µL, 10 nL to 100 µL, 100 nL to 100 µL, 1 µL to 100 µL, 10 L to 100 µL, 20 µL to 100 µL, 10 pL to 20 µL, 100 pL to 20 µL, 1 nL to 20 µL, 10 nL to 20 µL, 100 nL to 20 µL, 1 µL to 20 µL, 10 µL to 20 µL. An advantage of some embodiments of the invention is the ability to collect purified sample in a small, well defined volume of desorption solvent. The desorption solvent can comprise a plug of liquid bounded at one or both ends by gas, or alternatively, by an immiscible liquid.

In another aspect, the invention provides methods of collecting very small fractions of desorbed sample, which might constitute the entire volume of desorption solution used or some fraction thereof. For example, some embodiments of the invention are characterized by the collection of fractions of desorbed sample having volumes that fall within a range having a lower limit of about 10 pL, 100 pL, 1 nL, 10 nL, 100 nL, 1 µL or 10 µL; and an upper limit of about 1 µL, 5 µL, 10 µL, 20 µL, 30 µL, 40 µL, 60 µL, 80 µL, 100 µL or 500 µL. Examples would include ranges of 10 pL to 500 µL, 100 pL to 500 µL, 1 nL to 500 µL, 10 nL to 500 µL, 100 nL to 500 µL, 1 µL to 500 µL, 10 µL to 500 µL, 20 µL to 500 µL, 10 pL to 100 µL, 100 pL to 100 µL, 1 nL to 100 µL, 10 nL to 100 µL, 100 nL to 100 µL, 1 µL to 100 µL, 10 µL to 100 µL, 20 µL to 100 µL, 10 pL to 20 µL, 100 pL to 20 µL, 1 nL to 20 µL, 10 nL to 20 µL, 100 nL to 20 µL, 1 µL to 20 µL, 10 µL to 20 µL. For example, in some embodiments very small volumes of the desorption solvent are spotted or arrayed on a chip, microwell plate, or other target, as described in more detail elsewhere herein.

While many of the extraction devices of the invention are capable of providing purified analyte in a very small volume of liquid, they are also able (in many cases) to process relatively large original sample volumes, resulting in high enrichment factors. For example, solution volumes of 100 µL to 500 µL, 100 µL to 1 mL, 100 µL to 10 mL, 100 µL to 100 mL, or 100 µL to 1000 mL can be processed in various embodiments of the invention.

It is possible to repeatedly expose the sample, wash and desorption solvent to the extraction surface (e.g., by simply flowing it back and forth through the channel). In the case of sample, this can mean greater extraction efficiencies and hence greater recoveries. In the case of desorption solvent, this can translate into dramatically reduced desorption volume, resulting in a more enriched desorbed sample. Concentrations of the sample can be increased by using only a small slug of desorbing solvent that passes back and forth over the stationary phase before it is deposited from the channel to the target.

The flow rate for the desorption solution should be slow enough that the integrity of the plug is not disturbed. When desorbing the analyte, it can be beneficial to allow the desorption solution to incubate in the capillary (or a section of the capillary when using a small slug of desorption solution) for a period of time, e.g., for one or several minutes.

In general, sensitivity and selectivity can be improved by increasing the number of passes of sample solution and/or desorption solution through the capillary, and/or by decreasing flow rate. Both result in longer exposure of the analyte to the extraction surface. However, both will also result in the extraction process taking longer, so there can be a trade-off of lower throughput for the improved sensitivity and selectivity. Depending upon the relative importance of sensitivity and selectivity vs. throughput, the appropriate number of passages and flow rate can be selected.

For example, in some embodiments the invention provides a method of extracting an analyte from a solution comprising the steps of: passing a solution containing an analyte through an extraction channel having a solid phase extraction surface, whereby analyte adsorbs to the extraction surface of said extraction channel; and eluting the analyte by passing a desorption solution through the channel, wherein the method includes a step wherein a multiple-pass solution is passed through at least some substantial portion of the extraction channel at least twice. The term "multiple-pass solution" refers to a solution that is passed through the extraction channel, or at least some portion of the extraction channel, two or more times. The multiple-pass solution can be any solution used in connection with an extraction process, e.g., a sample solution containing an analyte, a wash solution or a desorption solution.

In some embodiments, the multiple-pass solution is passed through at least some substantial portion of the extraction channel at least twice, and in certain embodiments it can be passed through at least four times, at least eight times, at least twelve times, or even more, in order to achieve the desired effect. Multiple passages can be achieved by passing the solution multiple times through the capillary in the same direction, or can be achieved by reversing the flow of solution so that it flows back and forth through the capillary.

In some embodiments of the invention, the substantial portion of the extraction channel through which the multiple-pass solution is passed comprises at least 50% of the extraction channel, or at least 70% of the extraction channel, or at least 80% of the extraction channel, or at least 90% of the extraction channel, or at least 95% of the extraction channel, or at least 99% of the extraction channel, or substantially the entire length of the extraction channel.

While for purposes of illustration much of the foregoing description has focused on the case where solutions enter and leave the capillary through the same opening, other embodiments can also be employed and are encompassed within the scope of the subject invention. For example, in some embodiments one or more of the solutions enter the capillary from one end and exit through the other, as is normally the case with conventional column chromatography.

The sample can be drawn into the channel or pumped through the channel. The sample may be moved back and forth in the channel as many times as is necessary to achieve the desired desorption. Small particulates and air bubbles typically have little or no effect on performance, a remarkable distinction from previous solid phase extraction systems.

The wash solution and desorption solvent also can be introduced from either end and may be moved back and forth in the channel. They can include combination of a capillary channel and a pump for gas and liquids such as conditioning fluid, sample, wash fluid, and desorption fluid. The pump can be, e.g., a syringe (pressure or vacuum), pressure vessel (vial), or centrifugation device. The pumping force is preferably on the bulk fluid and preferably not due to electroosmotic force; fluid is moved through the capillary channel in a controlled manner. Generally, this means that the volume of liquid acted upon is controlled through positive displacement or movement of a specified volume, timing of the pumping action or through control of the volume of the fluid pumped through the channel. Examples of suitable pumps include syringe or piston, peristaltic, rotary vane, diaphragm, pressurized or vacuum chamber, gravity, centrifugal and centrifugal force, capillary action, piezo-electric, piezo-kinetic and electro-kinetic pumps.

FIGS. 1-4 are schematic drawings of the operation of an open tube extraction channel of this invention. FIG. 1 shows a tubular channel 2, the inner surface of which is coated with a solid phase extraction medium 4. Note that in this drawing the entire inner surface is coated with extraction medium, while in certain embodiments of the invention this might not be the case.

Figure 2:
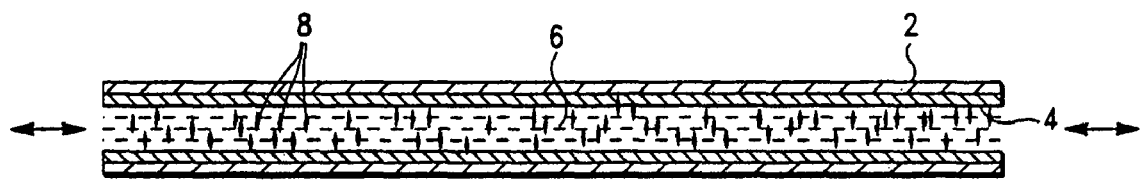

FIG. 2 shows the tubular channel of FIG. 1 as sample 6 is passed through the capillary, and the affinity binding reagent 4 reacts with the sample 6 and adsorbs (i.e., extracts) a protein of interest 8 from the sample. Contaminants that were present in the sample are washed away with an optional wash solution (not shown).

Figure 3:

FIG. 3 shows the tubular channel of FIG. 2 after the liquid has been displaced from the channel 2 with a gas such as air, nitrogen or helium.

Figure 4:
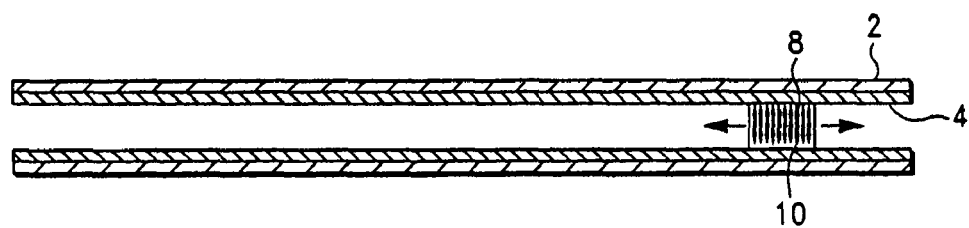

FIG. 4 shows the tubular channel of FIG. 3 as a segment of desorption solvent 10 is passed through the tube 2 to desorb and recover the protein 8. The segment can optionally be passed back and forth through the channel one or more times to improve sample recovery.

As an alternative to the procedure shown in FIG. 4, a desorption fluid can be pumped through the capillary channel in one direction, the front boundary of the fluid desorbing and collecting the protein. The protein desorbs quickly from the wall, and will travel in the front boundary segment of the desorption solvent as the solvent travels down the tube.

The analyte eluted in the solvent segment 10 can be directed and deposited into or onto the target, i.e. a collection vial, a tube, a surface, or an instrument.

After extraction, the residual liquid can be expelled from the tube with a gas such as air to minimize the wash step.

In some embodiments, a series of two or more plugs of desorption solvent separated by air bubbles are employed, i.e., a "sandwich" elution.

Solvents

Extractions of the invention typically involve the loading of analyte in a sample solution, an optional wash with a rinse solution, and elution of the analyte into a desorption solution. The nature of these solutions will now be described in greater detail.

With regard to the sample solution, it typically consists of the analyte dissolved in a solvent in which the analyte is soluble, and in which the analyte will bind to the extraction surface. Preferably, the binding is strong, resulting in the binding of a substantial portion of the analyte, and optimally substantially all of the analyte will be bound under the loading protocol used in the procedure. The solvent should also be gentle, so that the native structure and function of the analyte is retained upon desorption from the extraction surface. Typically, in the case where the analyte is a biomolecule, the solvent is an aqueous solution, typically containing a buffer, salt, and/or surfactants to solubilize and stabilize the biomolecule. Examples of sample solutions include cell lysates, hybridoma growth medium, cell-free translation or transcription reaction mixtures, extracts from tissues, organs, or biological samples, and extracts derived from biological fluids.

It is important that the sample solvent not only solubilize the analyte, but also that it is compatible with binding to the extraction phase. For example, where the extraction phase is based on ion exchange, the ionic strength of the sample solution should be buffered to an appropriate pH such that the charge of the analyte is opposite that of the immobilized ion, and the ionic strength should be relatively low to promote the ionic interaction. In the case of a normal phase extraction, the sample loading solvent should be non-polar, e.g., hexane, toluene, or the like. Depending upon the nature of the sample and extraction process, other constituents might be beneficial, e.g., reducing agents, detergents, stabilizers, denaturants, chelators, metals, etc.

A wash solution, if used, should be selected such that it will remove non-desired contaminants with minimal loss or damage to the bound analyte. The properties of the wash solution are typically intermediate between that of the sample and desorption solutions.

Desorption solvent can be introduced as either a stream or a plug of solvent. If a plug of solvent is used, a buffer plug of solvent can follow the desorption plug so that when the sample is deposited on the target, a buffer is also deposited to give the deposited sample a proper pH. An example of this is desorption from a protein G surface of IgG antibody which has been extracted from a hybridoma solution. In this example, 10 mM phosphoric acid plug at pH 2.5 is used to desorb the IgG from the tube. A 100 mM phosphate buffer plug at pH 7.5 follows the desorption solvent plug to bring the deposited solution to neutral pH. The deposited material can then be analyzed, e.g., by deposition on an SPR chip.

The desorption solvent should be just strong enough to quantitatively desorb the analyte while leaving strongly bound interfering materials behind. The solvents are chosen to be compatible with the analyte and the ultimate detection method. Generally, the solvents used are known conventional solvents. Typical solvents from which a suitable solvent can be selected include methylene chloride, acetonitrile (with or without small amounts of basic or acidic modifiers), methanol (containing larger amount of modifier, e.g. acetic acid or triethylamine, or mixtures of water with either methanol or acetonitrile), ethyl acetate, chloroform, hexane, isopropanol, acetone, alkaline buffer, high ionic strength buffer, acidic buffer, strong acids, strong bases, organic mixtures with acids/bases, acidic or basic methanol, tetrahydrofuran and water. The desorption solvent may be different miscibility than the sorption solvent.

In the case where the extraction involves binding of analyte to a specific cognate ligand molecule, e.g., an immobilized metal, the desorption solvent can contain a molecule that will interfere with such binding, e.g., imidazole or a metal chelator in the case of the immobilized metal.

Examples of suitable phases for solid phase extraction and desorption solvents are shown in Tables A and B.

TABLE A

| | Normal Phase Extraction | Reverse Phase Extraction | Reverse Phase Ion-Pair Extraction |
|---|---|---|---|
| Typical solvent polarity range | Low to medium | High to medium | High to medium |
| Typical sample loading solvent | Hexane, toluene, $CH_2Cl_2$ | $H_2O$, buffers | $H_2O$, buffers, ion-pairing reagent |
| Typical desorption solvent | Ethyl acetate, acetone, | $H_2O/CH_3OH$, $H_2O/CH_3CN$ (Methanol, | $H_2O/CH_3OH$, ion-pairing reagent $H_2O/CH_3CN$, ion- |

TABLE A-continued

|  | Normal Phase Extraction | Reverse Phase Extraction | Reverse Phase Ion-Pair Extraction |
|---|---|---|---|
|  | CH$_3$CN (Acetone, acetonitrile, isopropanol, methanol, water, buffers) | chloroform, acidic methanol, basic methanol, tetrahydrofuran, acetonitrile, acetone, ethyl acetate,) | pairing reagent (Methanol, chloroform, acidic methanol, basic methanol, tetrahydrofuran, acetonitrile, acetone, ethyl acetate) |
| Sample elution selectivity | Least polar sample components first | Most polar sample components first | Most polar sample components first |
| Solvent change required to desorb | Increase solvent polarity | Decrease solvent polarity | Decrease solvent polarity |

TABLE B

|  | Ion Exchange Extraction | Hydrophobic Interaction Extraction | Affinity Phase Extraction |
|---|---|---|---|
| Typical solvent polarity range | High | High | High |
| Typical sample loading solvent | H$_2$O, buffers | H$_2$O, high salt | H$_2$O, buffers |
| Typical desorption solvent | Buffers, salt solutions | H$_2$O, low salt | H$_2$O, buffers, pH, competing reagents, heat, solvent polarity |
| Sample elution selectivity | Sample components most weakly ionized first | Sample components most polar first | Non-binding, low-binding, high-binding |
| Solvent change required to desorb | Increase ionic strength or increase retained compounds pH or decrease pH | Decrease ionic strength | Change pH, add competing reagent, change solvent polarity, increase heat |

The Extraction Channel

The subject invention involves the use of solid-phase extraction channels for the extraction of one or more analytes from a sample solution. The term "channel" encompasses but is not limited to the various forms of conventional capillary tubing that are used for applications such as chromatography and capillary electrophoresis, e.g., fused silica capillary tubing. Thus, the term also encompasses other open channels of similar dimensions, having one or more capillary flow passageways, each having an inlet in communication with an outlet. Examples include a capillary tube, a bundle of tubes, a solid block or chip having one or more passageways or flow cells running therethrough, e.g., a microfluidics device such as those associated with BiaCore, Inc. (Piscataway, N.J.), Gyros, Inc. (Uppsala, Sweden), Caliper Technologies, Inc. (Mountain View, Calif.) and the like. The passageways can have linear or non-linear central axes, e.g., they can be coiled, curved or straight. The cross-sectional geometry of the passageway is not critical, so long as it allows the channel to function as an extraction channel. For example, capillary tubes having a round cross-sectional geometry work well and can be purchased from a number of vendors. However, other geometries, such as oval, rectangular or another polygonal shape, or a combination of such shapes, can also be employed.

Whatever the geometry of the channel, the dimensions should be such that analyte is able to effectively diffuse and interact with the extraction surface during the course of the extraction process and fluids can be moved through the channel, e.g., pumped through the channel. In general, the larger the molecular weight of an analyte the slower it will diffuse. Thus, with large biological macromolecules it is desirable that the ratio of channel surface area to channel volume per a length of channel is high enough to allow for effective diffusion of analyte to the surface during the time the sample is in the channel. In general, the greater the ratio of the channel perimeter (or circumference, in the case of a round channel) to the internal cross-sectional area, the greater the transport or diffusion of the analyte from the sample solution to the extraction surface. In the case of a round channel, this simply means that the smaller the internal diameter of the capillary the more effective the transport will be for a given length of capillary and under given conditions of sample volume, flow rates, residence times, etc. Of course, the trade-off for increased interaction with the capillary extraction surface is lower flow capacity with lower channel perimeter and a lower extraction capacity due to less surface area. In addition, if the perimeter (e.g., circumference) is very small there could be problems with clogging due to any particulate matter or the like that might be present in a sample, such as a crude cell lysate. One of skill in the art would be able to readily select an appropriate capillary having dimensions that allow for effective transport of analyte to the extraction surface while maintaining adequate solution flow and extraction capacity.

As an alternative to increasing ratio of extraction surface area to capillary volume, the transport of bulky analyte to the extraction surface can be improved by lengthening the channel, the flow rate through the channel can be increased, the sample can be passed back and forth through the channel multiple times, the sample can be allowed to incubate in the channel for a period of time, and/or the sample solution can be agitated as it flows through the channel (by introducing tortuosity into the flow path, e.g., by coiling the capillary), by introducing beads or other features into the capillary, etc. Note that a feature such as a bead that is introduced into a capillary to modulate flow properties should not be penetrable to the analyte or introduce unswept dead volumes that would be contrary to the free flow of solvent through the open channel. One measure of flow path tortuosity in the context of coiled capillary tubing is the agitation aspect ratio, described in greater detail in U.S. patent application Ser. No. 10/434,713. The AAR is the ratio of the effective tubing diameter divided by the effective curve diameter of the tubing central axis. The lowest possible AAR is 1 for a capillary channel, assuming the tightest curve that can be formed and thinnest possible channel wall. AARs less than 1.75 can be formed for channels with very thin channel walls. The calculation is true for a channel of any diameter. In more common configurations, the AAR can be within the range of 1.75 to 2000 and is optimal from 10 to 100.

In certain embodiments of the invention, at least some portion of the capillary is coiled at a bend radius of less than 3 cms. The term "bend radius" refers to the radius of a bend in the capillary tubing. In the case of a coil, for example, a coil diameter of 2 cms corresponds to a bend radius of 1 cm. In some embodiments, at least some portion of the capillary is coiled at a bend radius falling within one or more of the following ranges: between 0.1 and 3 cms, between 0.2 and 3 cms, between 0.5 and 3 cms, between 1 and 3 cms, between 0.1 and 2 cms, between 0.2 and 2 cms, between 0.5 and 2 cms, between 1 and 2 cms, between 0.1 and 1 cm, between 0.2 and 1 cm, and between 0.5 and 1 cm. The term "bend radius" refers to the radius of a bend in the capillary tubing. In the case of a coil, for example, a coil diameter of 2 cms corresponds to a bend radius of 1 cm. Capillary coiling and bend radius are described in more detail in U.S. patent application Ser. No. 10/733,664, incorporated by reference herein in its entirety.

One measure of the effective surface area of a column is the ratio of surface area to volume for a given length of channel, e.g., the ratio of perimeter to cross-sectional area. For example, in the case of a capillary having an inner diameter of 200 µm, the perimeter (in this case the circumference, assuming that the channel is circular) is $\pi \times 200$ µm, or 628 µm. The cross-sectional area is $\pi \times (100$ µm$)^2$, or 31,400 µm$^2$, and the ratio is 0.2 µm$^{-1}$. For a 5 µm i.d. capillary the ratio is 0.8 µm$^{-1}$, for a 50 µm i.d. capillary the ratio is 0.08 µm$^{-1}$, for a 100 µm i.d. capillary the ratio is 0.04 µm$^{-1}$, for a 500 µm i.d. capillary the ratio is 0.0008 µm$^{-1}$, and for a 1000 µm i.d. capillary the ratio is 0.004 µm$^{-1}$. This illustrates the principle that the narrower the channel, the greater is the effective surface area per volume of the channel. In practice, it is likely that the inner surface of a capillary or other channel is not a smooth circle, so the calculated numbers are only theoretical. Of course, the trade-off for the increase in surface area is the reduced capacity of the smaller volume capillary, and sometimes other problems that are introduced by the use of such small channels.

The same sort of calculation can be performed with non-circular channels to derive the ration of perimeter to cross-sectional area, which is generally a measure of the effective surface area of the channel. For example, a square capillary with inner dimensions of 100 µm×10 µm would have a perimeter of 400 µm (4×100 µm) and a cross-sectional area of 10,000 µm$^2$ ((100 µm)$_2$), so the ratio is 400/10,000=0.04 µm$^{-1}$. In some embodiments of the invention, channels having a ratio perimeter to cross-sectional area in the range of, e.g., 0.001 to 2 µm$^{-1}$, 0.002 to 2 µm$^{-1}$, 0.004 to 2 µm$^{-1}$, 0.008 to 2 µm$^{-1}$, 0.04 to 2 µm$^{-1}$, 0.08 to 2 m$^{-1}$, 0.4 to 2 m$^{-1}$, 0.8 to 2 µm$^{-1}$, 0.001 to 0.8 µm$^{-1}$, 0.002 to 0.8 µm$^{-1}$, 0.004 to 0.8 µm$^{-1}$, 0.008 to 0.8 µm$^{-1}$, 0.04 to 0.8 µm$^{-1}$, 0.001 to 0.04 µm$^{-1}$, 0.002 to 0.04 µm$^{-1}$, 0.004 to 0.04 µm$^{-1}$, or 0.008 to 0.04 µm$^{-1}$.

The inner walls of the channel can be relatively smooth, rough, textured or patterned. In certain embodiments of the invention, the channel walls are relatively non-porous. The inner surface can have irregular structure such as is described by Paul Kenis, et al., (2000) Acc. Chem. Res., 33:84 and Paul Kenis, et al., (1999) Science, 285:83. The tube can contain a monolith structure provided that it has channels for liquid passage. Whatever the internal structure of the capillary, it is important to minimize dead volumes or areas that prevent effective removal of solution from the capillary prior to the desorption step in an extraction process.

The capillary channel may be composed of a number of different materials. These include fused silica, polypropylene, polymethylmethacrylate, polystyrene, (nickel) metal capillary tubing, and carbon nanotubes. Polymeric tubes are available as straight tubing or multihole tubing (Paradigm Optics, Inc., Pullman, Wash.). Functional groups may be needed on the capillary tube surface to perform solid phase extraction. Methods to attach chemical groups to polymers are described in the following organic synthesis texts, and these texts are hereby incorporated by reference herein in their entireties, Jerry March ADVANCED ORGANIC CHEMISTRY, 3rd ed., Wiley Interscience: New York (1985); Herbert House, MODERN SYNTHETIC REACTIONS, 2$^{nd}$ ed., Benjamin/Cummings Publishing Co., California (1972); and James Fritz, et al., ION CHROMATOGRAPHY, 3rd, ed., Wiley-VCH, New York (2002); and ORGANIC SYNTHESIS ON SOLID PHASE, F. Dorwald Wiley VCH Verlag Gmbh, Weinheim 2002. Nickel tubing is available from Valco Instrument, Inc., Houston, Tex.

In some embodiments, the extraction channel is a carbon nanotube. Formation of carbon nanotubes has been described in a number of publications including Kenichiro Koga, et al., Nature, 412:802 (2001). Organic functional groups can be attached to the walls of carbon nanotubes and similar polymer composites. See, e.g., Odegard, G. M. et al., "The effect of chemical functionalization on mechanical properties of nanotube/polymer composites," 44$^{th}$ AIAA/ASME/ASCE/AHS Structures, Structural Dynamics and Materials Conference, 7-10 Apr. 2003, Norfolk, Va. and Chen et al. "Chemical attachment of organic functional groups to single-walled carbon nanotube material," (1998) J. Mater. Res. 13(9):2423-13.

In some embodiments, the extraction channel is a fused silica capillary tubing. As used herein the term "fused silica" refers to silicon dioxide (SiO2) in its amorphous (glassy) state, which is a species of the broader genera of compositions commonly referred to as high quality synthetic glass of nearly pure SiO2. The term "synthetic fused silica" refers to amorphous silicon dioxide that has been produced through chemical deposition rather than refinement of natural ore. This synthetic material is of much higher purity and quality as compare to fused quartz made from natural minerals. Examples of fused silica capillaries relevant to this invention include those produced by Polymicro Technologies, LLC of Phoenix, Ariz. and SGE Inc. of Ringwood, Australia. In some cases, it is beneficial to etch a fused silica capillary (e.g., by treatment with base) prior to derivatization with an extraction surface, as described in U.S. patent application Ser. No. 10/434,713.

When using silica capillary, it can be useful to assay the number of silanol groups, e.g., before, during or after derivatization with an extraction surface. Methods of assaying for silanol groups are described in co-pending U.S. patent application Ser. No. 10/733,685, filed Dec. 10, 2003, incorporated by reference herein in its entirety.

The extraction channels of the invention can be of any diameter so long as they are not too large to function as extraction channels, e.g., in the case of a circular capillary, internal diameters in the range of about 2 to 3000 microns, about 2 to 1000 microns, about 10 to 700 microns, about 25 to 400 microns, or about 100 to 200 microns. For non-circular capillaries or channels, corresponding internal perimeter dimensions are desirable.

The extraction channels of the invention can be characterized in terms of their channel aspect ratio. The "channel aspect ratio" is the ratio of channel length to average channel inner diameter. For example, an extraction capillary having a length of 1 meter and an inner diameter of 100 microns has a channel aspect ratio of about 10,000. The channel aspect ratio of the capillary channels of this invention are typically in the range of from 10 to 1,000,000, e.g., in a range having a lower limit of 10, 100, 1000, 10,000, or 100,000, and an upper limit of 1000, 10,000, 100,000 or 1,000,000.

The volumes of extraction channels can vary depending upon the nature of the analyte, the extraction chemistry, the channel capacity, and the amount of purified analyte required for the particular application. In various embodiments, the volume of the extraction column can be on the order of milliliters, microliters, or nanoliters, e.g., in a range having an upper limit of 1 µL, 10 µL, 100 µL, 1 mL, 10 mL, or 100 mL; and a lower limit of 0.1 nL, 1 nL, 10 nL, 100 nL, 1 µL, 10 µL, 100 µL or 1 mL.

In embodiments of the invention employing capillary tubing, the tubing is beneficially coated with a flexible coating material, typically a polymer or resin. Preferred coating materials include polyimide, silicone, polyacrylate, aluminum or fluoropolymer, especially semiconductor grade polyimide.

Some embodiments of the invention involve the use of a channel having a length of greater than 5 cm, especially in the range of 10 cm to 10 m, 20 cm to 2 m, or 100 cm to 1 m. In other cases the range of capillary lengths is shorter, e.g., having a lower limit of 0.5 cm, 1 cm, 2 cm, 5 cm or 10 cm, and an upper limit of 1 cm, 2 cm, 5 cm, 10 cm, 100 cm, 1 m or 10 m.

In some embodiments of the invention the channel is coiled into a coil comprising multiple turns, e.g., at least 2 turns, at least 5 turns, at least 10 turns, at least 50 turns, at least 100 turns, or even 200 or more turns. In particular, with respect to fused silica capillary tubing the maximum number of turns is in general limited only by the length of capillary used, the design of the device, and the ASR limitations as described herein. Thus in some embodiments the number of coils can reach 1000, 2000, 10,000 or even more. Specific teaching regarding the coiling of capillary tubing is provided in the U.S. patent application Ser. No. 10/733,664, filed Dec. 10, 2003, incorporated by reference herein in its entirety.

Extraction Surfaces

In the subject invention a solid-phase extraction chemistry attached to the inner surface of the capillary is used to extract an analyte of interest from solution. The solid-phase extraction surface can take any of a wide variety of forms. For example, the extraction surface can be selected from, or based on, any of the extraction chemistries used in solid-phase extraction and/or chromatography, e.g., reverse-phase, normal phase, hydrophobic interaction, hydrophilic interaction, ion-exchange or affinity binding. Because the invention is particularly suited to the purification and/or concentration of biomolecules, extraction surfaces capable of adsorbing such molecules are particularly relevant. The extraction surface can be a monolayer, or can take the form of a 3-dimensional extraction matrix, as described in U.S. patent application Ser. No. 10/754,775, incorporated by reference herein in its entirety.

For many applications of the invention it is desirable that the extraction surface bind tightly and specifically to a biomolecule (or class of biomolecules) of interest, especially relatively large biological macromolecules (e.g., polynucleotides, polypeptides and polysaccharides having a MW of greater than about 1000 Da, including, for example, in the range of 1000 to 10,000,000 Da or more, or more typically in the range of 5000 to 500,000 Da). For use in conjunction with biological samples it is desirable that a three-dimensional solid phase extraction surface forms a biocompatible porous surface. The porosity of the surface allows for the penetration of biomolecules such as proteins into the surface, and interaction of the biomolecules with affinity groups present in the surface. In some embodiments the extraction surface is based upon a fluidic, hydrogel-type environment. Such an environment is particularly suited for the extraction and purification of proteins, since it mimics the properties of bulk solution and can help stabilize the protein in its active form, i.e., the conditions are non-denaturing. Depending upon the particular properties of the analyte, non-limiting examples of suitable surface materials for providing a 3-D structure include porous gold, sol gel materials, polymer brushes and dextran surfaces.

A three-dimensional extraction surface layer of the invention typically has a thickness of from a few angstroms to thousands of angstroms. In some embodiments the surface is between 5 to 10,000 angstroms thick, e.g., 5 to 1000 angstroms. The thickness of the surface can be adjusted as desired based on factors including the dimensions of the capillary channel, the nature of the analyte or analytes of interest, the nature of an affinity group or extraction reagent present in the surface, the desired binding capacity, etc.

In some embodiments of the invention the 3-D solid phase extraction surface is a hydrogel formed from a polymer, e.g., a polysaccharide or a swellable organic polymer. The polymer should be compatible with the analyte of interest and with a minimal tendency towards nonspecific interactions. Examples of suitable polysaccharides include agarose, sepharose, dextran, carrageenan, alginic acid, starch, cellulose, or derivatives of these such as, e.g., carboxymethyl derivatives. In particular, polysaccharides of the dextran type which are non-crystalline in character, in contrast to e.g., cellulose, are very suitable for use in the subject invention. Examples of water-swellable organic polymer would include polyvinyl alcohol, polyacrylic acid, acrylate, polyacrylamide, polyethylene glycol, functionalized styrenes, such as amino styrene, and polyamino acids. Exemplary polyamino acids include both poly-D-amino acids and poly-L-amino acids, such as polylysine, polyglutamic acid, polyaspartic acid, co-polymers of lysine and glutamic or aspartic acid, co-polymers of lysine with alanine, tyrosine, phenylalanine, serine, tryptophan, and/or proline.

Desirable functional attributes of the 3-D surface would include that it should have minimal tendency to interact non-specifically with biomolecules, it should be chemically resistant to the media employed, it should be compatible with proteins and other biomolecules and should not interact with any molecules other than those desired. Furthermore, it should be capable of providing for covalent binding of such a large number of affinity groups as is required for a general applicability of this technique to a variety of analytical problems.

For a number of reasons, dextran, dextran-derivatives and dextran-like materials are particularly suited for use as the backbone molecules in the subject 3-D extraction surfaces. The resulting hydrogel layer is highly flexible, largely non-cross linked and typically extends 100-200 nm from coupling surface under physiological buffer conditions. Dextran can be derivatized, e.g., via carboxymethylation or vinylsulfonation, to incorporate additional reactive handles for activation and covalent attachment of affinity groups. Non-limiting examples of coupling chemistries that can be used with these and related backbone molecules include thiol, amine, aldehyde and streptavidin. See, e.g., F. Dorwald ORGANIC SYNTHESIS ON SOLID PHASE, Wiley VCH Verlag Gmbh, Weinheim 2002, Anal. Biochem. (1991) 198 268-277 and Chem Commun. (1990) 1526-28). These chemistries are generally quite robust. One potential disadvantage of dextran is its negative charge, which can result in undesired interactions with charged proteins depending upon the pH and ionic strength of the environment. This factor can typically be dealt by adjusting parameters to minimize any unwanted non-specific interactions.

The polymer used to form the extraction surface can be cross-linked, e.g., cross-linked dextran. The degree of cross-linking can be varied to adjust the porosity and hence accessibility of the extraction surface, particularly to larger molecules such as biological macromolecules. In many instances, however, it will be desirable to employ minimal or no cross-linking, e.g., low cross-linked dextran, to provide improved accessibility into the surface and improved transport properties. This can be important in procedures wherein a small volume of elution solvent are used to achieve a low volume, highly concentrated sample of analyte. While it can be difficult to prepare a polymer-based 3-D extraction surface without the occurrence of some incidental cross-linking, minimal or low crosslinking can be achieved using methods exemplified in this written description. This differs from conventional columns that use more highly cross-linked polymers. In general, the lower the extent of cross-linking the more accessible the extraction surface is to analyte penetration.

In preparing 3-D extraction surfaces on capillary surfaces there is typically greater latitude with regard to the degree of cross-linking permitted relative to the beads used in conventional chromatography. Generally polymer-based beads require a certain degree of cross-linking to maintain their structure, particularly in the presence of the pressure that develops during the chromatographic process. For example, conventional Sepharose chromatography beads require a certain degree of cross-linking in order to prevent bead distortion and collapse due to the flow pressure. The 3-D extraction surfaces of this invention, being present on the surface of an open channel and thus not subject to the same pressures as beads in a packed column, are generally not restricted to any minimum degree of crosslinking. Thus, extractions surface backbones that have no or low degree of cross-linking can be used, resulting in greater accessibility of the extraction surface to analyte, particularly high MW biomolecules. Thus, extraction surfaces comprising a polymer backbone that is, for example, less than 0.1% crosslinked, about 0.1 to 0.5% crosslinked, about 0.5 to 1% crosslinked, about 1 to 2% crosslinked, about 2 to 3% crosslinked, about 3-5% crosslinked, about 5-7% crosslinked, about 7-10% crosslinked, or even greater than 10% crosslinked can be used. The acceptable degree of crosslinking varies depending upon the nature of the polymer backbone (e.g., swellability of the polymer) and the nature of the analyte (e.g., size and structure of a biomolecule, the molecules hydration volume). Because crosslinking is not required, a variety of backbone chemistries may be employed that would not be appropriate for use in a conventional chromatography bead.

In some embodiments of the invention, the interior of the 3-D extraction surface is accessible to analyte, such that analyte molecules are able to penetrate and adsorb to the surface in 3-dimensions. In particular, some embodiments are accessible to relatively large biological macromolecules, e.g., polynucleotides, polypeptides and polysaccharides having a MW of greater than about 1000 Da, including, for example, in the range of 1000 to 10,000,000 Da or more, or more typically in the range of 5000 to 500,000 Da (e.g., biomolecules of 1000 Da, 2000 Da, 5000 Da, 10,000 Da, 50,0000 Da, 100,000 Da, 500,000 Da, 1,000,000 Da, etc.). This can be particularly useful for the extraction of biomolecule complexes, e.g., complexes comprising two or more proteins bound to one another by covalent or non-covalent interactions, a protein bound to a polynucleotide, etc. It is known that many clinically relevant biomolecules function as part of such complexes, which can in some cases, be quite large. Thus, one advantage of the subject invention is that it facilitates the study of such complexes.

With regard to the extraction of biomolecule complexes, in some embodiments the invention provides methods for purifying and characterizing such complexes. For example, a complex of interest can be adsorbed to the extraction surface, and then components of the complex selectively desorbed and collected, and optionally subjected to further characterization, e.g., by MS, NMR or SPR. The non-denaturing conditions of the 3-D extraction surfaces lend themselves particularly to this type of analysis, since often times these biomolecule complexes are quite fragile.

Properties of a 3-D extraction surface of the invention, including thickness and porosity, can be modified by varying the MW (or MW range) of the polymer backbone. Polymers in the MW range from about 500 to several million can be used, preferably at least 1000, for example in the range of 10,000 to 500,000. In some cases an increase in MW can result in improved performance, e.g., higher capacity. For example, dextran is available in a variety of MW ranges, allowing for modification of physical characteristics of the resulting hydrogel. Properties of the hydrogel can also be modified by variation of functional groups, extent and nature of cross-linking, etc.

As used herein the terms "affinity binding agent" and "extraction reagent" refer to a molecule or functional group having a specific binding affinity for a molecule or chemical moiety of interest. For example, the affinity group could have a specific affinity for a particular biomolecule or class of biomolecules, or for a specific motif or chemical moiety. Examples would be affinity binding agents (e.g., a ligand) that specifically bind to antibodies or particular classes of antibodies (e.g., Protein A or Protein G) or that specifically bind an affinity tag used to purify recombinant fusion proteins (e.g., a poly-histidine tag). Preferred are affinity binding agents that interact selectively and reversibly with an analyte of interest. The references listed below show different types of affinity binding groups used for solid phase extraction and are hereby incorporated by reference herein in their entireties. Antibody Purification Handbook, Amersham Biosciences, Edition AB, 18-1037-46 (2002); Protein Purification Handbook, Amersham Biosciences, Edition AC, 18-1132-29 (2001); Affinity Chromatography Principles and Methods, Amersham Pharmacia Biotech, Edition AC, 18-1022-29 (2001); The Recombinant Protein Handbook, Amersham Pharmacia Biotech, Edition AB, 18-1142-75 (2002); and Protein Purification: Principles, High Resolution Methods, and Applications, Jan-Christen Janson (Editor), Lars G. Ryden (Editor), Wiley, John & Sons, Incorporated (1989).

There are a wide variety of affinity binding agents suitable for use in embodiments of the subject invention. Many of the groups fall into one of the following interaction categories:

1. Chelating metal—ligand interaction
2. Protein—Protein interaction
3. Organic molecule or moiety—Protein interaction
4. Sugar—Protein interaction
5. Nucleic acid—Protein interaction
6. Nucleic acid—nucleic acid interaction In Table C are listed a number of examples of affinity binding reagents, the corresponding analyte, and the interaction category.

TABLE C

| Examples of Affinity molecule or moiety fixed at surface | Captured biomolecule | Interaction Category |
|---|---|---|
| Ni-NTA | His-tagged protein | 1 |
| Ni-NTA | His-tagged protein within a multi-protein complex | 1, 2 |
| Fe-IDA | Phosphopeptides, phosphoproteins | 1 |
| Fe-IDA | Phosphopeptides or phosphoproteins within a multi-protein complex | 1, 2 |
| Antibody or other Proteins | Protein antigen | 2 |
| Antibody or other Proteins | Small molecule-tagged | 3 |

TABLE C-continued

| Examples of Affinity molecule or moiety fixed at surface | Captured biomolecule | Interaction Category |
|---|---|---|
| Antibody or other Proteins | Small molecule-tagged protein within a multi-protein complex | 2, 3 |
| Antibody or other Proteins | Protein antigen within a multi-protein complex | 2 |
| Antibody or other Proteins | Epitope-tagged protein | 2 |
| Antibody or other Proteins | Epitope-tagged protein within a multi-protein complex | 2 |
| Protein A, Protein G or Protein L | Antibody | 2 |
| Protein A, Protein G or Protein L | Antibody | 2 |
| ATP or ATP analogs; 5'-AMP | Kinases, phosphatases (proteins that requires ATP for proper function) | 3 |
| ATP or ATP analogs; 5'-AMP | Kinase, phosphatases within multi-protein complexes | 2, 3 |
| Cibacron 3G | Albumin | 3 |
| Heparin | DNA-binding protein | 4 |
| Heparin | DNA-binding proteins within a multi-protein complex | 2, 4 |
| Lectin | Glycopeptide or glycoprotein | 4 |
| Lectin | Glycopeptide or glycoprotein within a multi-protein complex | 2, 4 |
| ssDNA or dsDNA | DNA-binding protein | 5 |
| ssDNA or dsDNA | DNA-binding protein within a multi-protein complex | 2, 5 |
| ssDNA | Complementary ssDNA | 6 |
| ssDNA | Complementary RNA | 6 |
| Streptavidin/Avidin | Biotinylated peptides (ICAT) | 3 |
| Streptavidin/Avidin | Biotinylated engineered tag fused to a protein (see avidity.com) | 3 |
| Streptavidin/Avidin | Biotinylated protein | 3 |
| Streptavidin/Avidin | Biotinylated protein within a multi-protein complex | 2, 3 |
| Streptavidin/Avidin | Biotinylated engineered tag fused to a protein within a multi-protein complex | 2, 3 |
| Streptavidin/Avidin | Biotinylated nucleic acid | 3 |
| Streptavidin/Avidin | Biotinylated nucleic acid bound to a protein or multi-protein complex | 2, 3 |
| Streptavidin/Avidin | Biotinylated nucleic acid bound to a complementary nucleic acid | 3, 6 |

U.S. patent application Ser. No. 10/434,713 describes in more detail the use of specific affinity binding reagents in capillary solid-phase extraction. Examples of specific affinity binding agents include proteins having an affinity for antibodies, Fc regions and/or Fab regions such as Protein G, Protein A, Protein A/G, and Protein L; chelated metals such as metal-NTA chelate (e.g., Nickel NTA, Copper NTA, Iron NTA, Cobalt NTA, Zinc NTA), metal-IDA chelate (e.g., Nickel IDA, Copper IDA, Iron IDA, Cobalt IDA) and metal-CMA (carboxymethylated aspartate) chelate (e.g., Nickel CMA, Copper CMA, Iron CMA, Cobalt CMA, Zinc CMA); glutathione surfaces-nucleotides, oligonucleotides, polynucleotides and their analogs (e.g., ATP); lectin surface-heparin surface-avidin or streptavidin surface, a peptide or peptide analog (e.g., that binds to a protease or other enzyme that acts upon polypeptides).

In some embodiments of the invention, the affinity binding reagent is one that recognizes one or more of the many affinity groups used as affinity tags in recombinant fusion proteins. Examples of such tags include poly-histidine tags (e.g., the 6×-His tag), which can be extracted using a chelated metal such as Ni-NTA-peptide sequences (such as the FLAG epitope) that are recognized by an immobilized antibody; biotin, which can be extracted using immobilized avidin or streptavidin; "calmodulin binding peptide" (or, CBP), recognized by calmodulin charged with calcium-glutathione S-transferase protein (GST), recognized by immofbilized glutathione; maltose binding protein (MBP), recognized by amylose; the cellulose-binding domain tag, recognized by immobilized cellulose; a peptide with specific affinity for S-protein (derived from ribonuclease A); and the peptide sequence tag CCxxCC (where xx is any amino acid, such as RE), which binds to the affinity binding agent bis-arsenical fluorescein (FlAsH dye).

Antibodies can be extracted using, for example, proteins such as protein A, protein G, protein L, hybrids of these, or by other antibodies (e.g., an anti-IgE for purifying IgE).

Chelated metals are not only useful for purifying poly-his tagged proteins, but also other non-tagged proteins that have an intrinsic affinity for the chelated metal, e.g., phosphopeptides and phosphoproteins.

Antibodies can also be useful for purifying non-tagged proteins to which they have an affinity, e.g., by using antibodies with affinity for a specific phosphorylation site or phosphorylated amino acids.

In other embodiments of the invention extraction surfaces are employed that are generally less specific than the affinity binding agents discussed above. These extraction chemistries are still often quite useful. Examples include ion exchange, reversed phase, normal phase, hydrophobic interaction and hydrophilic interaction extraction or chromatography surfaces. In general, these extraction chemistries, methods of their use, appropriate solvents, etc. are well known in the art, and in particular are described in more detail in U.S. patent application Ser. No. 10/434,713 and references cited therein, e.g., Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 3 94 (1991); and ORGANIC SYNTHESIS ON SOLID PHASE, F. Dorwald Wiley VCH Verlag Gmbh, Weinheim 2002.

In certain embodiments of the invention, the affinity binding group is distributed in a substantially uniform manner throughout the extraction matrix, e.g., a 3-dimensional matrix. This is in contrast with certain alternative approaches that can be envisioned wherein the extraction chemistry is not uniformly distributed. As an example of non-uniform distribution, consider an inert matrix having particles of chromatographic material (e.g., beads) embedded within the matrix. The chromatographic material might have affinity groups attached to it, e.g., hydrophobic groups like C-4 or C-18, or affinity ligands, but these groups are not present in the inert matrix. Hence, the affinity groups are not uniformly distributed in the matrix, but are concentrated in the embedded chromatography particles.

In some embodiments of the invention it is desirable to prepare an extraction matrix including a functional group in an activated form, e.g., an activated carboxyl. This activation facilitates the coupling of an extraction agent of interest to the matrix, e.g., via formation of an amide bond. For example, an activated carboxyl group can take any of a number of forms, including but not limited to activated reactive esters, hydrazides, thiols or reactive disulfide-containing derivatives. A reactive ester can be prepared in any of a number of ways known to one of skill in the art, including by reaction with a carbodiimide. In one embodiment the activated functional group is a 2-aminoethanethiol derivative. In yet another embodiment the activated functional group is a vinyl sulfone.

In one embodiment, a hydrazide function can be created in dextran matrix for binding ligands containing aldehyde groups, for example antibodies in which the carbohydrate chain has been oxidized so that it then contains an aldehyde function. The dextran matrix is initially modified with, e.g., carboxymethyl groups, which are subsequently reacted to form hydrazide groups.

According to another embodiment, carboxyl groups in carboxymethyl-modified dextran are modified so as to give reactive ester functions, e.g., by treatment with an aqueous solution of N-hydroxysuccinimide and N-(3-dimethylaminopropyl)-N'-ethylcarbodiimide hydrochloride. Ligands containing amine groups such as, for example, proteins and peptides may then be coupled to the dextran matrix by covalent bonds.

According to an alternative procedure, the aforesaid reactive ester is utilized for reaction with a disulfide-containing compound such as for instance 2-(2-pyridinyldithio) ethanamine; in this manner a matrix is obtained which contains disulfide groups, and these can be employed for coupling thiol-containing ligands such as for example reduced F(ab) fragments of immunoglobulins. After cleavage of the disulfide bonds, for instance by reduction or thiol-disulfide exchange, the thiol modified surface formed can be used for coupling of a disulfide-containing ligand such as, for instance, N-succinimidyl 3-(2-pyridinyldithio) propionate (SPDP) modified proteins.

The invention provides methods for preparing extraction capillary channels having 3-dimensional extraction surfaces. In one approach, the extraction surface is prepared by attaching an extraction polymer (e.g., a polymer bearing an affinity group as described herein) to a capillary channel. The attachment is accomplished by means of an interaction between complementary attachment groups on the polymer and channel. The term "complementary" refers to the ability of the attachment groups to interact with one another in such a way as to result in attachment of the polymer to the channel. Examples of such interactions include electrostatic attraction (e.g., where the attachment groups are oppositely charged ions) and hydrophobic interactions (e.g., where the attachment groups are non-polar groups that are attracted to one another in a polar environment). The interaction can be one that results in the formation of a covalent bond, e.g., the complementary attachment groups are functional groups capable of forming covalent bonds, e.g., a carboxyl group and an amide group are complementary functional groups capable of reacting to form an amide bond, vinyl and thiol are complementary functional groups capable of reacting to form a thioether bond. Other examples of complementary groups are cyanogen bromide and the amine group, which can react to form an isourea bond (Porath et al. (1973) J. Chromatograph. 86:53; and Kohn and Wilchek (1984) Appl Biochem. Biotechnol. 9:285-304), and maleimide and thiol, which can react to form a thioether bond (Wang et al. (2003) Bioorganic and Medicinal Chemistry 11:159-6; Toyokuni et al. (2003) Bioconjugate Chem. 14:1253-59; Frisch et al. (1996) Bioconjugate Chem. 7:180-86). The maleimide reaction is particularly useful in certain embodiments of the invention for attaching a group to a polydextran matrix with minimal crosslinking of the matrix. The maleimide group is relatively specific for the thiol group, and not prone to unintended reaction with the dextran matrix. Use of the maleimide group as a linker is exemplified further in the examples, where preparation of a polymaleimide dextran is described. This polymaleimide dextran can be a particularly low-crosslinked matrix, which can be more easily penetrated by some larger molecules, as described elsewhere herein.

In certain embodiments of the invention the inner wall of the extraction channel is derivatized through covalent binding of modified polystyrene latex nanoparticles. In these embodiments, the extraction channel can be a fused silica capillary and the inner wall of the extraction channel is comprised of a latex solid phase extraction surface. The term "latex" is defined herein as a polymer particle. A non-limiting list of particles that can be covalently bound to a fused silica capillary includes biopolymer particles, dextrin, chitosan, polystyrene, substituted polystyrenes, polystyrene co-polymers, poly(methacrylic acid) derivatives, cross-linked polymers, and poly(ethylene imine), polyvinyl chloride, nylon, cyclo or cyclic olefin, fluorolastic, polyamide, acrylic, and polymethylmethacrylate (PMMA).

In certain embodiments, it is desirable to prepare an open tubular capillary with higher capacity by increasing the surface area of the capillary. This can be achieved by coating the inner wall with e.g. 100 nm nanoparticles. In some embodiments of the invention, other particle sizes are used. For example, in various embodiments of the invention, nanoparticle size is at least 0.1 nm, at least 0.5 nm, at least 1 nm, at least 5 nm, at least 10 nm, at least 50 nm, at least 100 nm, at least 150 nm, at least 200 nm, at least 250 nm, at least 500 nm, at least 750 nm, at least 1000 nm, at least 2000 nm, at least 3000 nm, at least 4000 nm, or at least 5000 nm.

In one approach the latex nanoparticles were derivatized with iminodiacetic acid and loaded with $Fe^{3+}$ for the purification and enrichment of phosphopeptides however other metals such as gallium can also be used. In other embodiments of the invention, the latex nanoparticles can be loaded with nickel, copper or cobalt for the purification and enrichment of his-tagged proteins. In other embodiments of the invention, the nanoparticles can be loaded with serum albumin for enrichment of flavones such as catechin. In addition, Protein G immobilized open tubular capillaries can be fabricated for the purification of IgG and Con-A can be used to purify glycosylated proteins.

Covalent binding can be performed in many ways; solid supports often possess hydroxy, amino, amide, and carboxy groups that must be activated before they are able to react directly with proteins. In certain embodiments, the immobilization is done through interaction of the terminal amino group of the protein e.g. concanavalin A or Protein G with the epoxy groups of the latex particles bound to the wall of the fused silica capillary.

To attach the nanoparticles to the inner surface of the fused silica capillary, the capillary is rinsed with 1 M sodium hydroxide to remove inorganic impurities and to hydrolyze the siloxane bonds at the silica surface to silanols. The sodium form of the silanols are converted to the hydrogen form with hydrochloric acid before the capillary was silanized with 3-aminopropyl trimethoxysilane. Then epoxy derivatized polystyrene latex particles are allowed to react with the amino-functionalized fused silica capillary under basic conditions. As a result of this procedure, the latex particles are bound to the inner surface of the capillary in a dense and continuous monolayer. However, in other embodiments, the monolayer may not be entirely continuous.

The capillaries can be eluted under conditions compatible with MALDI-MS or other downstream analytical processes without any prior desalting step. In certain embodiments of the invention, the capillary columns are disposable to prevent sample-to-sample contamination. The attachment of an extraction polymer to a capillary channel can be direct, but more typically is accomplished by one or more linker molecule that serves as intermediaries bridging the polymer and the surface of the extraction channel. Attachments between polymer and linker, linker and channel surface, and/or linker to linker can be covalent or non-covalent. The linker molecule can itself be a polymer, or not. For example, the linker molecule can be a polymer that interacts with the capillary channel and with the extraction polymer, bridging the two. When the capillary channel is silica, for example, surface of the channel is normally covered with silanol groups, resulting in a net negative charge to the surface. A bridge molecule having a positive charge (e.g., a polymer, such as a strong base anion exchanger) can be used to coat the surface, attached thereto by electrostatic attraction. An extraction polymer having a negative charge (e.g., a cation exchanger) can then be attached to the surface through the bridging molecule, in this case by electrostatic attraction to the positively charged bridging polymer. Note that this embodiment involves the successive stacking of layers of polymer having opposite charge on the capillary surface. The number of layers can be one, two or more. For example, successive layers of oppositely charged polymers can be coated on the surface of the capillary channel, with the last applied (or top) layer constituting the extraction surface. In some embodiments the extraction polymer and/or bridge polymers are beads. These beads can be held together by cross-linking (or not). Latex beads are used for this purpose in some of the Examples.

When employing a silica capillary, it is often convenient to covalently couple the matrix to the capillary through free silanol groups on the channel surface. This is typically accomplished through a linking molecule bridging the silanol group and matrix backbone, e.g., polymer. For example, reactive thiol or amino groups can be attached via reaction with a thiosilane or aminosilane, respectively. A carboxyl group can be introduced on the capillary surface by reaction of amino-functionalized capillary with an anhydride, e.g., succinic anhydride.

In another embodiment, a three-dimensional matrix can be attached to a capillary surface through a self-assembled monolayer. This is particularly useful where the capillary is metal, e.g., gold. The attachment of a matrix to a metal surface through a self-assembled monolayer has been described elsewhere, see, for example U.S. Pat. Nos. 5,242,828; 6,472,148; 6,197,515 and 5,620,850.

In an alternative embodiment, a 3-D polymer matrix can be attached through the SMIL (successive multiple ionic-polymer) approach as described by Katayama et al. (1998) Analytical Sciences 14:407-409.

An advantage of the 3-D extraction surfaces of the subject invention is their high surface area relative to a corresponding 2-D extraction surface (i.e., monolayer), which allows for improved analyte binding capacity. That is, the 3-D matrix allows for denser placement of affinity groups (e.g., extraction agents) per surface area of the capillary channel (or length of capillary channel), and/or for denser binding of analyte. For an example of a 2-D extraction surface, or monolayer, see Cai et al. (1993) J. of Liquid Chromatography 16(9&10) 2007-2024, who report fused-silica capillaries having surface-bound iminodiacetic acid metal chelating functions. Note that the support coated capillaries prepared by Cai et al. using a colloidal silica solution do not exhibit the increased capacity of the 3-D extraction matrices of the subject invention, since the silica coating is not swellable (i.e., does not take up water or solvent like polysaccharide polymer such as dextran) and cannot be substantially penetrated by high MW biological macromolecules. Note that the concept of a 2-D monolayer does not necessarily imply a flat surface, since a monolayer surface can be rough or have contours that in some cases can provide some increase in capacity. A 3-D matrix, on the other hand, is penetrable. The capacity of a 2-D binding surface will depend on the diameter of the analyte molecule and the ability of the molecules to "close pack" together. "Close pack" refers to the situation where sides of the analyte molecules are touching or nearly touching each other on a 2-D surface. One way of considering the subject invention is that a 3-D binding phase allows for packing of analyte molecules on a $3^{rd}$ dimension. This packing can be a close pack or approach a close pack in three dimensions. The magnitude of the increased capacity compared to a monolayer follows from the ability of the binding phase to capture analyte molecules in the third dimension.

The three-dimensional nature of the matrix is particularly advantageous in that it allows for much higher binding capacity of large biomolecules such as proteins. To illustrate, consider the binding of a globular protein analyte to a 2-dimensional, monolayer extraction surface. The binding of the globular protein creates a "footprint" on the surface where no other protein is able to bind. In the case of a corresponding 3-D surface, the protein can bind in the matrix at varying distances from the channel surface, allowing for a staggering of the proteins and the capacity to bind many more proteins than would be possible on a 2-D surface in a capillary channel of comparable dimensions. Representative data demonstrating the substantial improvement in protein binding capacity of a 3-D extraction matrix relative to a corresponding 2-D extraction matrix is provided in the Examples. As used in this sense, the term "corresponding" refers to matrices sharing the same affinity group (e.g., extraction agent), the difference between the corresponding matrices being that one is 2-D while the other is 3-D.

Another advantage of the 3-D extraction surface is that it can provide a more gentle and hospitable environment for delicate biomolecules (e.g., large proteins and protein complexes) compared to a 2-D surface. The 3-D matrix allows for the creation of an environment that more closely mimic the properties of bulk solution. This biomolecule-friendly environment can promote protein stability and the retention of native biological activity.

Analytical Techniques

Extraction channels and associated methods of the invention find particular utility in preparing samples of analyte for analysis or detection by a variety analytical techniques. In particular, the methods are useful for purifying an analyte, class of analytes, aggregate of analytes, etc, from a biological sample, e.g., a biomolecule originating in a biological fluid. It is particularly useful for use with techniques that require small volumes of pure, concentrated analyte. In many cases, the results of these forms of analysis are improved by increasing analyte concentration. In some embodiments of the invention the analyte of interest is a protein, and the extraction serves to purify and concentrate the protein prior to analysis. The methods are particularly suited for use with label-free detection methods or methods that require functional, native (i.e., non-denatured protein), but are generally useful for any protein or nucleic acid of interest.

These methods are particularly suited for application to proteomic studies, the study of protein-protein interactions, and the like. The elucidation of protein-protein interaction networks, preferably in conjunction with other types of data, allows assignment of cellular functions to novel proteins and derivation of new biological pathways. See, e.g., Curr Protein Pept Sci. 2003 4(3):159-81.

Capillary Multiplexing

In some embodiments of the invention, a plurality of channels (e.g., capillaries) are operated in parallel, i.e., in a multiplex fashion. This can be accomplished, for example, by arranging the capillaries in parallel so that fluid can be passed through them concurrently. When a pump is used to manipulate fluids through the column, each capillary in the multiplex array can have its own pump, e.g., syringe pumps activated by a common actuator. Alternatively, capillaries can be connected to a common pump, a common vacuum device, or the like. In another example of a multiplex arrangement, the plurality of capillaries is arranged in a manner such that they can be centrifuged, with fluid being driven through the capillaries by centrifugal force.

In one embodiment, sample can be arrayed from an extraction capillary to a plurality of predetermined locations, for example locations on a chip or microwells in a multi-well plate. A precise liquid processing system can be used to dispense the desired volume of eluant at each location. For example, an extraction capillary containing bound analyte takes up 50 µL of desorption solvent, and 1 µL drops are spotted into microwells using a robotic system such as those commercially available from Zymark (e.g., the SciClone sample handler), Tecan (e.g., the Genesis NPS or Te-MO) or Cartesian Dispensing (e.g., the Honeybee benchtop system). This can be used for high-throughput assays, crystallizations, etc.

Figure 5:
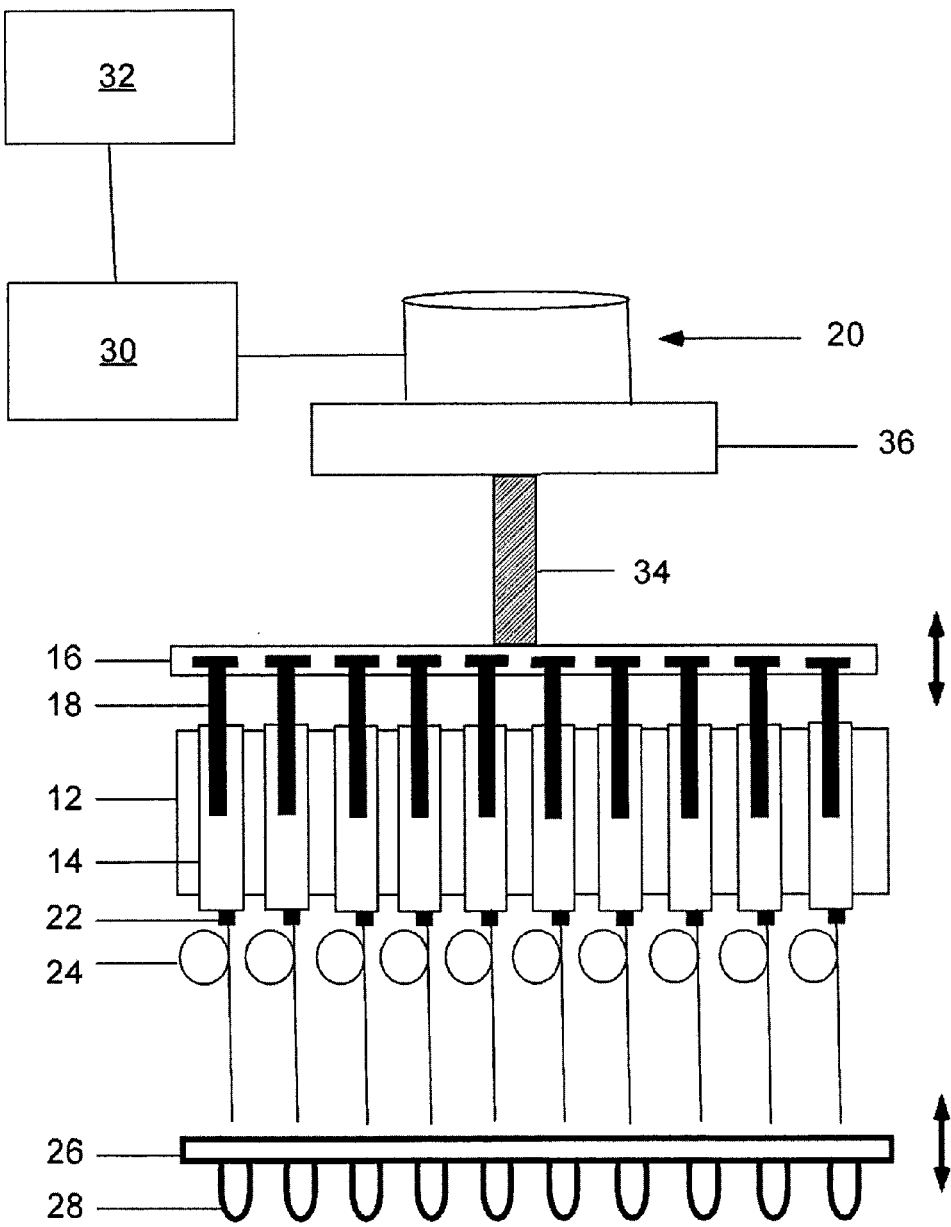
FIG. 5 depicts an example of a multiplexed capillary extraction apparatus.

FIG. 5 depicts an example of a multiplexed capillary extraction system. The system includes a syringe holder 12 for holding a series of syringes 14 and a plunger holder 16 for engaging the plungers 18 with a syringe pump 20. The syringe pump includes a screw 34 to move the plunger holder and a stationary base 36. The syringe pump can move the plunger holder up and down while the syringe holder remains stationary, thus simultaneously actuating all syringe plungers attached to the holder. Each syringe includes an attachment fitting 22 for attachment of an extraction capillary. Attached to each syringe is a coiled fused silica extraction capillary 24. The system also includes a sample rack 26 with multiple positions for holding sample collection vials 28, which can be eppendorf tubes. The sample rack is slidably mounted on two vertical rods, and the height of the rack can be adjusted by sliding it up or down on the rods and locking the rack at the desired location. The position of the rack can be adjusted to bring the input tip of the extraction capillary into contact with solution in a tube in the eppendorf rack. The system also includes a controller 30 for controlling the syringe pump. The controller is attached to a computer 32, which can be programmed to control the movement of the pump through the controller. The controller allows for control of when and at what rate the plunger rack is moved, which in turn is used to control the flow of solution through the capillaries, withdrawal and infusion. Control of the plungers can be manual or automated, by means of a script file that can be created by a user. The software allows for control of the flow rate through the capillaries, and an extraction protocol can include multiple withdraw and infusion cycles, along with optional delays between cycles.

In one example of a multiplexing procedure, 10 Eppendorf tubes containing a sample, e.g., a clarified cell lysate containing a his-tagged recombinant protein, are placed in the sample rack. One mL syringes are attached to the syringe holder, and the plungers are engaged with the plunger holder. One meter long extraction capillaries, e.g., coiled immobilized-metal extraction capillaries as described elsewhere herein, are affixed to the syringe attachment fittings, e.g., via a Luer fitting. The sample rack is raised so that the ends of the extraction tips enter the sample. Sample solution is drawn into the capillaries by action of the syringe pump, which raises the plunger holder and plungers. The pump is preferably capable of precisely drawing up a desired volume of solution at a desired flow rate, and of pushing and pulling solution through the capillary. An example of a suitable syringe pump is the ME-100 (available from PhyNexus, Inc., San Jose, Calif.). Control of the liquid slug is optionally bidirectional. In this case, and where a syringe is used to control the slug, the syringe plunger head and the syringe body should be tightly held within the syringe pump. When the syringe plunger direction is reversed, then there will be a delay or a hysteresis effect before the syringe can begin to move the slug in the opposite direction. This effect becomes more important as the volume of the slug is decreased. However, because slug movement is bidirectional, the hysteresis effect will also affect how close to the end of capillary that the slug can be moved. In the ME-100 instrument, the syringe and syringe plunger are secured so that no discernable movement can be made against the holder rack.

If the sample volume is larger than the volume of the capillary, sample is drawn through the capillary and into the syringe chamber. The sample solution is then expelled back into the sample container. In some embodiments, the process of drawing sample through the capillary and back out into the sample container is performed two or more times, each of which results in the passage of the sample through the capillary twice. As discussed elsewhere herein, analyte adsorption can in some cases be improved by using a slower flow rate and/or by increasing the number of passages of sample through the capillary.

The sample container is then removed and replaced with a similar container holding wash solution (e.g., in the case of an immobilized metal extraction, 5 mM imidazole in PBS), and the wash solution is pumped back and forth through the capillary (as was the case with the sample). The wash step can be repeated one or more times with additional volumes of wash solution.

Figure 6:
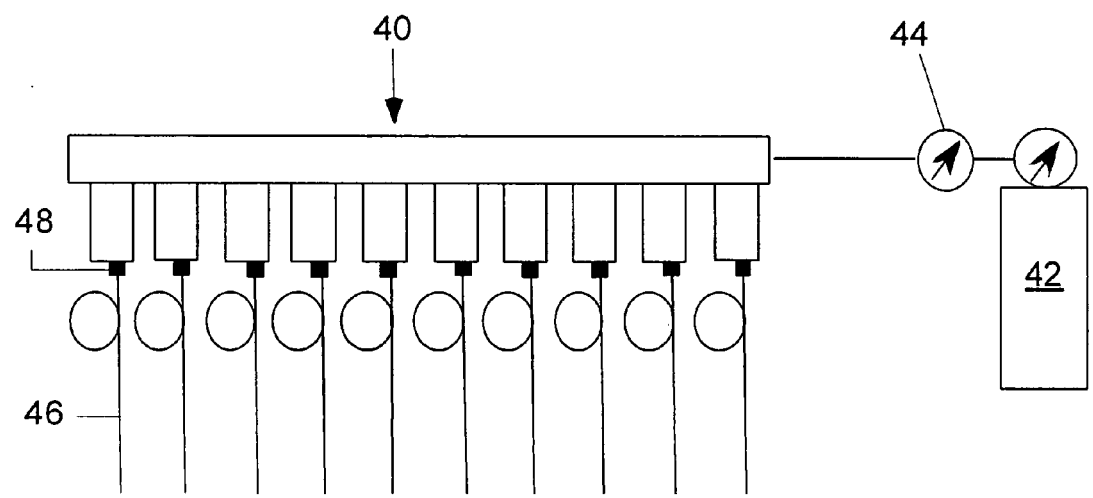
FIG. 6 depicts a gas manifold used in a multiplexed purging operation.

After the wash step, the capillary is typically purged with gas to remove residual solution. In a multiplexed operation such as this, it is useful to use a gas manifold to facilitate the process of purging. An example of such as manifold is shown in FIG. 6. The manifold 40 is attached to a canister 42 holding gas under pressure, along with a valve 44 for controlling release of the gas through the manifold. Capillaries 46 to be purged (in this example ten) are attached to the exit ports 48 of the manifold, and the valve is opened to allow gas to pass through the capillaries in multiplex fashion. A typical purge protocol would involve application of 50 psi gas (either nitrogen or helium) for a total of about 30-60 seconds.

Following the purge, the capillaries are put back onto syringes on the multiplexed extraction apparatus to perform the elution. Optionally, the syringe can be changed prior to elution. For example, 1 mL disposable syringes used for sample and wash solution can be replaced with 50 µL GasTight syringes for the elution. The original sample rack (or a different sample collection tray) is then filled with sample collection vials (e.g., 0.5 mL Eppendorf tubes), and the height of the tubes adjusted so that the capillary openings are just above the bottom of the individual samples tubes. An aliquot of desorption solvent is placed at the bottom of each tube (e.g., 2-15 µL of 200 mM imidazole would be typical for elution of protein off an immobilized metal column). The desorption solution is taken up into the capillary to a point near the attachment to the syringe, e.g., near the Luer fitting. For example, if the volume of desorption solution is 15 μL and the volume of the capillary is about 30 μL, the pump can be programmed to pull up the 15 μL of desorption solution followed by 15 μL of air, e.g., at a flow rate of about 0.03 mL/min. The slow rate should be slow enough to allow the integrity of the fluid segment to be maintained at all times. The eluant can be allowed to incubate in the capillary. For example, the 15 μL of desorption solution can be incubated for 60 seconds at the top half of a 30 μL capillary, then pushed down to the lower 15 μL of the capillary and allowed to incubate there for another 60 seconds. The elution cycle is completed by ejecting the desorption solution back into the sample vial. The elution process can be repeated, in some cases allowing for improved sample recovery.

The above-described extraction process can be automated, for example by using software to program the computer controller to control the pumping, e.g., the volumes, flow rates, delays, and number of cycles.

In some embodiments, the invention provides a multiplexed extraction system comprising a plurality of extraction channels of the invention, e.g., fused silica extraction capillaries. The system can include a pump or pumps in operative engagement with the extraction channels, useful for pumping fluid through the capillaries in a multiplex fashion, i.e., concurrently. In some embodiments, each capillary is addressable. The term "addressable" refers to the ability of the fluid manipulation mechanism, e.g., the pumps, to individually address each capillary. An addressable channel is one in which the flow of fluid through the channel can be controlled independently from the flow through any other channel which may be operated in parallel. In practice, this means that the pumping means in at least one of the extraction steps is in contact and control of each individual channel independent of all the other channels. For example, when syringe pumps are used, i.e., pumps capable of manipulating fluid within the capillary by the application of positive or negative pressure, then separate syringes are used at each capillary, as opposed to a single vacuum attached to multiple syringes. Because the capillaries are addressable, a controlled amount of liquid can be accurately manipulated in each capillary. In a non-addressable system, such as where a single pump is applied to multiple capillaries, the liquid handling can be less precise. For example, if the back pressure differs between multiplexed capillaries, then the amount of liquid entering each capillary and/or the flow rate can vary substantially in a non-addressable system. Various embodiments of the invention can also include sample racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

The possible means for fluid manipulation are varied. For example, another embodiment of the invention particularly suited for use in a multiplex context is illustrated in FIGS. 7A-J. The embodiment employs a manifold 52, which includes a plunger-barrel 54, a precision plunger 56 slidably positioned in the manifold so that it can slide through barrel 58, and an inlet port 60 in communication with the barrel 58 (FIG. 7A). In operation, a disposable cartridge 70, comprising a fluid reservoir 72 and a capillary holder 74 is attached to the manifold by sliding the end of the plunger-barrel into the reservoir (FIG. 7B). A seal between the plunger-barrel and the wall of the reservoir is achieved by means of the seal 76. The lower end of the capillary 78 is brought into contact with sample solution 80, contained in sample vial 82, which is positioned in a sample tray. Sample solution is drawn from the sample vial through the capillary and into the reservoir through the upper end of the capillary 84. The sample solution is drawn into and out of the disposable reservoir by lowering the precision plunger 56 to seal the top 50 of the plunger-barrel 54 and pushing and pulling the barrel-plunger 54 like a syringe (FIGS. 7C-7D). The precision plunger 56 is then raised and wash solution is blown through the port 60, the reservoir 72 and out through the capillary 74 (FIG. 7E). The plunger-barrel 54 is then lowered to the bottom of the reservoir (FIG. 7F). Optionally, a second wash (e.g., water) can be blown through the port 60 and through the capillary in down position. Nitrogen is then blown through the port 60 and into the capillary 74 to purge the capillary (FIG. 7G). The lower end of the capillary 78 is inserted into desorption solution 92 (FIG. 7H). The precision plunger 56 is then operated to draw a slug of desorption solution through the capillary until it reaches near the end 84 without entering the barrel (FIG. 7J). The precision plunger 56 is used to control the movement of the plug back and forth in the capillary as described elsewhere herein, and finally the slug of desorption solution containing eluted analyte is collected in a sample vial 94 or deposited on a target (FIG. 7J).

Multiple variations of the above-described embodiments can be readily arrived at and fall within the scope of the claimed invention. For example, the liquid solutions can be introduced into the capillary from either end, e.g., by being pulled up via a plunger or pushed through the capillary from the inlet port. In various embodiments, manipulation of solution in the capillary can be accomplished by means of the precision plunger, the barrel-plunger, or by positive and/or negative pressure applied through the inlet, e.g., by means of a pump, pressurized air, etc. In some embodiments, the plunger is not used in an extraction process; manipulation of fluid is accomplished by means of, e.g., a pump attached at the inlet. The plunger can even be omitted from the manifold in certain embodiments, e.g., where all fluid enters and is controlled via the inlet.

The invention also provides software for implementing the methods of the invention. For example, the software can be programmed to control manipulation of solutions and addressing of capillaries into sample vials, collection vials, for spotting or introduction into some analytical device for further processing.

The invention also includes kits comprising one or more reagents and/or articles for use in a process relating to solid-phase extraction, e.g., buffers, standards, solutions, capillaries, sample containers, etc.

Step and Multi-Dimensional Elutions

In some embodiments of the invention, desorption solvent gradients, step elutions and/or multidimensional elutions are performed.

The use of gradients is well known in the art of chromatography, and is described in detail, for example in a number of the general chromatography references cited herein. As applied to the extraction channels of the invention, the basic principle involves adsorbing an analyte to the extraction surface and then eluting with a desorption solvent gradient. The gradient refers to the changing of at least one characteristic of the solvent, e.g., change in pH, ionic strength, polarity, or the concentration of some agent that influence the strength of the binding interaction. The gradient can be with respect to the concentration of a chemical entity that interferes with or stabilizes an interaction, particularly a specific binding interaction. For example, where the affinity binding agent is an immobilized metal the gradient can be in the concentration of imidazole, EDTA, etc. In some embodiments, the result is fractionation of a sample, useful in contexts such as gel-free shotgun proteomics.

As used herein, the term "dimension" refers to some property of the desorption solvent that is varied, e.g., pH, ionic strength, etc. An elution scheme that involves variation of two or more dimensions, either simultaneously or sequentially, is referred to as a multi-dimensional elution.

Gradients used in the context of the invention can be step. Step elutions are particularly applicable, particularly when segments of desorption solvent bounded by air and/or some other immiscible fluid are employed. In one embodiment, two or more plugs of desorption solvent varying in one or more dimension are employed. For example, the two or more plugs can vary in pH, ionic strength, hydrophobicity, or the like. The segment can have a volume greater than the capillary or less, i.e., a tube enrichment factor of greater than one can be achieved with each plug. Optionally, the capillary can be purged with gas prior to introduction of one or more of the desorption solvent plugs. In one embodiment, the plugs are introduced and ejected from the same end of the capillary. The plug is passed back and forth through the column one or more times. As described elsewhere herein, in some cases the efficiency of desorption is improved by lowering the flow rate of desorption solvent through the capillary and/or by increasing the number of passages, i.e., flowing the solvent back and forth through the capillary.

In another embodiment, a series of two or more plugs of desorption solvent is run through the capillary in sequence, separated by segments of air. In this embodiment, the air-separated segments vary in one or more dimensions. The plugs of solvent can enter and leave the capillary from the same or different ends, or they can enter the capillary at one end and leave from the other. Thus, for example, a series of plugs separated by air can be introduced at one end, and the discrete plugs collected or analyzed directly, for example by introducing each plug into an MS ionization apparatus or onto a protein chip.

In some embodiments of the invention a multidimensional stepwise solid phase extraction is employed. This is particularly useful in the analysis of isotope-coded affinity tagged (ICAT) peptides, as described in U.S. patent application Ser. No. 10/434,713 and references cited therein. A multi-dimensional extraction involves varying at least two desorption condition dimensions.

In a typical example, a stepwise elution is performed in one dimension, collecting fractions for each change in elution conditions. For example, a stepwise increase in ionic strength could be employed where the extraction phase is based on ion exchange. The eluted fractions are then introduced into a second capillary (either directly or after collection into an intermediate holding vessel) and in this case separated in another dimension, e.g., by reverse-phase, or by binding to an affinity binding group such as avidin or immobilized metal.

In some embodiments, one or more dimensions of a multidimensional extraction are achieved by means other than an extraction capillary. For example, the first dimension separation might be accomplished using conventional chromatography, electrophoresis, or the like, and the fractions then loaded on an extraction capillary for separation in another dimension.

Note that in many cases the elution of a protein will not be a simple on-off process. That is, some desorption buffers will result in only partial release of analyte. The composition of the desorption buffer can be optimized for the desired outcome, e.g., complete or near complete elution. Alternatively, when step elution is employed two or more successive steps in the elution might result in incremental elution of fraction of an analyte. These incremental partial elution can be useful in characterizing the analyte, e.g., in the analysis of a multi-protein complex as described below.

Multi-Protein Complexes

In certain embodiments, extraction capillaries of the invention are used to extract and/or process multi-protein complexes. This is accomplished typically by employing a sample solution that is sufficiently non-denaturing that it does not result in disruption of a protein complex or complexes of interest, i.e., the complex is extracted from a biological sample using a sample solution and extraction conditions that stabilize the association between the constituents of the complex. As used herein, the term multi-protein complex refers to a complex of two or more proteins held together by mutually attractive chemical forces, typically non-covalent interactions. Non-covalent attachments would typically be reversible, thus allowing for recovery of component proteins.

In some embodiments, multi-protein complex is adsorbed to the extraction surface and desorbed under conditions such that the integrity of the complex is retained throughout. That is, the product of the extraction is the intact complex, which can then be collected and stored, or directly analyzed (either as a complex or a mixture of proteins), for example by any of the analytical methodologies described herein.

One example involves the use of a recombinant "bait" protein that will form complexes with its natural interaction partners. These multiprotein complexes are then purified through a fusion tag that is attached to the "bait." These tagged "bait" proteins can be purified through groups attached to the surface of the capillary such as metal-chelate groups, antibodies, calmodulin, or any of the other surface groups employed for the purification of recombinant proteins. The identity of the cognate proteins can then be determined by any of a variety of means, such as MS.

It is also possible to purify "native" (i.e. non-recombinant) protein complexes without having to purify through a fusion tag. For example, this can be achieved by using as an affinity binding reagent an antibody for one of the proteins within the multiprotein complex. This process is often referred to as "co-immunoprecipitation." The multiprotein complexes can be eluted, for example, with low pH.

In some embodiments, the multi-protein complex is loaded onto the column as a complex, and the entire complex or one or more constituents are desorbed and eluted. In other embodiments, one or more complex constituents are first adsorbed to the extraction surface, and subsequently one or more other constituents are applied to the extraction surface, such that complex formation occurs on the extraction surface.

In another embodiment, the extraction capillaries of the invention can be used as a tool to analyze the nature of the complex. For example, the protein complex is adsorbed to the extraction surface, and the state of the complex is then monitored as a function of solvent variation. A desorption solvent, or series of desorption solvents, can be employed that result in disruption of some or all of the interactions holding the complex together, whereby some subset of the complex is released while the rest remains adsorbed. The identity and state (e.g., post-translational modifications) of the proteins released can be determined often, using, for example, MS. Thus, in this manner constituents and/or sub-complexes of a protein complex can be individually eluted and analyzed. The nature of the desorption solvent can be adjusted to favor or disfavor interactions that hold protein complexes together, e.g., hydrogen bonds, ionic bonds, hydrophobic interactions, van der Waals forces, and covalent interactions, e.g., disulfide bridges. For example, by decreasing the polarity of a desorption solvent hydrophobic interactions will be weakened-inclusion of reducing agent (such as mercaptoethanol or dithiothrietol) will disrupt disulfide bridges. Other solution variations would include alteration of pH, change in ionic strength, and/or the inclusion of a constituent that specifically or non-specifically affects protein-protein interactions, or the interaction of a protein or protein complex with a non-protein biomolecule.

In one embodiment, a series of two or more desorption solvents is used sequentially, and the eluent is monitored to determine which protein constituents come off at a particular solvent. In this way it is possible to assess the strength and nature of interactions in the complex. For example, if a series of desorption solvents of increasing strength is used (e.g., increasing ionic strength, decreasing polarity, changing pH, change in ionic composition, etc.), then the more loosely bound proteins or sub-complexes will elute first, with more tightly bound complexes eluting only as the strength of the desorption solvent is increased.

In some embodiments, at least one of the desorption solutions used contains an agent that effects ionic interactions. The agent can be a molecule that participates in a specific interaction between two or more protein constituents of a multi-protein complex, e.g., Mg-ATP promotes the interaction and mutual binding of certain protein cognates. Other agents that can affect protein interactions are denaturants such as urea, guanadinium chloride, and isothiocyanate, detergents such as triton X-100, chelating groups such as EDTA, etc.

In other sets of experiments, the integrity of a protein complex can be probed through modifications (e.g., post-translational or mutations) in one or more of the proteins. Using the methods described herein the effect of the modification upon the stability or other properties of the complex can be determined.

In some embodiments of the invention, multidimensional solid phase extraction techniques, as described in more detail elsewhere herein, are employed to analyze multiprotein complexes.

Recovery of Native Proteins

In one embodiment, the capillary extraction devices and methods of the invention are used to purify proteins that are functional, active and/or in their native state, i.e., non-denatured. This is accomplished by performing the extraction process under non-denaturing conditions. Non-denaturing conditions encompasses the entire protein extraction process, including the sample solution, the wash solution (if used), the desorption solution, the extraction phase, and the conditions under which the extraction is accomplished. General parameters that influence protein stability are well known in the art, and include temperature (usually lower temperatures are preferred), pH, ionic strength, the use of reducing agents, surfactants, elimination of protease activity, protection from physical shearing or disruption, radiation, etc. The particular conditions most suited for a particular protein, class of proteins, or protein-containing composition vary somewhat from protein to protein.

One particular aspect of the extraction capillary technology of the invention that facilitates non-denaturing extraction is that the process can be accomplished at low temperatures. In particular, because solution flow through the capillary can be done without heating the capillary, e.g., without the introduction of electrical current or the generation of joule heat that typically accompanies capillary processes involving chromatography or electroosmotic flow, the process can be carried out at lower temperatures. Lower temperature could be room temperature, or even lower, e.g., if the process is carried out in a cold room, or the a cooling apparatus is used to cool the capillary. For example, capillary extractions can be performed at a temperature as low as 0° C., 2° C. or 4° C., e.g., in a range such as 0° C. to 30° C., 0° C. to 20° C., 2° C. to 30° C., 2° C. to 20° C., 4° C. to 30° C., or 4° C. to 20° C.

Another aspect of capillary extraction as described herein that allows for purification of native proteins is that the extraction process can be completed quickly, thus permitting rapid separation of a protein from proteases or other denaturing agents present in sample solution. The speed of the process allows for quickly getting the protein from the sample solution to the analytical device for which it is intended, or to storage conditions that promote stability of the protein. In various embodiments of the invention, protein extractions of the invention can be accomplished in less than 1 minute, less than 2 minutes, less than 5 minutes, less than 10 minutes, less than 15 minutes, less than 20 minutes, less than 60 minutes, or less than 120 minutes.

In another aspect, extracted protein is sometimes stabilized by maintaining it in a hydrated form during the extraction process. For example, if a purge step is used to remove bulk liquid (i.e., liquid segments) from the capillary prior to desorption, care is taken to ensure that gas is not blown through the capillary for an excessive amount of time, thus avoiding drying out the capillary and possibly desolvating the extraction phase and/or protein.

In another embodiment, the extraction process is performed under conditions that do not irreversibly denature the protein. Thus, even if the protein is eluted in a denatured state, the protein can be renatured to recover native and/or functional protein. In this embodiment, the protein is adsorbed to the extraction surface under conditions that do not irreversibly denature the protein, and eluting the protein under conditions that do not irreversibly denature the protein. The conditions required to prevent irreversible denaturation are similar to those that are non-denaturing, but in some cases the requirements are not as stringent. For example, the presence of a denaturant such as urea, isothiocyanate or guanidinium chloride can cause irreversible denaturation. The eluted protein is denatured, but native protein can be recovered using techniques known in the art, such as dialysis to remove denaturant. Likewise, certain pH conditions or ionic conditions can result in reversible denaturation, readily reversed by altering the pH or buffer composition of the eluted protein.

The recovery of non-denatured, native, functional and/or active protein is particularly useful as a preparative step for use in processes that require the protein to be denatured in order for the process to be successful. Non-limiting examples of such processes include analytical methods such as binding studies, activity assays, enzyme assays, X-ray crystallography and NMR.

In another embodiment, the invention is used to stabilize RNA. This can be accomplished by separating the RNA from some or substantially all RNAse activity, enzymatic or otherwise, that might be present in a sample solution. In one example, the RNA itself is extracted and thereby separated from RNAse in the sample. In another example, the RNase activity is extracted from a solution, with stabilized RNA flowing through the capillary. Extraction of RNA can be sequence specific or non-sequence specific. Extraction of RNAse activity can be specific for a particular RNAse or class of RNAses, or can be general, e.g., extraction of proteins or subsets of proteins.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Hydroxide Etch-Conditioning of Fused Silica Capillary Tubing

Fused silica capillaries (204 um ID, 362 um OD; 50 meters×2; obtained from Polymicro Inc. (Phoenix, Ariz., lot #PBW04A)) were etched by treatment of the channel surface with 100 mM NaOH for 50 minutes. The capillaries were then washed with water (6.0 mL), 0.1N HCl (2 mL), water (10 mL) and acetonitrile (6 mL), after which they were dried with nitrogen gas.

Example 2

Synthesis of Amino-Functionalized Capillary

A 10 meter section of the etched capillary described in Example 1 was filled with a solution of $(MeO)_3Si(CH_2)_3NH_2$ (400 uL) in toluene (1200 uL). The capillary was placed in a 120° C. oil-bath and the reaction continued for 16 h with the flow of the silanization solution through the capillary adjusted to 0.8 uL/min. The capillary was then washed with toluene (1000 uL), acetonitrile (2000 uL), and dried with nitrogen.

Example 3

Synthesis of Carboxylic Acid-Functionalized Capillary

A four meter length of the amino-functionalized capillary described in Example 2 was filled with a solution of succinic anhydride (125 mg; 1.25 mmol), DMAP (20 mg), pyridine (25 uL) in DMF (400 uL) and acetonitrile (900 uL). The capillary was placed in a 65 C oven and the reaction continued for 15 h with the flow of the succinic anhydride solution adjusted to 0.6 uL/min. The capillary was then washed with acetonitrile (2000 uL).

Example 4

Synthesis of "Nitrilotriacetic Acid" (NTA)

N,N-Bis-(carboxymethyl) lysine (commonly referred to as "Nitrilotriacetic acid," or "NTA") was synthesized as follows based the procedure reported by Hochuli et al. (Journal of Chromatography, 411:177-184 (1987)).

A solution of H-Lys(Z)—OH (42 g; 150 mmol) in 2N NaOH (225 mL) was added drop wise to a solution of bromoacetic acid (42 g; 300 mmol; 2 eq) in 2N NaOH (150 mL) at ~0 to 10° C. White precipitate formed as the solution of H-Lys(Z)—OH added. The reaction continued at room temperature (RT) overnight, after which the temperature was increased to 60° C. and the reaction continued for another 2 h. 1N HCl (450 mL) was added and the mixture was placed in a refrigerator for a couple hours. The solid product (Z-protected NTA) was filtered off and recrystalized by re-dissolving the solid in 1N NaOH, then neutralized with the same amount of 1N HCl. The Z-protected NTA was collected by filtration and dried.

Z-protected NTA was dissolved in 1N NaOH (130 mL) and 5% Pd/C (~450 mg) was added. The reaction mixture was evacuated and saturated with $H_2$ before being stirred at RT under $H_2$ balloon overnight. The reaction mixture was filtered through a celite bed to remove the Pd/C. The filtrate, containing NTA was collected and water (80 mL) was used to wash the filtering bed. 6N HCl was added to bring the pH down to 7.5-8.0. The collected NTA solution was diluted with water to have the final concentration of ~200 mM.

Example 5

Synthesis of an Extraction Capillary Coated with a NTA Monolayer

A four meter length of the carboxyl-functionalized capillary described in Example 3 was activated by filling the capillary with a solution of N-hydroxysuccinimide (115 mg; 1.0 mmol), and EDAC (191.7 mg; 1.0 mmol) in acetonitrile (1500 uL). The reaction continued for 3 h at RT with the flow of the above solution through the capillary adjusted to 5 uL/min. (The reaction can also be carried out for about 14 h with the flow of the reagents solution adjusted to 0.6 uL/min.)

The activated capillary was washed with acetonitrile (1000 uL), then treated with a solution of NTA (described in Example 4) in water (200 mM; pH~8; 1.0 mL). The reaction continued for 14 h at RT with the flow rate adjusted to ~1 uL/min. The capillary was further reacted with 0.5% ethanolamine in water for 2 min before it was washed with water (4 mL).

Example 6

Charging a NTA Extraction Capillary with $Ni^{2+}$

An extraction capillary coated with NTA monolayer as described in Example 5 was washed by flowing 500 uL of 100 mM NaHCO3 through the capillary at a fast flow rate. The washed capillary was then charged with 10 mM $NiSO_4$ for 20 min (flow rate ~0.02 mL/min). The charged capillary was then washed with water (1 mL at a fast flow rate), followed by 10 mM NaCl (500 uL; 0.05 mL/min), and then a final water wash (6 mL; 0.1 mL/min). Toward the end of the final water wash the effluent spot checked with PAR reagent (pyridineazoresorcinol) for the presence of any $Ni^{2+}$ (see Example 18).

The capillary was then cut into 1 meter lengths each for use in extraction procedures.

Capillaries that have been used in extractions can be re-charged using the same procedure. Prior to re-charging a capillary it should be washed with 50 mM $Na_2EDTA$ (500 uL; fast with about 1 min of incubation).

Example 7

Synthesis of $HSCH_2CO-NTA$

To a solution of thioglycolic acid (460 mg; 5.0 mmol) in acetonitrile (14 mL) was added N-hydroxysuccinimide (600 mg; 5.2 mmol) followed with DCC (1.1 mg; 5.5 mmol). The reaction continued for 30 min at RT (it was noted that a substantial amount of ppt formed after a couple minutes of reaction). The insoluble by-product DCU was filtered off and washed with additional acetonitrile (4 mL). The combined colorless product solution was added to a solution of NTA (see Example 4; 175 mM; pH~8.2; 30 mL; 5.25 mmol; this solution was purged with nitrogen for about 10 min prior to the reaction) and the pH of the reaction mixture adjusted to 8.65 with 1N NaOH. The reaction continued for 3 h at room temperature under nitrogen. The pH of the reaction mixture was readjusted to 2.5 with 6N HCl before being filtered through a fritted pipette tip. The total volume was 50 mL and assuming 100% yield, the concentration of this solution was 100 mM.

Example 8

Synthesis of Thiol-Functionalized Capillary

Etched capillaries were prepared as described in Example 1 and were filled with a solution of $(MeO)_3Si(CH_2)_3SH$ (20% in toluene) before being placed in an oven at ~125° C. The reaction continued for 16 h with the flow of the silanization solution through the capillary adjusted to 0.15 mL/hour. The capillaries were washed with toluene (3000 uL), acetonitrile (2000 uL), water (4 mL), acetonitrile (3000 uL), and dried with nitrogen.

Example 9

Vinylsulfonedextran Synthesis

Dextran (Fluka, St. Louis, Mo. #31387; MW. 15000-20000; 2 g; 37 mmol of —OH) was dissolved in water (60 mL) and phosphate buffer (pH 11.5; 400 mM $Na_2HPO_4$/NaOH; 20 mL) before $NaBH_4$ (40 mg) was added, followed by divinylsulfone (5.5 mL; 74 mmol; 1.5 eq.; added all at once). The reaction continued at RT for 27 minutes, then quenched by adjusting the pH to 6 with 6N HCl. The light yellow reaction mixture was dialyzed and lyophilized.

Example 10

Procedure for Determining the Capacity of an $Ni^{2+}$-NTA Extraction Capillary Via His-GST Protein A $Ni^{2+}$-NTA capillary of interest is dried with $N_2$, and then loaded with a 20 uL sample plug of a 2500 ug/mL stock solution of His-GST protein (described in U.S. patent application Ser. No. 10/434,713). The sample plug is moved through the capillary two complete cycles with about 2-5 min of incubation before being expelled from the capillary. The capillary is then washed with water (500 uL; fast flow rate), followed by PBS (10 mM phosphate pH7+140 mM NaCl; 500 uL with about 1 min of incubation) and water (500 uL; fast flow rate). The capillary is then dried (air or $N_2$) for about 2-5 min.

Next the protein is eluted off the capillary with 200 mM imidazole (15 uL). The imidazole plug is moved through the capillary two complete cycles with about 2-5 min of incubation before being expelled from the capillary and collected. 15 uL of water is then added to the collected sample.

The amount of protein in the sample is determined by running sample on an HP1050 HPLC system using a gradient of 25-75% B in 5 min. (solvent A: 0.1% TFA in water and solvent B: 0.1% TFA in acetonitrile) with the detection wavelength of 214 nm, and integrating the protein absorbance peak. A calibration standard is used, which is made by adding 15 uL of a 125 ug/mL protein solution with 15 uL of 200 mM imidazole.

Example 11

Extracting Multi-Protein DNA-Binding Complexes with Mass Spectrometric Identification of the Complex Composition A 150 µm ID 75 cm length capillary is etched according to Example 1. The capillary is then filled with a 65° C. 4% (v/v) solution of 3-aminopropyltriethoxysilane in methanol and reacted for 12 hours at a slow flow of 1 µL. After flushing with 100% methanol and then deionized water, the tube is filled with a 5.0 mg/mL NHS-LC biotin (N-hydroxysuccinimido-biotin, Sigma-Aldrich, Milwaukee, Wis., PN H1759) in 50 mM sodium bicarbonate solution pH 8.3 and reacted for 4 hours at room temperature. Following biotinylation the capillary is flushed with deionized water and then the capillary is filled with 4.0 mg/ml solution of streptavidin (Sigma-Aldrich, Milwaukee, Wis., PN S0677) in 50 mM sodium phosphate buffer (pH 7.3). The streptavidin solution is reacted for 4 hours at 40° C. and any remaining free streptavidin is removed by rinsing the capillary tube with deionized water.

DNA sequences being screened for their interactions with multi-protein complexes are prepared. In all cases the target sequence is biotinylated at its 5' end. An example of multi protein complexes are described in Eckhard Nordhoff, et al., Nature Biotech., 17:884 (1999). Short single-stranded biotinylated DNA (<50 bp) is prepared by standard DNA synthesis techniques (i.e. oligonucleotide synthesis). Long single-stranded biotinylated DNA (>50 bp) is prepared by standard PCR techniques, whereby one or both of the PCR primers is 5'-labeled with biotin. The primers are removed after the PCR reaction by standard purification techniques, including DNA Chromatography (Douglas Gjerde, et al., DNA Chromatography, Chapter 6, Wiley-VCH, Weinheim, Germany (2002)). The purified PCR product is then heated to >95° C. and then cooled immediately to 4° C. to produce single-stranded biotinylated DNA. Long double-stranded biotinylated DNA (>50 bp) is prepared in the manner identical to the single-stranded variety, except for elimination of the final heat denaturation and cooling step.

Once the biotinylated DNA of interest is suitably prepared, it is allowed to incubate with the proteins being screened for their DNA interactions. The proteins will most often be derived from whole-cell extracts, nuclear extracts, or any other source of DNA-binding proteins that have been prepared by standard means. Biotinylated DNA (100 ng) is added to the extract and is allowed to incubate in the manner described previously for extraction of DNA-binding proteins (Eckhard Nordhoff, et al., Nature Biotech., 17:884 (1999)). Once the incubation is complete, the unbound biotinylated DNA is removed from the sample by its selective precipitation with polyethyleneimine (PEI), in the manner described previously for the precipitation and removal of DNA (Jesper Svejstrup, et al., Proc. Natl. Acad. Sci. USA, 94:6075 (1997)). Once the unbound DNA is removed, the entire sample that contains the protein-bound biotinylated DNA is introduced into the streptavidin capillary described above. The entire sample is fully drawn up into and pushed out of the capillary at a flow rate of 50 µL/min, and this action is repeated 5 times. Once completed, the capillary is washed by separately drawing up and pushing out to waste 15 µL of water at 100 µL/min, and this action is repeated 5 times. The capillary is then evacuated by flowing 10 psi of air through the capillary for 30 seconds. A single 1 µL segment (approximately 5.6 cm in length) of 50% methanol/50% water is then fully drawn into the capillary, and passing this elution slug over the entire streptavidin surface a total of 5 times at 20 µL/min. The entire 1 µL elution volume that contains the eluted proteins bound to the original DNA sequence is then pushed into an electrospray nozzle (Advion NanoMateTMI 00, Advion BioSciences, Inc., Ithaca, N.Y.; Nanospray needle holder, PN NSI-01 and NSI-02, Nanospray needles, PN NSI-NDL-01 and NSI-NDL-02, LC Packings Inc., San Francisco, Calif.), which is in turn analyzed by ESI-MS/MS (examples of such electrospray nozzles, and their use with MS and MS/MS are described at Xian Huang, et al., Proceedings of the 50th ASMS Conference on Mass Spectrometry and Allied Topics, Orlando, Fla., Jun. 2-6, 2002. The ESI-MS/MS is then used for identification of the proteins that comprise the DNA-binding complex, in a manner described previously (Martin Yarmush, et al., Annu. Rev. Bionied. Eng., 4:349 (2002)).

Example 12

Recovery of Functional His-Tagged GST

Samples of his-tagged GST in an *E. coli* lysate were prepared at concentrations of 0, 2, 10 and 20 ug/mL. 0.5 mL aliquots were purified using a Ni-NTA extraction capillary. The purified samples were then detected on a bare gold grating SPR protein biochip using rabbit anti-GST antibody. The results, shown in the following table and reported in terms of resonance change units (RCU), indicates that the tagged GST is recognized by the antibody.

| GST-his concentration in lysate (ug/mL) | RCU |
|---|---|
| 0 | 0 |
| 2 | 13 |
| 10 | 25 |
| 20 | 35 |

Example 13

Bonding IDA, NTA, and CMA Chelating Groups to Fused Silica Capillary Channel

A 200 µm ID 100 cm length capillary is etched according to Example 1. The capillary is filled with a 100° C. solution of 10% (v/v) γ-glycidoxypropyl-trimethoxysilane (Sigma-Aldrich, Milwaukee, Wis., PN 44,016-7) in dry toluene and reacted for 1 hour at 10 µL/min. This treatment is repeated twice. The capillary is flushed with 100% HPLC grade methanol. To make IDA chelator, the epoxy bonded capillary is filled and reacted with a 65° C. solution of 10% (w/v) solution of iminodiacetic acid in methanol adjusted to pH 8.2 with lithium hydroxide for 4 hours at 10 µL/min. To make the NTA chelator, epoxy activated capillary is reacted with a 65° C. solution of 10% (w/v) solution of R-substituted nitrilotriacetic acid, either N-[3-amino-1-carboxypropyl]-iminodiacetic acid or N-[5-amino-1-carboxypentyl]-iminodiacetic acid, in methanol adjusted to pH 7.5 with lithium hydroxide for 4 hours at 10 µL/min. The synthesis procedures of R substituted NTA reagents are described in U.S. Pat. No. 4,877,830. For the carboxymethylated aspartate (CMA) metal chelate capillary channel, a solution of L-aspartic acid (100 mg/mL) is adjusted to pH 8.6 with sodium carbonate and pumped through the capillary channel at a rate of 5 µL/min at 30° C. for 12 hours. The capillary is washed with deionized water and a solution of bromoacetic acid (100 mg/mL) adjusted to pH 8.6 with sodium carbonate is pumped through the capillary channel at a rate of 5 µL/min at 30° C. for 12 hours. The capillary channel is washed with deionized water and is ready to be converted to the metal chelated form by pumping with a metal salt solution as described in U.S. Pat. No. 5,962,641. The excess epoxide groups are endcapped with a 1 M aqueous solution of ethanolamine for one hour at room temperature. Finally, the chelator capillary is flushed and stored in deionized water.

The chelator capillary is converted to the metal chelate form before use. This is accomplished by flushing the capillary with the appropriate metal salt solution. The capillary is flushed for 30 minutes each of 30 mM disodium EDTA and deionized water, and then flushed with either 0.2 M $ZnCl_2$, 0.2 M $NiCl_2$, $Hg(NO_3)_2.H_2O$ or $FeCl_3$ in 1 mM $HNO_3$ to convert the capillary to the Zn form, Ni form, or the Fe form respectively. The capillary is washed and stored with deionized water.

Example 14

Procedure for Immobilizing Protein G, Protein A, Protein A/G, and Protein L on a Fused Silica Capillary Channel A 200 µm ID 100 cm length capillary is etched according to Example 1. The capillary is filled with 10% w/v γ-glycidoxypropyltrimethoxysilane (Sigma-Aldrich, Milwaukee, Wis., PN 44,016-7) in dried toluene, and then the capillary is heated under slow flow conditions of 1 µL/min at 50° C. for 4 hours. The capillary is cooled, washed for 30 minutes each with toluene and methanol, and then deionized water. The capillary is filled with solution of protein G solution (5 mg/ml in 10 mM phosphate buffer, pH 7.5). The protein may be native Protein G (Calbiochem, San Diego, Calif., PN 539302-Y) which will attach through native lysine residues or recombinant Protein G from (Calbiochem, San Diego, Calif., PN 539303-Y) which will attach through a poly-lysine fusion tag at the protein terminus. The capillary is reacted by pumping the protein solution through capillary at 1 µL/min at 25° C. for 4 hours. The capillary is flushed and conditioned with 10 mM phosphate buffer solution pH 7.0 for 1 hour and then flushed and stored with deionized water at 4° C. until used.

In addition to Protein G, others, such as recombinant Protein L (Pierce, Rockford, Ill., PN 21189), recombinant Protein A (Calbiochem, San Diego, Calif., PN 539203-Y), and recombinant Protein A/G (Pierce, Rockford, Ill., PN 21186) may be used with the procedures described in this example.

Example 15

Immobilizing Single Strand and Double Strand DNA on Fused Silica Capillary Channels Using a Streptavidin Biotin Synthesis Reaction A 150 µm ID 75 cm length capillary is etched according to Example 1. The capillary is then filled with a 65° C. 4% (v/v) solution of 3-aminopropyltriethoxy-silane in methanol and reacted for 12 hours with a slow flow of 2 µL/min. After flushing with 100% methanol and then deionized water, the tube is filled with a 5.0 mg/mL NHS-LC biotin (Quanta BioDesign, Ltd., Powell, Ohio, PN 10206) in 50 mM sodium bicarbonate solution pH 8.3 and reacted for 4 hours at room temperature. N-hydroxysuccinimidobiotin (NHS-biotin), an alternative molecule, is also used (Quanta BioDesign, Ltd., Powell, Ohio, PN 10205; or Sigma-Aldrich, Milwaukee, Wis., PN H1 759). An NHS-biotin reagent containing a hydrophilic polyethylene glycol spacer (NHS-dPEG$_4$™-Biotin, Quanta BioDesign, Ltd., Powell, Ohio, PN 10200) is used under the same reaction conditions as the other biotin reaction reagents.

Following biotinylation the capillary is flushed with deionized water and then the capillary is filled with 4.0 mg/ml solution of streptavidin (Sigma-Aldrich, Milwaukee, Wis., PN S0677) in 50 mM sodium phosphate buffer (pH 7.3). The streptavidin solution is reacted for 4 hours at 4° C. and any remaining free streptavidin is removed by rinsing the capillary tube with deionized water. The streptavidin capillary is stored in a refrigerator until the final attachment of the biotinylated DNA.

In some cases, single-stranded DNA is immobilized to the wall of the capillary by quickly heating the biotinylated double-stranded DNA PCR product to 95° C. for several minutes followed by rapid cooling to 5° C. and immediately pumping the solution into the reactor. Excess template is removed by rinsing with deionized water. The deionized water may be heated to ensure complete denaturing of the DNA and retention of single-stranded DNA. Alternatively biotinylated single-stranded DNA may be prepared and purified and then introduced into the streptavidin capillary. Double-stranded DNA is immobilized to the wall of the capillary by pumping biotinylated double-stranded DNA PCR product without prior heating.

Example 16

Figure 8:
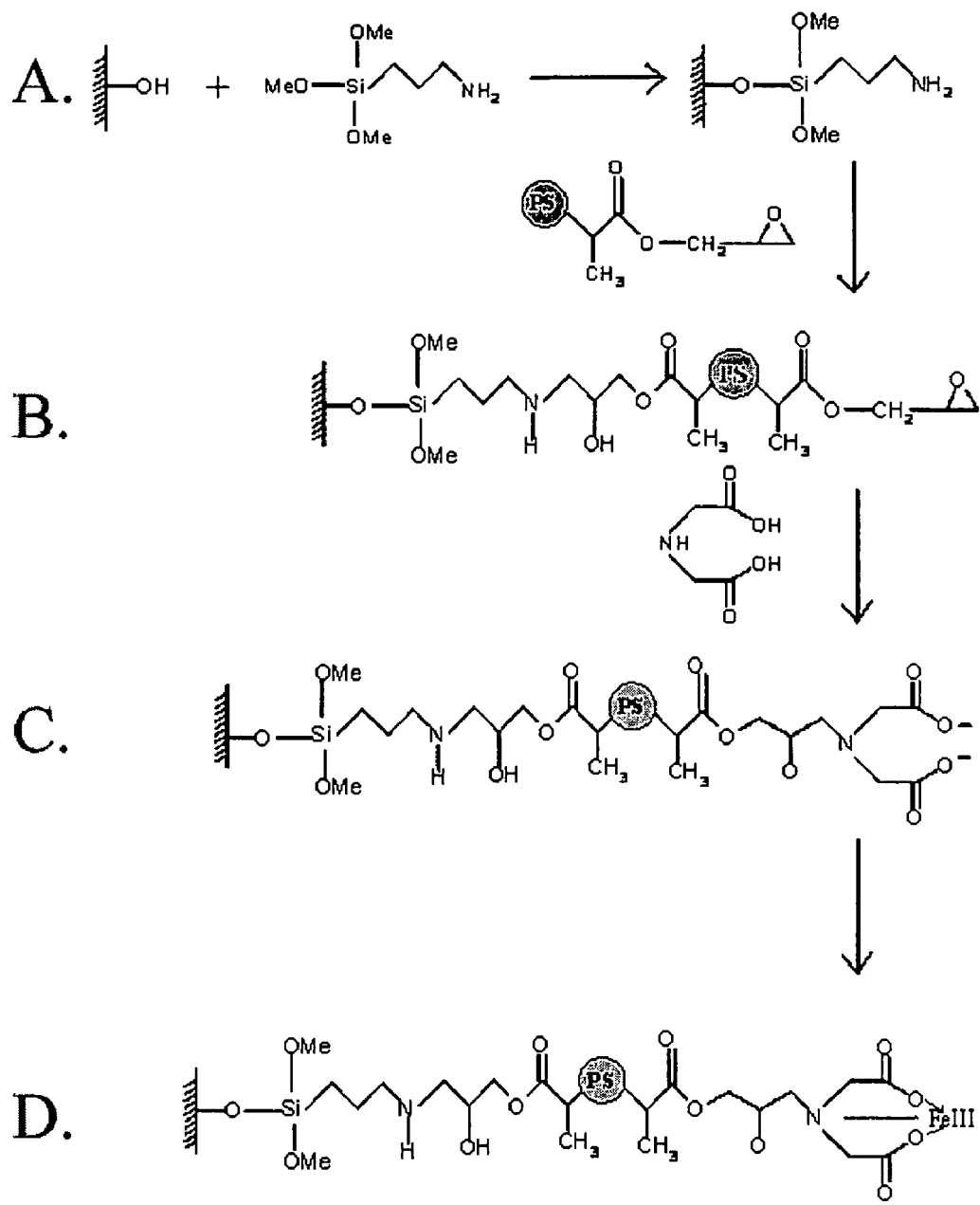
FIG. 8 shows the reactions used to coat a capillary using covalent attachment of latex particles as described in Example 20.

Purifying A (His)$_6$ Fusion Protein Integrated with Arraying the Protein onto a Protein Chip A capillary of dimensions 25 cm×100 μm ID is functionalized with an NTA-Ni(II) chelator bonded according to the procedure described in Example 33. The capillary is coiled in a "FIG. 8" type configuration with 6 mm diameter coils with 5 cm straight sections on the top and bottom of the configuration. The capillary is connected to a syringe pump (Tecan Systems, San Jose, Calif., CAVRO Model No. XP-3000) fitted with 100 μl or 1 mL syringe connected to one end of the open tube capillary, and the other end is movable and is connected to an apparatus where the materials may be taken up or deposited at different locations. The capillary is conditioned by drawing up 20 mM sodium phosphate, 0.5 M sodium chloride, 10 mM imidazole, pH 7.4 at the rate of 25 μL/min for 2 minutes. The buffer is expelled and the capillary is filled with a 100 μL sample of clarified whole-cell lysate of E. coli expressing a fusion protein with a His$_6$ tag and a terminal cysteine residue. The sample is drawn repeatedly over the capillary surface at the rate of 25 μL/min so that the total 100 μL sample passes back and forth 3 times for a total of 6 passes over the capillary surface. The remaining sample is blown out of the capillary with 3 psi air, and 10 μL of standard PBS (0.9% w/v NaCl, 10 mM sodium phosphate, pH 7.2) wash buffer is drawn into and out of the capillary at a rate of 25 μL/min. This is done for a total of 3 cycles over the capillary surface, and the remaining wash solution is blown out of the capillary with 3 psi air. A small plug, 50 nL (approximately 7 mm in length), of desorption buffer, 20 mM sodium phosphate, 0.5 M sodium chloride, 0.5 M imidazole, pH 7.4 is drawn into the capillary, and is passed over the capillary surface a total of six times at a rate of 5 μL/min. This elution plug is positioned at the opening of the capillary column, and a portion (10 nL) is deposited on a bare gold grating-coupled SPR chip for covalent attachment through the terminal cysteine's thiol group. Attachment of proteins to gold surfaces via cysteine residues, along with descriptions of collecting GC-SPR data from these surfaces, has been described previously. (Jennifer Brockman et al., Poster Presentation "Grating-Coupled SPR," *Antibody Engineering Conference*, Dec. 2-6, 2001, San Diego, Calif.).

Example 17

Purifying a Monoclonal Human IgG Protein

A capillary of dimensions 35 cm×100 μm ID is functionalized with an extraction phase on a capillary of recombinant Protein G bonded according to the procedure described in Example 34. The capillary is a straight configuration where one end is movable and connected to a pumping means and the other end is movable and connected to an apparatus where the material may be taken up or deposited at different locations. The pumping means is a 200 μL vial that may be filled with conditioning fluid, sample, washing fluid or nitrogen gas. The vial is filled with the various fluids by draining and forcing the old fluid out and then refilling with the new fluid several times until the vial is rinsed and ready for use. The vial is pressurized to force fluids through the capillary usually at a pressure of 0.1 to approximately 300 psi depending on the diameter and length of the capillary. For this capillary, a pressure of 3 psi is used.

The capillary is conditioned with 100 mM sodium phosphate, 100 mM sodium citrate, 2.5 M sodium chloride, pH 7.4 at the pressure of 3 psi for 10 minutes. The buffer is expelled and the capillary is pumped with 300 μL hybridoma cell culture supernatant sample (preferably, but not necessarily, free from fetal bovine serum) containing monoclonal human IgG. The capillary is washed with 100 mM sodium phosphate, 100 mM sodium citrate, 2.5 M sodium chloride, pH 7.4 at the pressure of 3 psi for 10 minutes. The washing step may be omitted in cases where the enrichment is high and a small amount of residual sample material can be tolerated.

The wash solution is blown out of the capillary and a small plug, 50 nL (approximately 7 mm in length), of desorption buffer of 100 mM sodium phosphate, 100 mM sodium citrate, pH 3.0 is pumped through the capillary and deposited directly into a vial containing 40 nL of neutralization buffer of 100 mM H$_2$NaPO$_4$/100 mM HNa$_2$PO$_4$, pH 7.5. Alternatively, the desorption solution is introduced as a stream rather than a segment of liquid. The desorption process is performed so that the leading edge of the stream contains the desorbed material and the first 2 cm length of the stream (150 nL) is directed and deposited in directly into a vial containing 40 nL of neutralization buffer of 100 mM H$_2$NaPO$_4$/100 mM HNa$_2$PO$_4$, pH 7.5. The remaining portion of the stream is directed to waste. Alternatively, the leading edge desorption process is performed directly into the wash buffer or the sample. The desorption buffer containing 100 mM sodium phosphate, 100 mM sodium citrate, adjusted to pH 3.0 is pumped into the capillary containing residual wash buffer or sample. In this example, for the rate at which the desorption buffer is pumped into the capillary, it will take 5.0 minutes for the leading edge to start to exit the end of the tube. The sample or wash in the capillary is directed to waste. Then, the flow for the time segment of 5.0-5.3 minutes is directed and deposited directly into a vial containing 40 nL of neutralization buffer of 100 mM H$_2$NaPO$_4$/100 mM HNa$_2$PO$_4$, pH 7.5. The remaining portion of the stream is directed to waste.

Alternatively, a Protein L capillary channel as described in Example 34 can be used in this example.

Example 18

Purifying a Monoclonal Human IgG Protein with Arraying onto a Protein A-Functionalized Protein Chip A capillary of dimensions 100 cm×200 μm ID is functionalized with an extraction phase on a capillary of recombinant Protein G bonded according to the procedure described in Example 34. The capillary is a straight configuration where one end is movable and connected to a pumping means and the other end is movable and is connected to an apparatus where the material may be taken up or deposited at different locations. The pumping means is a 200 μL vial that may be filled with conditioning fluid, sample, washing fluid or nitrogen gas. The vial is filled with the various fluids by draining and forcing the old fluid out and then refilling with the new fluid several times until the vial is rinsed and ready for use. The vial is pressurized to force fluids through the capillary usually at a pressure of 0.1 to approximately 300 psi depending on the diameter and length of the capillary. For this capillary, a pressure of 3 psi is used.

The capillary is conditioned with 100 mM sodium phosphate, 100 mM sodium citrate, 2.5 M sodium chloride, pH 7.4 at the pressure of 3 psi for 10 minutes. The buffer is expelled and the capillary is pumped with 1,000 μL hybridoma cell culture supernatant sample (preferably, but not necessarily, free from fetal bovine serum) containing monoclonal human IgG. The capillary is washed with 100 mM sodium phosphate, 100 mM sodium citrate, 2.5 M sodium chloride, pH 7.4 at the pressure of 3 psi for 10 minutes. The washing step may be omitted in cases where the enrichment is high and a small amount of residual sample material can be tolerated.

The wash solution is blown out of the capillary and a small plug, 2 μL (approximately 6.4 cm in length) of desorption buffer of 100 mM sodium phosphate, 100 mM sodium citrate, adjusted to pH 3.0 is pumped into the capillary. This segment of fluid is passed over the inner capillary surface a total of five (5) times at flow rate of 30 μL/min. The complete segment is then deposited directly into a 384-well plate where an individual well contains 2 μL of neutralization buffer of 100 mM $H_2NaPO_4$/100 mM $HNa_2PO_4$, pH 7.5. The sample is then arrayed by available means onto a Protein A-coated grating-coupled SPR (GC-SPR) chip, for subsequent analysis of target binding to the antibody. The apparatus, procedures and conditions used for preparation of the Protein A-coated GC-SPR chip, arraying of the chip, and collection of the associated SPR data have been described (Jennifer Brockman et al., Poster Presentation "Grating-Coupled SPR," *Antibody Engineering Conference*, Dec. 2-6, 2001, San Diego, Calif.).

Alternatively, a Protein L capillary channel as described in Example 34 can be used in this example.

Example 19

Phage Display Screening of Fab Antibody Fragments with Label-Free Grating-Coupled SPR Phage-derived clones for different Fab antibody fragment sequences are released as whole-cell bacterial lysates, where there are two fusion tags on the Fab antibody fragment—one c-myc (for purification) and the other a terminal cysteine residue (for immobilization). The clarified lysate is passed through an open-tube separation capillary (Polymicro Technologies, Phoenix, Ariz.) of dimensions 200 μm ID and 60 cm with Protein G, as described in Example 34, immobilized on its surface, and an anti-c-myc monoclonal or polyclonal antibody is bound by the Protein G (a bifunctional linker covalently attaches the antibody to the Protein G; the bifunctional linker is dimethylpimelimidate (DMP); procedure for successful crosslinking are provided within "ImmunoPure Protein G IgG Orientation Kit" instructions (Pierce, Rockford, Ill., PN 44896). Once the Fab antibody fragment is trapped by the anti-c-myc antibody on the inside tube wall, a very small volume slug (1 μL) of 10 mM phosphoric acid (pH 2.3) is introduced to the tube, and is moved back and forth across the internal walls to desorb the Fab antibody fragment from the immobilized anti-c-myc. This is ejected from the tube into 250 nL of phosphate neutralization buffer (100 mM $H_2NaPO_4$/100 mM $HNa_2PO_4$, pH 7.5), bringing the pH to ~7.0. This is then ready for covalent spotting onto a grating-coupled surface plasmon resonance array (GC-SPR), where the surface chemistry is based upon the terminal cysteine's thiol group bonding with the gold surface of the GC-SPR chip. In addition, the desorption/neutralization process can be performed within the spotting apparatus itself so that the Fab antibody fragments are fully processed as part of a larger integrated chip preparation process.

In addition to Protein G, Protein A or Protein A/G (as described in Example 34) may be used in the procedures described in this example.

Example 20

Synthesis of a Coated Capillary Using Covalent Attachment of Latex Particles

A 200 μm ID 1 m fused silica capillary was rinsed and filled with 1.0 M NaOH. The capillary ends were sealed and heated at 100° C. for 2 hour in the oven. After cooling to room temperature, the two ends of the capillary were opened and the capillary was washed with 0.1 M HCl for 10 min, deionized water 10 min and acetone 15 min at 4 bar nitrogen pressure. Subsequently, the capillary was placed again in the oven at 120° C. and purged with nitrogen for 1 hour to remove residual water and acetone. A solution of 5% v/v (3-aminopropyl)trimethoxysilane in dry toluene was prepared, de-aerated with helium for 15 min and filled into the pretreated capillary. After both ends were sealed the capillary was placed in the oven at 100° C. for 6 hours. Thereafter, the capillary was taken out, washed extensively with toluene, acetone and blown dry with nitrogen. The capillary was flushed with a polystyrene epoxy latex suspension (100 nm purchased from Micromod Partikeltechnologie GmbH (Rostock-Warnemuende, Germany) diluted 1:1 with borate buffer pH 8.5 for 1 hour at room temperature. The filled capillary is sealed, left to react overnight at room temperature (FIG. 8A-8B), and then the capillary was washed with deionized water to remove excess latex particles. The coated capillary was filled with iminodiacetic acid (IDA) solution (FIG. 8B-8C) prepared by dissolving 0.5 g IDA in 25 ml of a 2M $Na_2CO_3$ solution (pH 10.5) containing 250 mg NaCl. The capillary ends were sealed and heated overnight in a water bath at 70° C., and then the capillary was taken out and washed thoroughly with deionized water. The capillary was charged with 200 mM $FeCl_3$ solution containing 0.1 M HCl (FIG. 8C-8D). The excess $Fe^{3+}$ was removed by washing with deionized water.

FIG. 9A shows a scanning electron micrograph used to see the morphology of the coated capillary at 10,000×. The particles are bonded as a dense monolayer to the capillary wall. FIG. 9B is a schematic diagram of the capillary inner wall.

Example 21

Tryptic Digest and Solid Phase Extraction of Phosphopeptides from β-Casein

β-casein was chosen as a model compound due to its commercial availability and its well-characterized five phosphorylation sites (W. Zhou et al. (2000), J. Amer. Soc. Mass Spec. 11:273). Sequencing grade modified trypsin 20 µg was dissolved in 200 µl of 50 mM acetic acid buffer and incubated at 37° C. for 30 min. Trypsin solution was added to 1 mg of β-casein in 800 µl of water, incubated at 37° C. for 16 hours. The digest was stopped by adding 25 µl trifluoroacetic acid (TFA) 2.5% (v/v) and put in the freezer at 20° C.

A capillary of dimensions 200 µm ID and 100 cm length functionalized with IDA and chelated with $Fe^{3+}$ (as described in Example 20) was connected to an ME100 (PhyNexus, Inc., San Jose, Calif.) fitted with a 100 µl syringe. The capillary was flushed and conditioned with 0.1% acetic acid containing 10% acetonitrile (ACN). 100 µl of β-casein tryptic digest was passed through the capillary six times. The capillary was washed twice with 0.1% acetic acid containing 20% ACN. The capillary was then washed with water and the solution blown out. Phosphopeptides were eluted with 20 µl freshly prepared 0.3 N ammonium hydroxide. The solutions were moved inside the capillary forward and backward about six times.

0.5 ul of the eluted peptides were deposited on a MALDI target and air dried at room temperature. 0.5 ul of dihydroxybenzoic acid (DHB) was added and the peptides were analyzed by a MALDI-TOF/TOF (Bruker, Germany).

Figure 10:
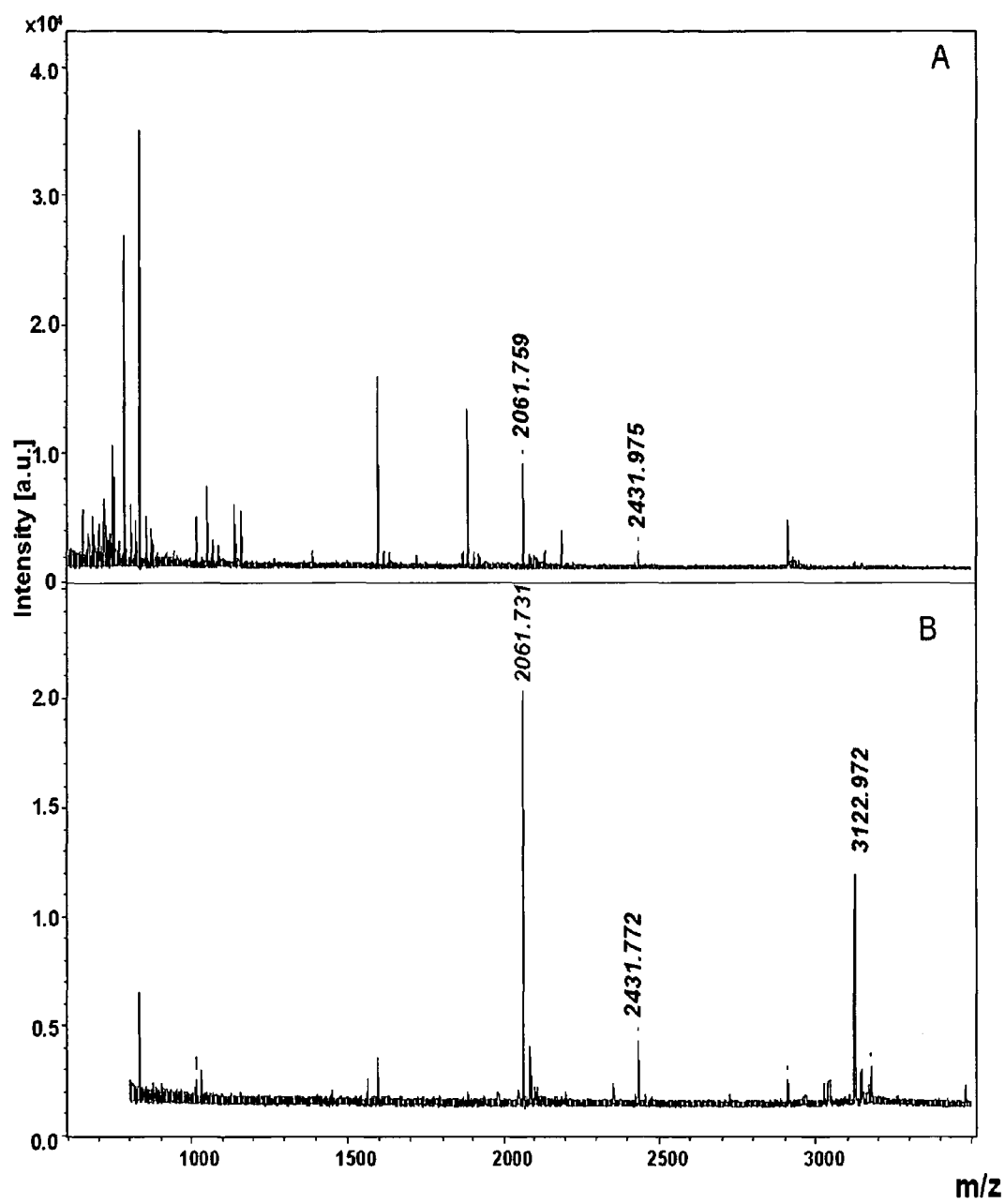
FIG. 10 shows a MALDI-TOF of β-casein tryptic digest before and after separation as described in Example 21.

FIG. 10A shows the recorded MALDI-TOF mass spectrum of the digest prior to solid phase extraction (SPE). Using the latex coated capillary derivatized with IDA-$Fe^{3+}$ as a stationary phase for SPE of phosphopeptides, the high selectivity is based on the interaction between the negatively charged phosphate groups and the positively charged iron bound to the stationary phase. From FIG. 10B, the MALDI-TOF mass spectrum after SPE can be deduced. In addition to the phosphopeptides peaks at m/z=2061.73 and 3122.97, other phosphopeptide peaks at m/z 2431.77 were observed. This experiment demonstrated that relatively large phosphopeptides, in the range 2000-3500 Da, could be purified and characterized by this method.

Figure 11:
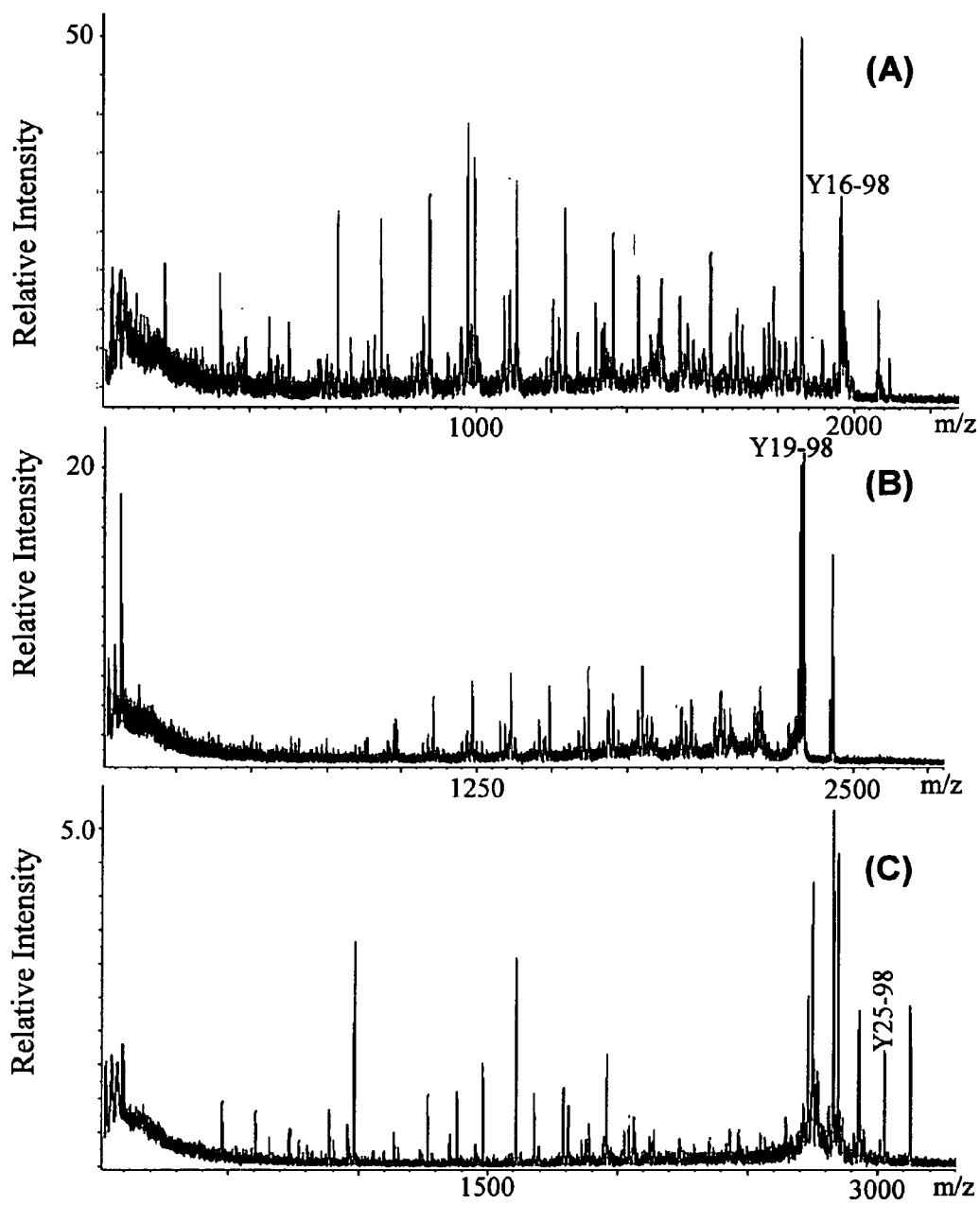
FIG. 11 shows the MALDI-TOF/TOF of the phosphopeptides from β-casein tryptic digest with m/z A) 2061.72 Da B) 2431.93 Da and C) 3122.179 Da as described in Example 21.

FIG. 11A shows the fragmentation pattern of m/z=2061.73 obtained by MALDI-TOF/TOF mass spectrometry, which corresponds to FQpSEEQQQTEDELQDK. The observed fragments can be correlated to the loss of $H_3PO_4$ (MH-98)+ and the loss of $HPO_3$ (MH-80)+. These fragment ions indicate that the peptide is phosphorylated on its serine residue. The MALDI-TOF/TOF spectrum of the tetraphosphorylated peptide RELEELNVPGEIVE pSLpSpSpSEESITR shows apparent losses of phosphoric acid groups from the precursor ion (successive losses of 98 Da from the precursor ion). In addition the peak at m/z 2431.77 a monophosphorylated peptide IEKFQpSEEQQQTEDELQDK was also subjected to fragmentation with MS/MS as shown in FIGS. 11C and 11B.

Example 22

Tryptic Digest and Enrichment of Phosphopeptides from Myoglobin

20 µg of myoglobin was dissolved in 50 mM Tris HCl, and denatured at 95° C. for 5 min. A trypsin solution was prepared as described in Example 21 and the myoglobin was digested at 37° C. for 20 hours and the digest was stopped by adding 50 µl TFA 5% (v/v).

The myoglobin tryptic digest and two synthetic phosphopeptides were mixed 1:1 with 0.1% acetic acid containing 10% CAN. 50 µl of this solution was loaded on an equilibrated IDA-$Fe^{3+}$ capillary channel. The non-phosphorylated peptides were washed with 100 µl 0.1% acetic acid containing 25% ACN, and processed as described in Example 21.

Figure 12:
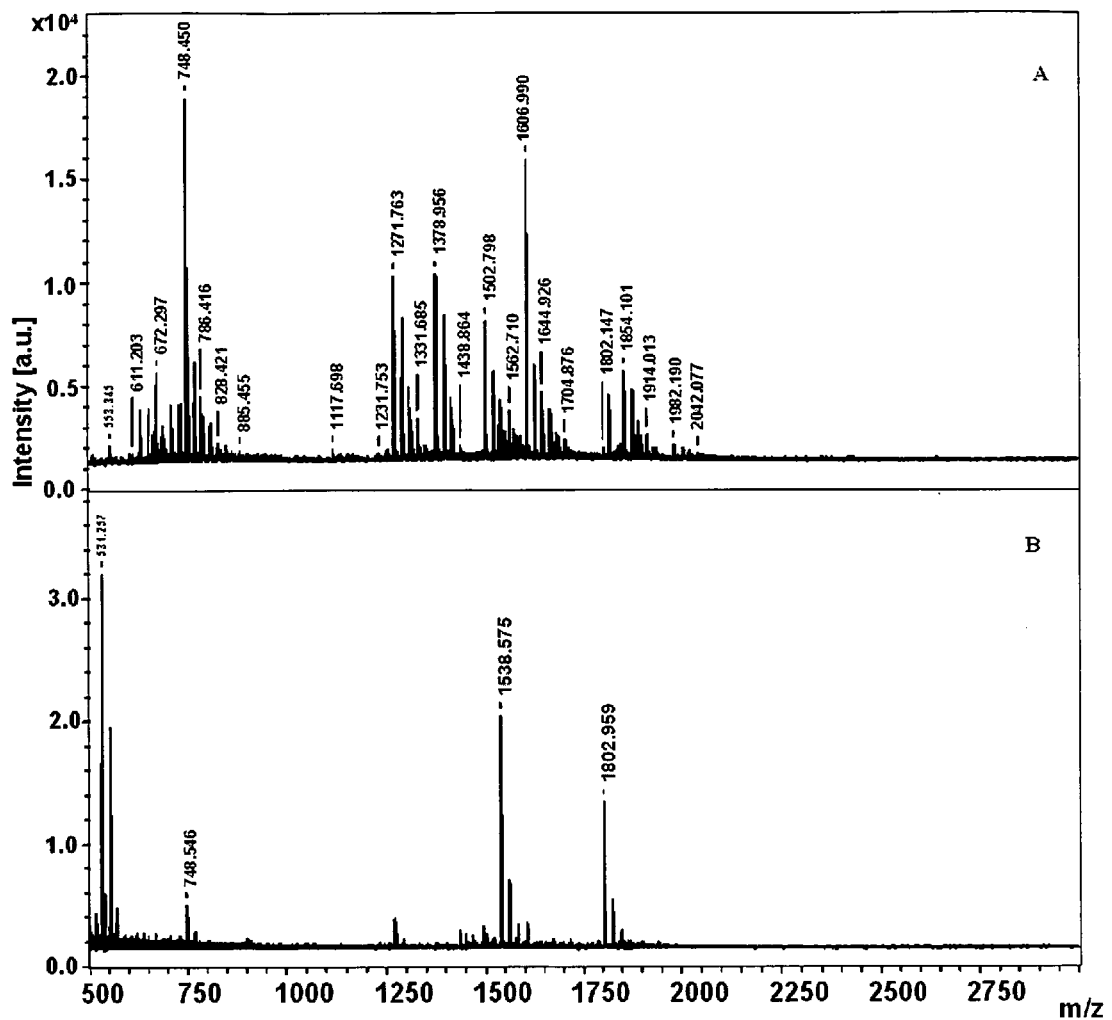
FIG. 12 B shows the elution of phosphopeptides from open-tubular latex coated capillary IDA-$Fe^{+3}$ as described in Example 22.

A 5 pmol/µl solution of a tryptic peptide mixture derived from the in-solution digest of myoglobin was mixed with 500 fmol/µl of two synthetic peptides TTPSFVGFTDpTER m/z=1537.657 and SFDVPPIDASSPFpSQK m/z=1801.80 (Bachem GmbH, Weil am Rhein, Germany). This setup allowed a quantitative simulation of a tryptic digest of a large in vivo phosphorylated protein where 10% of a given residue is phosphorylated. FIG. 12A shows MALDI-TOF mass spectrum of the myoglobin tryptic digest spiked with the two phosphopeptides. As shown in the figure it was difficult to detect the two phosphopeptides prior to IMAC enrichment. The signal of the phophopeptides that are suppressed in MALDI-TOF analysis by their non-phosphorylated counterpart without prior enrichment of the phosphorylated peptides became detectable after solid phase extraction (FIG. 12B).

Phosphopeptide recovery was quantified by using RP-µLC-ESI-MS on a quadrupole ion trap instrument. The peptides were separated on a monolithic capillary column directly connected to spray capillary. A constant amount of the synthetic phosphopeptide was added to the mixture after purification and to the original mixture solution. Abundances were calculated by integration of peak areas after subtraction of the baseline. The relative abundance of the internal standard was used to normalize abundances. The recovery was found to be in range between 92-95%.

Example 23

Synthesis of a Protein G Immobilized Capillary

A 200 µm ID 1 m fused silica capillary was prepared with covalently bound latex particles as described in Example 20. The coated capillary was flushed with 100 mM $Na_2CO_3$ for 1 hour at 0.5 bar.

In these experiments, a recombinant form of protein G that lacks the albumin binding region of the native molecule was used, leaving two IgG binding sites that can bind all subclasses of bovine IgG. The capillary was filled with 5 mg/ml protein G in 100 mM $Na_2CO_3$ solution, both ends were sealed and left overnight in water bath at 40° C., and then the capillary was taken out and washed thoroughly with $Na_2CO_3$ solution for 30 min followed by deionized water. The capillary was washed with 1 M ethanolamine for 1 h at 0.5 bar, and then washed with deionized water.

Example 24

Purification of Bovine IgG with a Protein G Immobilized Capillary

Figure 13:
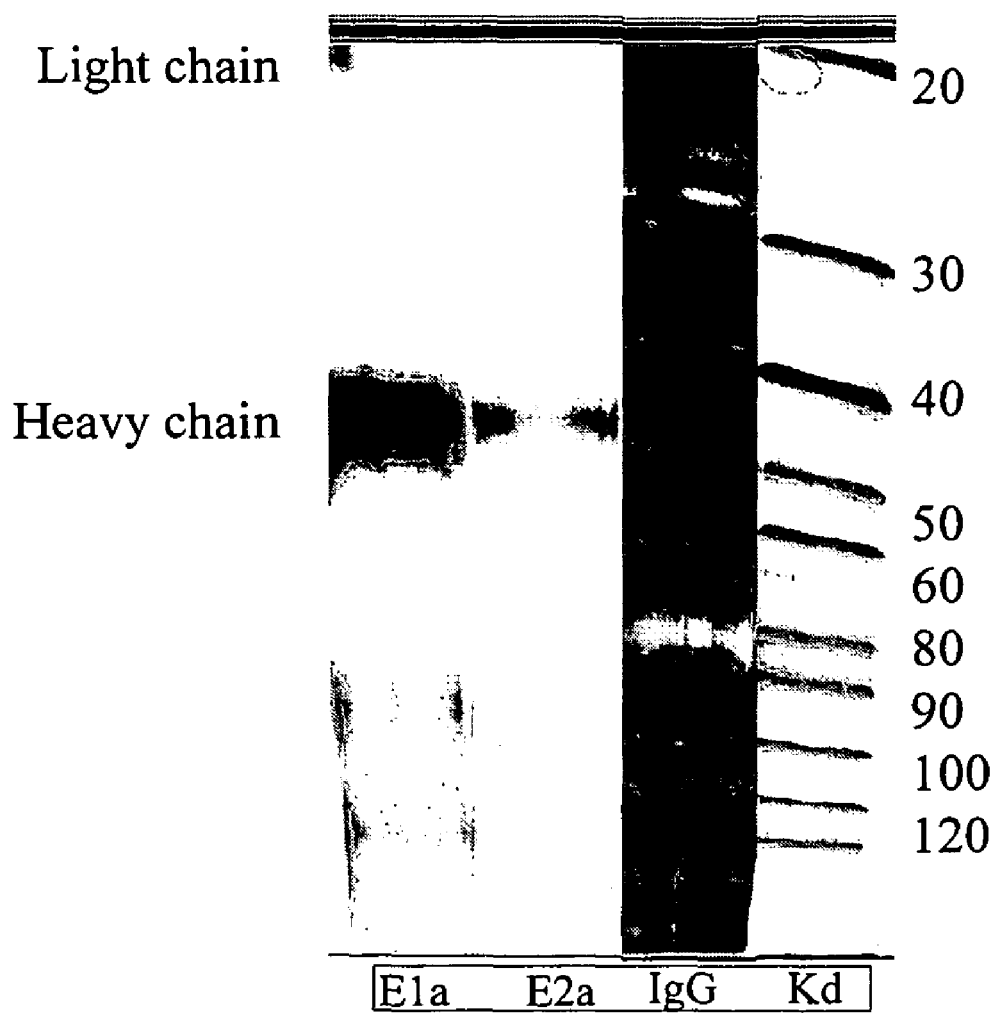
FIG. 13 is an SDS-PAGE of the results of purification of IgG using protein G immobilized coated capillary in example 24. Lane 1: IgG protein from sigma; lane 2: first elution fraction; lane 3: second elution fraction; lane 4: molecular weight marker.

Experiments were conducted to selectively purify bovine IgG. The capillary described in Example 23 was connected to an ME100 (PhyNexus, Inc., San Jose, Calif.) fitted with a 100 µl syringe. To immobilize protein G to the capillary wall, an aliquot of recombinant protein G in 100 mM Na2CO3 was loaded to the epoxy derivatized latex coated capillary and allowed to react overnight. Unattached protein G was washed off and then the capillary was treated with ethanolamine to block the unreacted active sites to avoid unspecific protein adsorption. Immobilized protein G capillary was then loaded with 10 μg (~68 pmol) of bovine IgG purchased from sigma in PBS buffer. The capillary was washed with PBS buffer. The bound IgG was eluted with 10 mM HCl solution of pH 2.5. The eluted solution was analyzed with gel electrophoresis and visualized by SDS-PAGE with silver staining. FIG. 13 shows the silver stained SDS-gel of IgG protein before and after purification with the protein G capillary. Lane 1 shows the IgG protein and lanes 2,3 show the first and second elution fractions from the protein G immobilized capillary. The heavy and light chains can be easily identified.

Example 25

Synthesis of a Lectin Con-A Immobilized Capillary

A coated capillary was prepared as described in Example 20 and flushed with acetate buffer (50 mM Sodium acetate containing 0.1 mM $MgCl_2$ and 5% Mannose) pH 5.8 for 1 hour at 0.5 bar. Then the capillary was filled with 5 mg/ml concanavalin A in acetate buffer, both ends were sealed and left overnight in water-bath at 40° C., and then the capillary was taken out and washed thoroughly deionized water. The capillary was flushed with 1 M ethanolamine for 1 h at 0.5 bar, then washed with deionized water. Before use the capillary was washed with 0.1 M Tris_HCl pH 8.5 containing 0.5 M NaCl, followed with washing with 0.1 M Sodium acetate pH 4.5 containing 1 M NaCl (to remove excess mannose) followed by deionized water. Then the capillary was equilibrated with TBS buffer (20 mM Tris HCl+0.5 mM NaCl) pH 7.5.

Example 26

Synthesis of an Anion Exchange Capillary

A 75 μm ID 1 m fused silica capillary was rinsed and filled with 1.0 M NaOH. The capillary ends were sealed and heated at 100° C. for 2 hours in the oven. After cooling to room temperature the two ends of the capillary were opened and the capillary was washed with 0.1 M HCl for 10 min, deionized water 10 min and acetone 15 min at 4 bar nitrogen pressure. Subsequently the capillary was placed again in the oven at 120° C. and purged with nitrogen for 1 hour to remove residual water and acetone. A solution containing 50% (v/v) γ-(trimethoxysilyl)propyl methacrylate and 0.01% (w/v) DPPH in DMF was prepared, deareated with helium for 15 min and filled into the pretreated capillary. Then after both ends were sealed it was placed in the oven at 120° C. for 6 hours. The capillary was then taken out and washed extensively with DMF, methanol and methylene chloride, and was blown dry with nitrogen. After that an aqueous solution of 2-acrylamido-2-methyl-1-propanesulfonic acid (10%, w/w) was prepared, neutralized with sodium hydrogen carbonate and then 0.1% (w/v) of potassium persulfate was added to the solution. The silanized capillary was filled with the above prepared solution. After both ends were sealed, the capillary was heated in the oven at 90° C. for 6 hours. Then it was washed with deionized water, methanol and dried with a nitrogen stream. The capillary was flushed with an anion exchange latex suspension (quaternary ammonium derivatized latex particles) for 1 hour at room temperature at 2 bar. Then the capillary was washed with deionized water to remove excess latex particles.

Example 27

Purification of Glycoprotein with a Lectin Con-A Immobilized Capillary

The coated capillary was prepared as described in Example 25 and activated with metal solution (1 M NaCl, 5 mM $MgCl_2$, 5 mM $MnCl_2$, and 5 mM $CaCl_2$) followed by equilibrating with TBS buffer (20 mM Tris HCl+0.5 mM NaCl) pH 7.5. 100 μl of protein sample was loaded with a flow rate of 50 μl/min with four draw/expel cycles. The capillary was subsequently washed tree times with TBS. The bound glycoprotein was eluted with 25 μl of 0.5 M methyl-alpha-D-mannopyranoside. The eluted solution was subsequently analyzed by gel electrophoresis and visualized by SDS-PAGE with silver staining or with MALDI/TOF using sinapinic acid or DHB as a matrix.

Example 28

Purification of His-Tagged Proteins from an *E. Coli* Lysate

Figure 14:
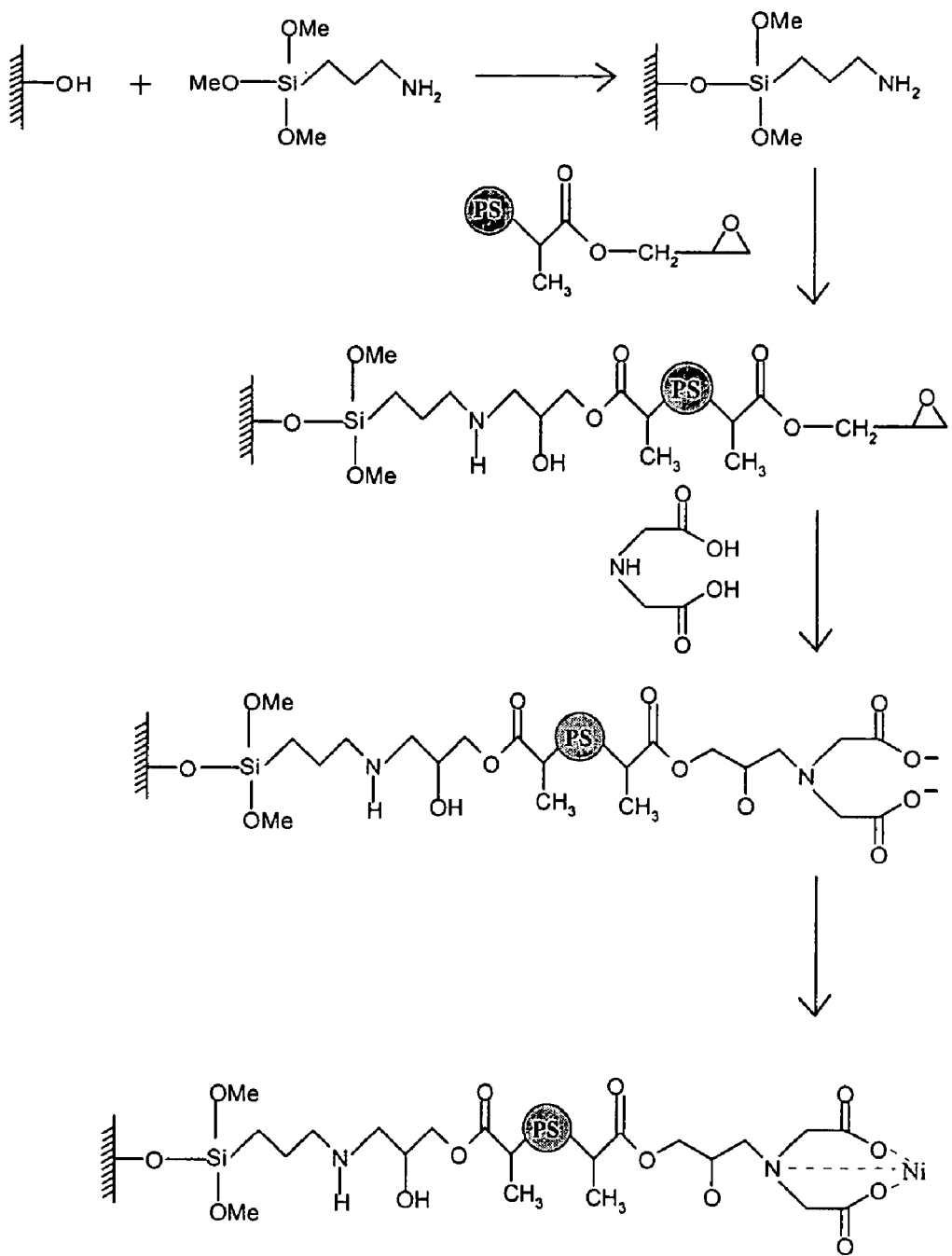
FIG. 14 depicts the reactions used to coat a capillary using covalent attachment of $Ni^{2+}$-IMAC as described in Example 28.

IDA chelate provides coordination with nickel, while still presenting two nickel coordination sites for efficient complexing with recombinant fusion proteins containing histidine. The scheme for the preparation of the IMAC capillary is demonstrated in FIG. 14.

The latex coated capillary was prepared as described in Example 20 and filled with iminodiacetic acid solution prepared by dissolving 0.5 g IDA in 25 ml 2 M $Na_2CO_3$ solution (pH 10.5) containing 250 mg NaCl. The capillary ends were sealed and heated overnight in water bath at 70° C., followed by thorough washing with deionized water. The capillary was washed with 0.1 M $NaHCO_3$ then blown up with $N_2$. The capillary was charged with 10 mM $NiSO_4$ solution. The capillary was washed with deionized water followed by 10 mM NaCl and finally with water.

The latex-coated Ni-IDA capillary was used to purify a His-tagged protein from an *E. coli* whole cell lysate. The capillary was equilibrated with PBS buffer (20 mM phosphate buffer containing 120 mM NaCl) pH 7.4 containing 5 mM imidazole. Clarified *E. coli* cell lysate (400 μl) containing over-expressed 6×His-tagged MP1 fusion protein was loaded to the capillary column with four times draw/expel cycles. 5-10 mM imidazole in the equilibration/loading buffer was utilized to eliminate adsorption of weakly bound proteins. The capillary was washed two times with 500 μl of PBS buffer containing 10 mM imidazole with a flow rate 100 μl/min. The capillary was blown with nitrogen for 1 min at 0.5 bar. After washing out the non adsorbed or weakly adsorbed proteins, the imidazole concentration was increased to 120 mM to elute the adsorbed His-tagged protein. The His-tagged protein was eluted with 20 μl PBS solution containing 120 mM imidazole for gel electrophoresis with SDS-PAGE or with 20 μl of 0.1% TFA for the MALDI measurement using sinapinic acid as matrix.

Figure 15:
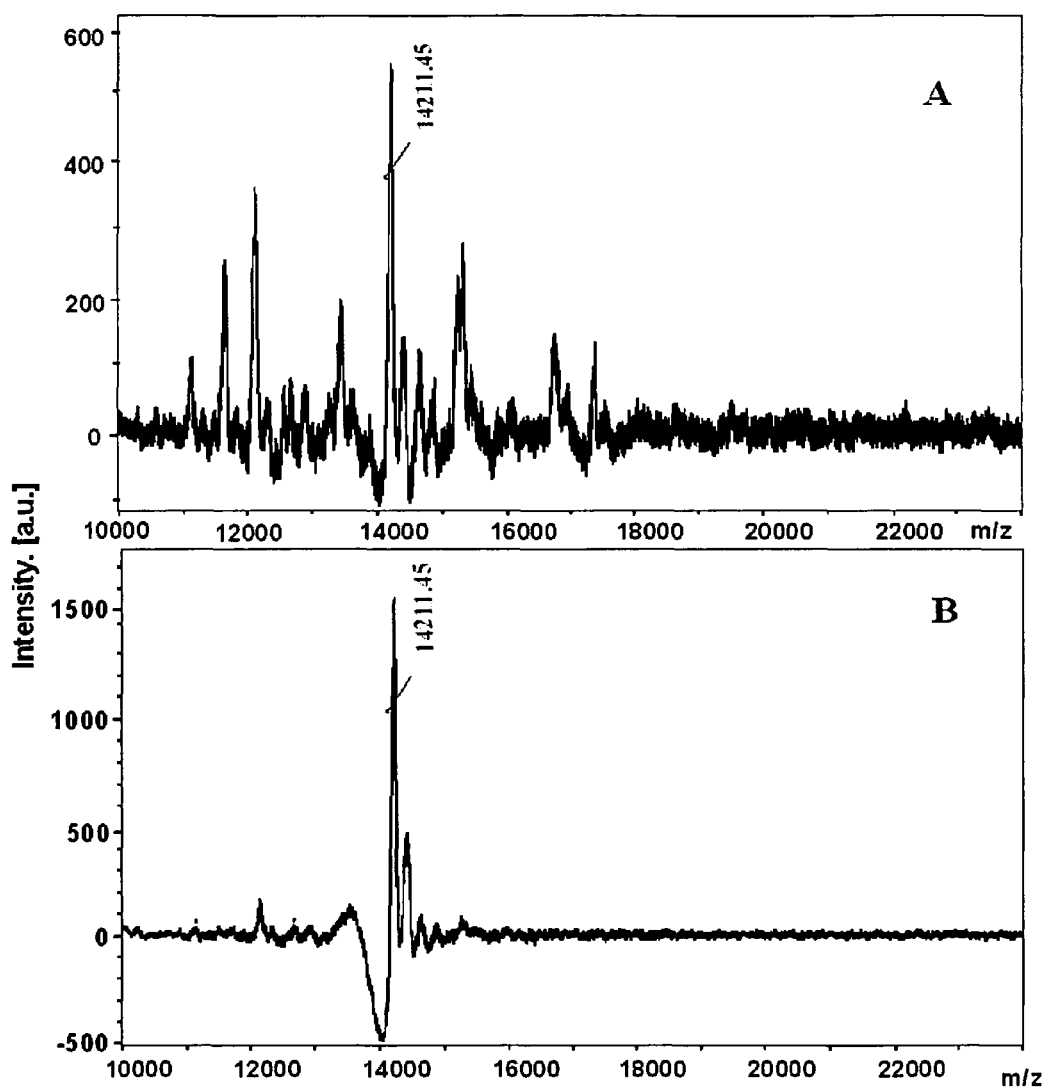
FIG. 15A is a MALDI-TOF of a clarified *E. coli* whole-cell lysate in example 28.
FIG. 15B shows the target His-tagged MP1 protein purified by open-tube latex coated capillary Ni-IDA.

The eluted solution was visualized by SDS-PAGE and stained with silver based staining. SDS-PAGE profile of the fraction revealed a high enrichment of the His-tagged protein (data not shown). Alternatively, eluted protein can be directly spotted onto a target for MALDI-TOF/MS analysis. In this case the his-tagged protein was eluted with 20 μl 0.1% TFA. The eluted solution was directly spotted on a MALDI target and measured with MALDI-MS using sinapinic acid solution (saturated solution in 0.1% TFA in 50% ACN) as matrix. FIG. 15A shows the MALDI-MS spectra of the crude cell lysate containing the His-tagged MP1 protein. FIG. 15B demonstrates the MALDI-MS of affinity purified his-tagged MP1 protein. The results gave only one peak at the expected mass for the His-tagged protein m/z 14221.45. It was possible to digest the eluted protein and the resulting peptide could be identified with the peptide mass fingerprinting.

Example 29

Determination of the Binding Capacity of the IMAC Capillary

Inductively coupled plasma was used to determine the binding capacity of the IMAC capillary. The capillary was washed with sodium chloride solution to remove non-specifically bound nickel ions. The bound nickel was stripped from the IMAC capillary using 0.1 M EDTA and determined with inductively coupled plasma mass spectrometry (ICP-MS). The metal capacity of the IMAC column (1 m-200 µm ID) was found to be 22.4±2.8 pmol. The binding capacity was calculated with the assumption of 1 histidine bound to 1 nickel atom.

Example 30

Tryptic Digest of Ovalbumin and Extraction with an IMAC Capillary

Figure 16:
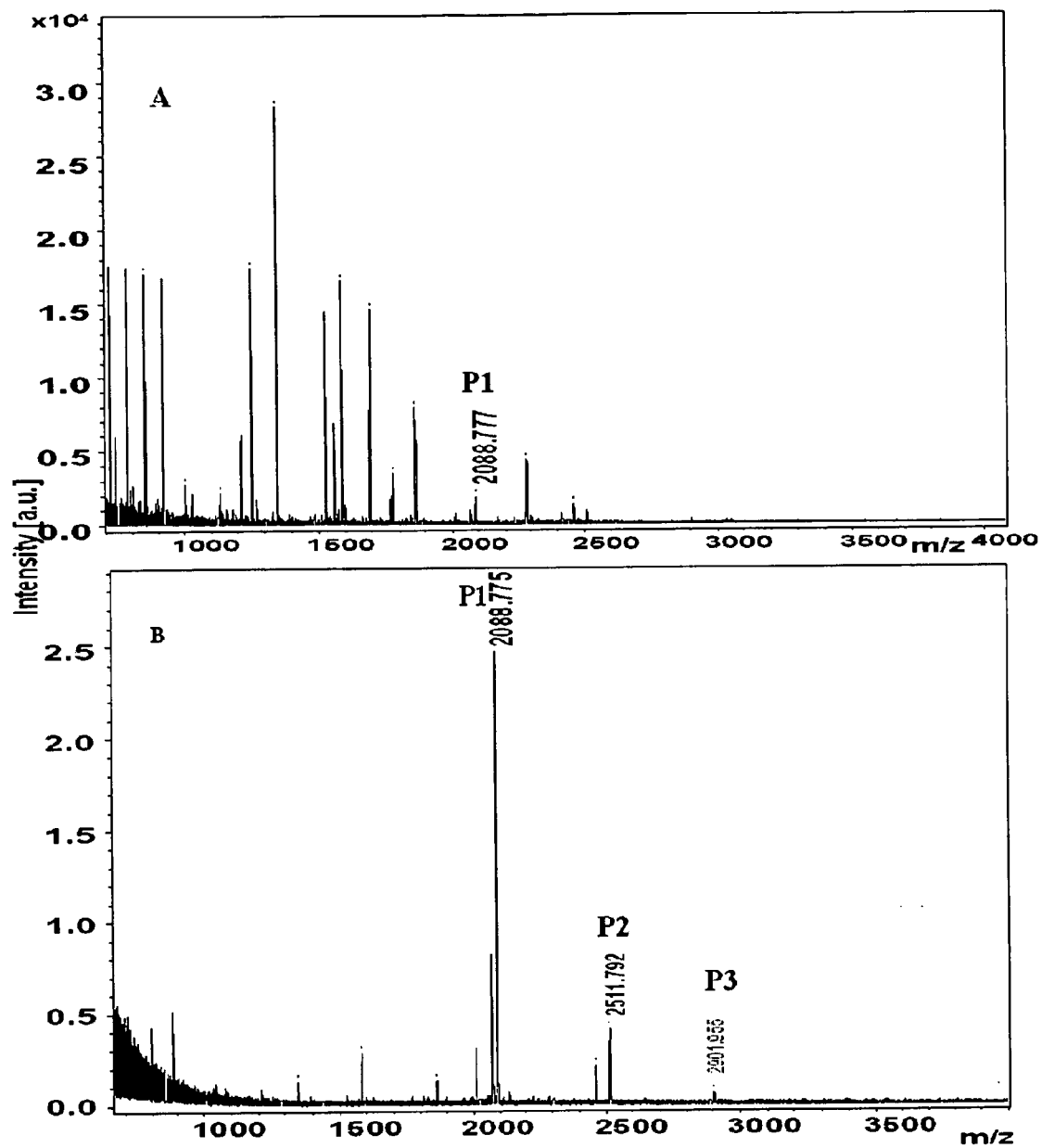
FIG. 16: MALDI-TOF of A) 500 fmol/μl ovalbumin tryptic digest, B) phosphopeptides from ovalbumin tryptic digest separated by open-tube latex coated capillary IDA-Fe+3 as described in Example 30.

Most phosphopeptides are highly acidic, but in order to test the universality of the approach, we used a tryptic peptide mixture derived from 500 fmol of in-solution digested ovalbumin (FIG. 16A). By database searching, a total of 16 peptide masses matched the ovalbumin protein sequence (64% amino acid sequence coverage). Three phosphopeptides P1, P2 and P3 were indicated in the data search. It is noticeable from FIG. 16A, that only low intensity ion signals from the predicted ovalbumin tryptic phosphopeptides P1 and P2 were observed using the standard sample preparation methods for MALDI-MS peptide mass mapping.

Figure 17:
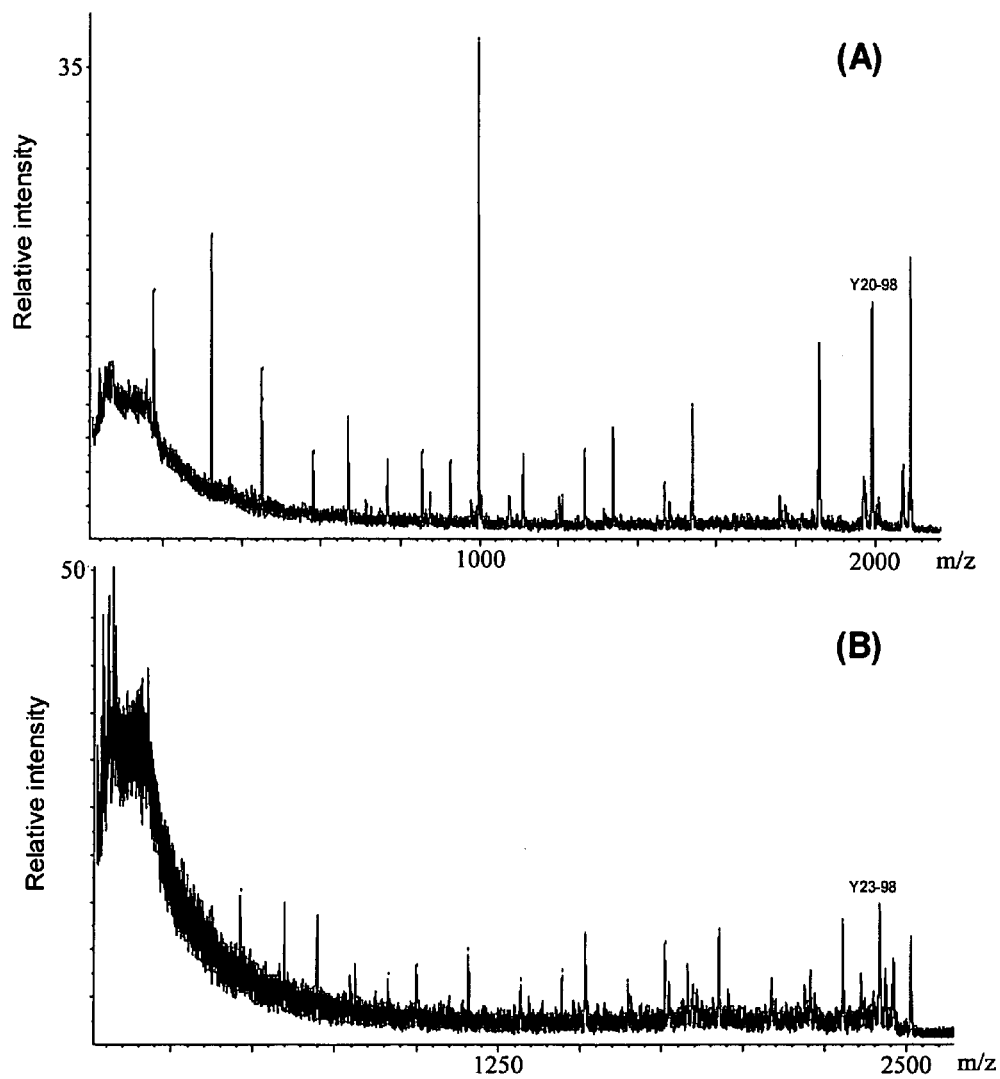
FIG. 17: MALDI-TOF/TOF of ovalbumin phosphopeptides as described in Example 30 with m/z A) 2088.77 Da (EVVGpSAEAGVDAASVSEEFR); B) 2512.15 Da. (LPG-FGDpSIEAQCGTSVNVHSSLR) after selective enrichment with IMAC capillary.

The tryptic peptide mixture was extracted with the IMAC column described in Example 20 using a pH 10.5 ammonium hydroxide solution, and the eluted solution was spotted directly onto the MALDI probe. The MALDI mass spectrum displayed an ion signal from three phosphopeptides (P1, m/z 2088.9; P2, m/z 2512.2; and P3, m/z 2909.4). The phosphopeptide P3 was assigned as an extended version of P2 due to incomplete tryptic digestion. The MALDI/MS recorded from this sample (FIG. 16B) was significantly less complex than the spectrum obtained from the crude peptide mixture. The most prominent signal in the mass spectrum, m/z 2088.9, was a phosphopeptide candidate (P1, 340-359). Additionally, the two other phosphopeptide candidates were detected at m/z 2512.2 (P2, 62-84) and m/z 2909.4 (P3, 59-84). The signal to background ratios of these phosphopeptide ion signals were significantly improved relative to those obtained from the un-separated peptide mixture demonstrating the importance of reducing the complexity of the peptide mixture and increasing the relative amount of phosphopeptides. FIG. 17 shows the MALDI-TOF/TOF spectra of the two phosphopeptides with m/z 2088.9 and 2512 showing the loss of 98 Da indicating the phosphorylation of peptide.

Example 31

Capturing Ovalbumin with a Concanavalin A Immobilized Capillary

A concanavalin A immobilized capillary was prepared as described in Example 25. After Con A was dissolved in acetate buffer and loaded to the capillary and allowed to react overnight at 40° C., the capillary was pretreated with wash solution (1 M NaCl, 5 mM $MgCl_2$, 5 mM $MnCl_2$, and 5 mM $CaCl_2$) and equilibrated with Tris buffer (pH 7.15, 0.5 M NaCl).

The Con A immobilized capillary was loaded with a solution containing 15 pmol each of ovalbumin, cytochrome c, and myoglobin in 200 µL of Tris buffer and recycled 10 times. After this binding step, the capillary was thoroughly washed with equilibrating buffer. The bound glycoprotein was eluted with 25 µl of 0.5 M methyl-alpha-D-mannopyranoside.

Figure 18:
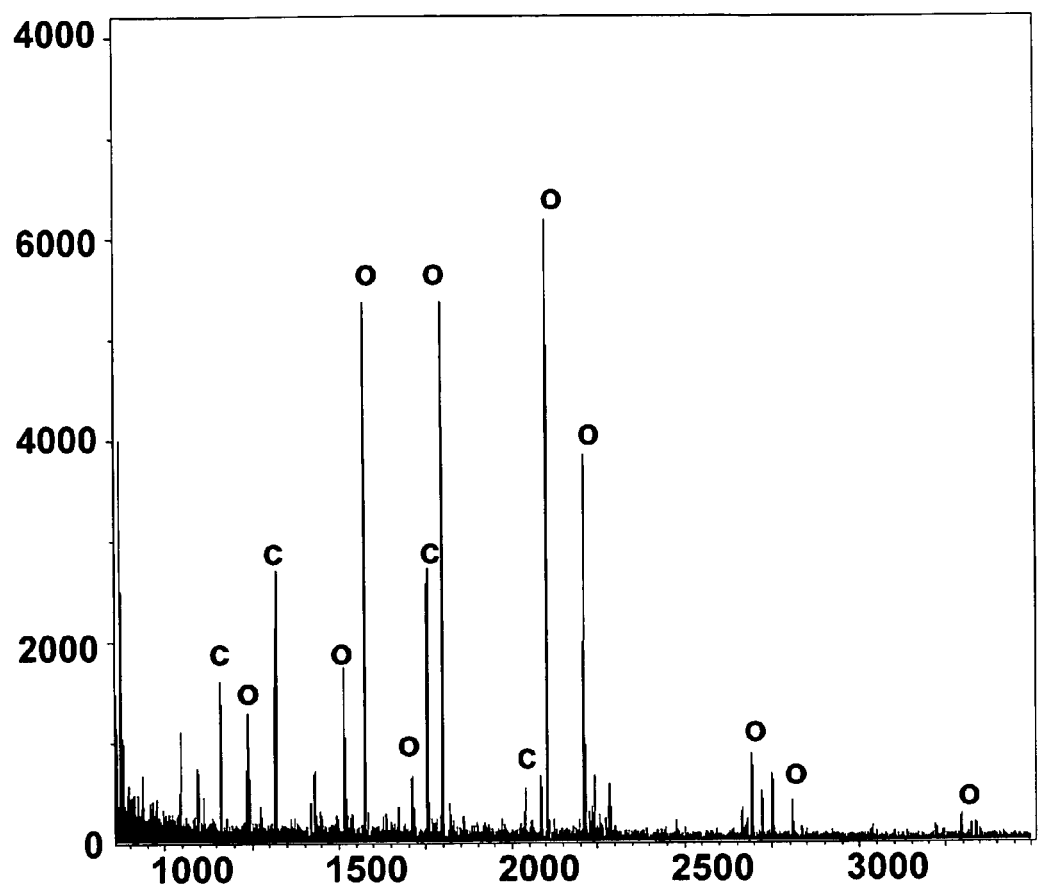
FIG. 18: MALDI-TOF spectrum of tryptic digest of ovalbumin (as described in Example 31) selectively captured from mixture of myoglobin and cytochrome c by Con A immobilized capillary: (o) ovalbumin Fragments; (c) Con A fragments.

The eluted solution was subsequently analyzed with MALDI/TOF using sinapinic acid as matrix. Only the peak of ovalbumin can be detected. In addition the elution solution was digested with trypsin and analyzed with MALDI-TOF using HCCA as matrix. The MALDI-TOF mass spectrum of the digest is presented in FIG. 18. Only peaks for ovalbumin (labelled o) and Con A (labelled c) are present in the spectrum showing that immobilized Con A selectively captured only glycoprotein.

Example 32

Synthesis of a Monoclonal Antibody Immobilized Capillary

A 200 µm ID 1 m fused silica capillary is prepared with covalently bound latex particles as described in example 20. The coated capillary is flushed with $H_2SO_4$ for 3 hours at 0.5 bar at 70° C. The capillary is washed thoroughly with water till it becomes neutral. The capillary is flushed with freshly prepared 0.1 M sodium (meta)periodate for one hour at 0.5 bar at room temperature, then washed with water. Monoclonal antibody solution in 0.1 M sodium acetate buffer of pH 6.4 containing 50 mM sodium cyanoborohydride is flushed through the capillary with 2 µL/min flow rate for 3 hours at 10° C. and then washed three times with 0.4 M Tris-HCl buffer of pH 7.2 containing 50 mM sodium cyanoborohydride and washed two times with water.

Example 33

Synthesis of a Latex Coated Capillary with Amino Functionality

A 200 µm ID 1 m fused silica capillary is rinsed and filled with 1.0 M NaOH. The capillary ends are sealed and heated at 100° C. for 2 hours in the oven. After cooling to room temperature, the two ends of the capillary are opened and the capillary is washed with 0.1 M HCl for 10 min, deionized water 10 min and acetone 15 min at 4 bar nitrogen pressure. Subsequently, the capillary is placed again in the oven at 120° C. and purged with nitrogen for 1 hour to remove residual water and acetone. A solution of 10% w/v glycidoxypropyltrimethoxysilane (Sigma-Aldrich) in dry toluene is prepared, de-aerated with helium for 15 min and filled into the pre-treated capillary. After both ends are sealed the capillary is placed in the oven at 70° C. for 6 hours. Thereafter, the capillary is taken out, washed extensively with toluene, methanol and blown dry with nitrogen. The capillary is flushed with a polystyrene amino latex suspension (100 nm purchased from Micromod Partikeltechnologie GmbH (Rostock-Warnemuende, Germany) diluted 1:1 with borate buffer pH 8.5 for 1 hour at room temperature. The filled capillary is sealed, left to react overnight at room temperature, and then the capillary is washed with deionized water to remove excess latex particles.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such embodiments.

What is claimed is:

1. A method for preparing a fused silica capillary, wherein the capillary has latex particles attached to the inner surface comprised of:
   a. providing a fused silica capillary; and
   b. covalently attaching epoxy-functionalized latex particles to the inner surface of the capillary, wherein the latex is covalently attached to the capillary inner surface at a pH in the range of 8.5-10.5.

2. The method of claim 1, wherein the latex particles are comprised of polystyrene.

3. The method of claim 2, wherein the polystyrene latex particles are further comprised of an immobilized metal.

4. The method of claim 1, wherein the latex particles have a diameter of at least 100 nm.

5. The method of claim 1, wherein the covalent attachment is performed at room temperature.

6. The method of claim 1, wherein the length of the fused silica capillary is in the range of 10 cm to 10 m.

* * * * *